United States Patent
Dhugga et al.

(10) Patent No.: US 7,176,349 B1
(45) Date of Patent: Feb. 13, 2007

(54) PRODUCTION OF POLYHYDROXYALKANOATE IN PLANTS

(75) Inventors: Kanwarpal S. Dhugga, Johnston, IA (US); Chun Ping Li, Johnston, IA (US); Jian G. Dong, Johnston, IA (US); William D. Hitz, Wilmington, DE (US); Matthias Liebergesell, West Des Moines, IA (US); Scott E. Nichols, Westchester, PA (US); Kristen K. Briggs, Del Mar, CA (US)

(73) Assignees: Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 613 days.

(21) Appl. No.: 10/089,281

(22) PCT Filed: Sep. 29, 2000

(86) PCT No.: PCT/US00/26963

§ 371 (c)(1),
(2), (4) Date: Sep. 11, 2002

(87) PCT Pub. No.: WO01/23596

PCT Pub. Date: Apr. 5, 2001

Related U.S. Application Data

(60) Provisional application No. 60/156,807, filed on Sep. 29, 1999.

(51) Int. Cl.
*C12N 15/29* (2006.01)
*C12N 15/52* (2006.01)
*C12N 15/63* (2006.01)
*C12N 15/82* (2006.01)

(52) U.S. Cl. .................. 800/281; 800/287; 800/298; 800/320.1; 536/23.2; 536/23.6; 435/419; 435/320.1

(58) Field of Classification Search .............. 536/23.2, 536/23.6; 435/419, 320.1; 800/281, 287, 800/298, 320.1
See application file for complete search history.

(56) References Cited

U.S. PATENT DOCUMENTS 5,245,023 A 9/1993 Peoples et al.
6,143,952 A 11/2000 Srienc et al.

FOREIGN PATENT DOCUMENTS

| WO | WO 94/11519 | 5/1994 |
|---|---|---|
| WO | WO 98/00557 | 1/1998 |
| WO | WO 98/00557 A2 | 1/1998 |
| WO | WO 99/00505 A1 | 1/1999 |
| WO | WO 99/35278 A1 | 7/1999 |
| WO | WO 99/45122 A1 | 9/1999 |
| WO | WO 00/55328 A1 | 9/2000 |

OTHER PUBLICATIONS

Hiltunen J. et al. The Journal of Biological Chemistry, Apr. 5, 1992; vol. 267, No. 10; pp. 6646-6653.*
McConnell et al, Nature 411 (6838): 709-713, 2001.*
Broun P. et al. Science vol. 282; Nov. 13, 1998, pp. 1315-1317.*
Koski M. et al., in The Journal of Biological Chemistry, Jun. 4, 2004; vol. 279, No. 23; pp. 24666-24672.*
Hiltunen J. et al. The Journal of Biological Chemistry, Apr. 5, 1992; vol. 267, No. 10; pp. 6646-6653.*
Fukui, T., et al., "Expression and Characterization of (R)-Specific Enoyl Coenzyme A Hydratase Involved in Polyhydroxyalkanoate Biosynthesis by *Aeromonas caviae*," *Journal of Bacteriology*, Feb. 1998, pp. 667-673, vol. 180(3), American Society for Microbiology, USA.
Hiltunen, J., et al., "Peroxisomal Multifunctional Beta-Oxidation Protein of *Saccharomyces cerevisiae*," *The Journal of Biological Chemistry*, Apr. 1992, pp. 6646-6653, vol. 267(10), The American Society for Biochemistry and Molecular Biology, Inc., USA.
Mittendorf, V., et al., "Synthesis of Medium-Chain-Length Polyhydroxyalkanoates in *Arabidopsis thaliana* Using Intermediates of Peroxisomal Fatty Acid Beta-Oxidation," *Proc. Natl. Acad. Sci. USA*, Nov. 1998, pp. 13397-13402, vol. 95, The National Academy of Sciences, USA.
Williams, M., et al., "Production of a Polyhydroxyalkanoate Biopolymer in Insect Cells with a Modified Eucaryotic Fatty Acid Synthase," *Applied and Environmental Microbiology*, Jul. 1996, pp. 2540-2546, vol. 62(7), American Society for Microbiology, USA.
EMBL Database Report for Accession No. AI657354, May 6, 1999 (XP-002167910).
EMBL Database Report for Accession No. BE056943, Jun. 20, 2000 (XP-002167911).

(Continued)

*Primary Examiner*—Russell P. Kallis
(74) *Attorney, Agent, or Firm*—Alston & Bird LLP

(57) ABSTRACT

The invention relates to the genetic manipulation of plants to produce polyhydroxyalkanoate, particularly in the peroxisomes. Methods for producing such polymers in plants and host cells are provided. Such methods find use in producing biodegradable thermoplastics in plants and other organisms. Nucleotide molecules, expression cassettes, and genetically manipulated host cells, plants, plant tissues, and seeds are also provided.

15 Claims, 5 Drawing Sheets

OTHER PUBLICATIONS

Caira, F., et al., "Differential Regulation by a Peroxisome Proliferator of the Different Multifunctional Proteins in a Guinea Pig: cDNA Cloning of the Guinea Pig D-Specific Multifunctional Protein 2," *Biochem. J.*, 1998, pp. 1361-1368, vol. 330, Great Britain.

Corton, J., et al., "Rat 17 β-Hydroxysteroid Dehydrogenase Type IV is a Novel Peroxisome Proliferator-Inducible Gene," *Mol. Pharmacol.*, 1996, pp. 1157-1166, vol. 50.

Dieuaide-Noubhani, M., et al., "Further Characterization of the Peroxisomal 3-Hydroxyacyl-CoA Dehydrogenase from Rat Liver," *Eur. J. Biochem.*, 1996, pp. 660-666, vol. 240.

Filppula, S., et al., "Changing Stereochemistry for a Metabolic Pathway in Vivo,"*J. Biol. Chem.*, 1995, pp. 27453-27457, vol. 270(46), The American Society for Biochemistry and Molecular Biology, Inc.

Kato, M., et al., "Production of a Novel Copolyester of 3-Hydroxybutyric Acid and Medium-Chain-Length 3-Hydroxyalkanoic Acids by *Pseudomonas* sp. 61-3 from Sugars," *Appl. Microbiol. Biotechnol.*, 1996, pp. 363-370, vol. 45.

Lee, E. et al., "Biosynthesis of Copolyesters Consisting of 3-Hydroxybutyric Acid and Medium-Chain-Length 3-Hydroxyalkanoic Acids From 1,3-Butanediol or from 3-Hydroxybutyrate by *Pseudomonas* sp. A33," *Appl. Microbiol. Biotechnol.*, 1995, pp. 901-909, vol. 42.

Liebergesell, M., et al., "Analysis of Polyhydroxyalkanoic Acid-Biosynthesis Genes of Anoxygenic Phototrophic Bacteria Reveals Synthesis of a Polyester Exhibiting an Unusual Composition," *Appl. Microbiol. Biotechnol.*, 1993, pp. 292-300, vol. 40.

Matsusaki, H., et al., "Cloning and Molecular Analysis of the Poly(3-hyroxybutrate) and Poly(3-hydroxybutrate-co-3-hydroxyalkanoate) Biosynthesis Genes in *Pseudomonas* sp. Strain 61-3," *J. Bacteriol.*, 1998, pp. 6459-6467, vol. 180(24).

Palosaari, P., et al., "Amino Acid Sequence Similarities of the Mitochondrial Short Chain $\Delta^3$, $\Delta^2$-Enoyl-CoA Isomerase and Peroxisomal Multifunctional $\Delta^3$, $\Delta^2$-Enoyl-CoA Isomerase, 2-Enoyl-CoA Hydratase, 3-Hydroxyacyl-CoA Dehydrogenase Enzyme in Rat Liver," *J. Biol. Chem.*, 1991, pp. 10750-10753, vol. 266(17), The American Society for Biochemistry and Molecular Biology, Inc.

Qin, Y., et al., "Peroxisomal Multifunctional Enzyme of β-Oxidation Metabolizing D-3-Hydroxycyl-CoA Esters in Rat Liver: Molecular Cloning, Expression and Characterization," *Biochem. J.*, 1997, pp. 21-28, vol. 321, Great Britain.

Solaiman, D., et al., "PCR Cloning of *Pseudomonas Resinovorans* Polyhyroxyalkanoate Biosynthesis Genes and Expression *Escherichia coli*," *Biotechnol. Lett*, 2000, pp. 789-794, vol. 22.

Steinbüchel, A., "PHB and Other Polyhydroxyalkanoic Acids," *Polyhydroxyalkanoic Acids*, 1996, pp. 403-464, vol. 6.

Timm, A. and A. Steinbüchel, "Cloning and Molecular Analysis of the Poly(3-hydroxyalkanoic acid) Gene Locus of *Pseudomonas Aeruginosa* PAO1," *Eur. J. Biochem.*, 1992, pp. 15-30, vol. 209.

GenBank Accession No. AF129396, Oct. 19, 2000.
GenBank Accession No. A49465, Mar. 7, 1997.
GenBank Accession No. AB009273, Sep. 17, 1998.
GenBank Accession No. AF042276, Jan. 5, 1999.
GenBank Accession No. AF078795, Dec. 9, 1998.
GenBank Accession No. AJ006237, Oct. 7, 1998.
GenBank Accession No. D43764, May 1, 1999.
GenBank Accession No. D88825, Aug. 19, 1997.
GenBank Accession No. E13102, Jun. 24, 1998.
GenBank Accession No. E15860, Jul. 28, 1999.
GenBank Accession No. J04987, Apr. 24, 1993.
GenBank Accession No. J05003, Apr. 26, 1993.
GenBank Accession No. L07893, Aug. 13, 1993.
GenBank Accession No. M58445, Apr. 26, 1993.
GenBank Accession No. M86456, Apr. 27, 1993.
GenBank Accession No. S83279, Mar. 12, 1997.
GenBank Accession No. U04848, Nov. 5, 1994.
GenBank Accession No. U37486, Oct. 3, 1996.
GenBank Accession No. U66242, Aug. 28, 1996.
GenBank Accession No. X65124, Apr. 18, 2005.
GenBank Accession No. X66592, Jul. 21, 1995.
GenBank Accession No. X78116, Sep. 13, 1996.
GenBank Accession No. X84260, Feb. 11, 1995.
GenBank Accession No. X94978, Apr. 18, 2005.
GenBank Accession No. Y13623, Apr. 18, 2005.
GenBank Accession No. Z28233, Apr. 18, 2005.
GenBank Accession No. Z28234, Apr. 18, 2005.
GenBank Accession No. Z28235, Mar. 18, 1998.
GenBank Accession No. Z73544, Aug. 26, 1997.

* cited by examiner

CONSTRUCT 1 (WILD TYPE yMFP):
FULL-LENGTH OF YEAST MULTIFUNCTIONAL PROTEIN
CONSTRUCT 2 (REDUCTASE):
C-TRUNCATED VERSION OF yMFP LACKING 271 AMINO ACIDS
COSTRUCT 3 (HYDRATASE):
N-TRUNCATED VERSION OF yMFP LACKING 318 AMINO ACIDS
COSTRUCT 4 (HYDRATASE):
N-TERMINALLY TRUNCATED VERSION OF yMFP LACKING 477 AMINO ACIDS
CONSTRUCT 5 (HYDRATASE):
MAIZE MFP-2

SEQUENCE LISTING

```
<160> NUMBER OF SEQ ID NOS: 27

<210> SEQ ID NO 1
<211> LENGTH: 1362
<212> TYPE: DNA
<213> ORGANISM: Zea mays
<220> FEATURE:
<221> NAME/KEY: CDS
<222> LOCATION: (233)..(1174)

<400> SEQUENCE: 1
gaattcccgg gtcgacccac gcgtccggtc ggcggggctg ccgcctgccg catcctcccc      60
tcgcccaccg tcgacgactt gatcccctcc caccgttgag gccgcctcct cacggcagcg     120
agccagcgac tcctctcttc gtctcctaca agtagccaga caccactccg actttgccgg     180
caacccgtcg acagcgacga ggcgcagcat aaggcatacg ggcacggcgg cc atg gcg     238
                                                          Met Ala
                                                            1 acc agc tcc aaa ccc gcc gcg ccc gtg gac ccc atg gtc gtg ctc gcc      286
Thr Ser Ser Lys Pro Ala Ala Pro Val Asp Pro Met Val Val Leu Ala
        5                  10                  15 cac gag ttc ccc gag gtg tca ttc gac tac gac gag agg gat gta gcg      334
His Glu Phe Pro Glu Val Ser Phe Asp Tyr Asp Glu Arg Asp Val Ala
 20                  25                  30 ttg tac gcg ctc ggg gtt ggt gcc tgc ggc gat gac gcc gtc gac gag      382
Leu Tyr Ala Leu Gly Val Gly Ala Cys Gly Asp Asp Ala Val Asp Glu
 35                  40                  45                  50 aag gag ctt cac ttc gtg tac cac agg gat ggg cag cca cac att aag      430
Lys Glu Leu His Phe Val Tyr His Arg Asp Gly Gln Pro His Ile Lys
                 55                  60                  65 acc ctt cct act ttt gtt tct tta ttt ccc aac aag aac agc aat ggg      478
Thr Leu Pro Thr Phe Val Ser Leu Phe Pro Asn Lys Asn Ser Asn Gly
             70                  75                  80 ctt gga ttt gtt gat gtg cct ggc ctt aac ttt gat gca agc ctt cta      526
Leu Gly Phe Val Asp Val Pro Gly Leu Asn Phe Asp Ala Ser Leu Leu
```

```
                85                  90                  95
ctg cat ggt caa caa tac ata gag atc tat agg cca atc cct tcg tat     574
Leu His Gly Gln Gln Tyr Ile Glu Ile Tyr Arg Pro Ile Pro Ser Tyr
        100                 105                 110 gtc agt gtt gta aac agg gtt aaa gta gtt ggt ttg cac gac aag ggg     622
Val Ser Val Val Asn Arg Val Lys Val Val Gly Leu His Asp Lys Gly
115                 120                 125                 130 aaa gca act att ctt gag ctc gaa act acc aca agc ctc aaa gag tca     670
Lys Ala Thr Ile Leu Glu Leu Glu Thr Thr Thr Ser Leu Lys Glu Ser
                135                 140                 145 ggg gaa att tta tgc atg aac agg agt act atc tac ttg cgt ggt gct     718
Gly Glu Ile Leu Cys Met Asn Arg Ser Thr Ile Tyr Leu Arg Gly Ala
            150                 155                 160 gga ggg ttt tca gac tct tca cgg cca tac tca tat gct acc tat cct     766
Gly Gly Phe Ser Asp Ser Ser Arg Pro Tyr Ser Tyr Ala Thr Tyr Pro
        165                 170                 175 gct aat caa gtt tct cgc att tct att cca aat tcg gca cct tct gca     814
Ala Asn Gln Val Ser Arg Ile Ser Ile Pro Asn Ser Ala Pro Ser Ala
    180                 185                 190 gta tgc gac gac cag aca aag caa tcc cag gca ttg tta tac agg cta     862
Val Cys Asp Asp Gln Thr Lys Gln Ser Gln Ala Leu Leu Tyr Arg Leu
195                 200                 205                 210 tct ggg gat tac aat cct ttg cat tca gac cca gat att gca cag ctt     910
Ser Gly Asp Tyr Asn Pro Leu His Ser Asp Pro Asp Ile Ala Gln Leu
                215                 220                 225 gct ggg ttc acc cgt cca atc ctg cac ggc ctc tgc acc cta gga ttc     958
Ala Gly Phe Thr Arg Pro Ile Leu His Gly Leu Cys Thr Leu Gly Phe
            230                 235                 240 gct gct cgc gcc gtc ata aaa tct ttc tgc aac ggc gaa ccg act gcg    1006
Ala Ala Arg Ala Val Ile Lys Ser Phe Cys Asn Gly Glu Pro Thr Ala
        245                 250                 255 gtg aag agc atc ttc ggc cgt ttc ctt ctg cac gtc tac ccc ggg gaa    1054
Val Lys Ser Ile Phe Gly Arg Phe Leu Leu His Val Tyr Pro Gly Glu
    260                 265                 270 acg ttg tcc act gag atg tgg ctt gac ggc cag aag gtg cac tac caa    1102
Thr Leu Ser Thr Glu Met Trp Leu Asp Gly Gln Lys Val His Tyr Gln
275                 280                 285                 290 acg aag gcc aag gag cgg aac cga gct gtc ctc tct gga tat gtg ttg    1150
Thr Lys Ala Lys Glu Arg Asn Arg Ala Val Leu Ser Gly Tyr Val Leu
                295                 300                 305 ctc cag cac atc ccc tcg tca ttg taagtaaaag ttttgtttct taaaattggt   1204
Leu Gln His Ile Pro Ser Ser Leu
            310 gcccgctgaa agcatttggc ttggctgtga taaattgagc acgaggtggg ctgccactgt  1264 aatgatagcc atgtatgggt ctgcacataa cacattcgta ctgtattgat aagaagcacg  1324 taccacttaa atacgcagat ccgaacgtct tgattttt                          1362

<210> SEQ ID NO 2
<211> LENGTH: 314
<212> TYPE: PRT
<213> ORGANISM: Zea mays

<400> SEQUENCE: 2

Met Ala Thr Ser Ser Lys Pro Ala Ala Pro Val Asp Pro Met Val Val
 1               5                  10                  15

Leu Ala His Glu Phe Pro Glu Val Ser Phe Asp Tyr Asp Glu Arg Asp
            20                  25                  30

Val Ala Leu Tyr Ala Leu Gly Val Gly Ala Cys Gly Asp Asp Ala Val
```

```
                    35                    40                       45
Asp Glu Lys Glu Leu His Phe Val Tyr His Arg Asp Gly Gln Pro His
        50                      55                       60

Ile Lys Thr Leu Pro Thr Phe Val Ser Leu Phe Pro Asn Lys Asn Ser
 65                      70                      75                       80

Asn Gly Leu Gly Phe Val Asp Val Pro Gly Leu Asn Phe Asp Ala Ser
                    85                       90                       95

Leu Leu Leu His Gly Gln Gln Tyr Ile Glu Ile Tyr Arg Pro Ile Pro
                100                    105                     110

Ser Tyr Val Ser Val Val Asn Arg Val Lys Val Gly Leu His Asp
            115                     120                     125

Lys Gly Lys Ala Thr Ile Leu Glu Leu Glu Thr Thr Thr Ser Leu Lys
        130                     135                     140

Glu Ser Gly Glu Ile Leu Cys Met Asn Arg Ser Thr Ile Tyr Leu Arg
145                     150                     155                     160

Gly Ala Gly Gly Phe Ser Asp Ser Ser Arg Pro Tyr Ser Tyr Ala Thr
                    165                     170                     175

Tyr Pro Ala Asn Gln Val Ser Arg Ile Ser Ile Pro Asn Ser Ala Pro
                180                     185                     190

Ser Ala Val Cys Asp Asp Gln Thr Lys Gln Ser Gln Ala Leu Leu Tyr
                195                     200                     205

Arg Leu Ser Gly Asp Tyr Asn Pro Leu His Ser Asp Pro Asp Ile Ala
            210                     215                     220

Gln Leu Ala Gly Phe Thr Arg Pro Ile Leu His Gly Leu Cys Thr Leu
225                     230                     235                     240

Gly Phe Ala Ala Arg Ala Val Ile Lys Ser Phe Cys Asn Gly Glu Pro
                245                     250                     255

Thr Ala Val Lys Ser Ile Phe Gly Arg Phe Leu Leu His Val Tyr Pro
                260                     265                     270

Gly Glu Thr Leu Ser Thr Glu Met Trp Leu Asp Gly Gln Lys Val His
            275                     280                     285

Tyr Gln Thr Lys Ala Lys Glu Arg Asn Arg Ala Val Leu Ser Gly Tyr
        290                     295                     300

Val Leu Leu Gln His Ile Pro Ser Ser Leu
305                     310
```

<210> SEQ ID NO 3
<211> LENGTH: 3252
<212> TYPE: DNA
<213> ORGANISM: Saccharomyces cerevisiae

<400> SEQUENCE: 3

```
tagaactctc ggcggttatt tgccaattt tactccaacg ggatcaaca tcagcaagaa      60 agcaaaggag gatggggtaa aaaaacaagg aagacaagta aagaaattat ataagaagtc     120
gtttctggct gctttactcc cagtgttgaa aggtagaagg acttatcagc taatttatta    180
agcaaggtac acatatacga gctaaacaaa cattcgattt atttcttatt tgagtaagcc    240
atgcctggaa atttatcctt caaagataga gttgttgtaa tcacgggcgc tggaggggc     300 ttaggtaagg tgtatgcact agcttacgca agcagaggtg caaaagtggt cgtcaatgat    360
ctaggtggca ctttgggtgg ttcaggacat aactccaaag ctgcagactt agtggtggat    420
gagataaaaa aagccggagg tatagctgtg caaattacg actctgttaa tgaaatgga    480 gagaaaataa ttgaaacggc tataaaagaa ttcggcaggg ttgatgtact aattaacaac    540
```

-continued

```
gctggaatat taagggatgt ttcatttgca aagatgacag aacgtgagtt tgcatctgtg     600
gtagatgttc atttgacagg tggctataag ctatcgcgtg ctgcttggcc ttatatgcgc     660
tctcagaaat ttggtagaat cattaacacc gcttcccctg ccggtctatt tggaaatttt     720
ggtcaagcta attattcagc agctaaaatg ggcttagttg gtttggcgga aaccctcgcg     780
aaggagggtg ccaaatacaa cattaatgtt aattcaattg cgccattggc tagatcacgt     840
atgacagaaa acgtgttacc accacatatc ttgaaacagt taggaccgga aaaaattgtt     900
cccttagtac tctatttgac acacgaaagt acgaaagtgt caaactccat tttttgaactc    960 gctgctggat tctttggaca gctcagatgg gagaggtctt ctggacaaat tttcaatcca    1020
gaccccaaga catatactcc tgaagcaatt ttaaataagt ggaaggaaat cacagactat    1080
agggacaagc catttaacaa aactcagcat ccatatcaac tctcggatta taatgattta    1140
atcaccaaag caaaaaaatt acctcccaat gaacaaggct cagtgaaaat caagtcgctt    1200
tgcaacaaag tcgtagtagt tacgggtgca ggaggtggtc ttgggaagtc tcatgcaatc    1260
tggtttgcac ggtacggtgc gaaggtagtt gtaaatgaca tcaaggatcc ttttttcagtt    1320 gttgaagaaa taaataaact atatggtgaa ggcacagcca ttccagattc ccatgatgtg    1380
gtcaccgaag ctcctctcat tatccaaact gcaataagta agtttcagag agtagacatc    1440
ttggtcaata acgctggtat tttgcgtgac aaatctttttt taaaaatgaa agatgaggaa    1500
tggtttgctg tcctgaaagt ccaccttttt tccacatttt cattgtcaaa agcagtatgg    1560
ccaatattta ccaaacaaaa gtctggattt attatcaata ctacttctac ctcaggaatt    1620
tatggtaatt ttggacaggc caattatgcc gctgcaaaag ccgccatttt aggattcagt    1680
aaaactattg cactggaagg tgccaagaga ggaattattg ttaatgttat cgctcctcat    1740
gcagaaacgg ctatgacaaa gactatattc tcggagaagg aattatcaaa ccactttgat    1800
gcatctcaag tctccccact tgttgttttg ttggcatctg aagaactaca aaagtattct    1860
ggaagaaggg ttattggcca attattcgaa gttggcggtg gttggtgtgg gcaaaccaga    1920
tggcaaagaa gttccggtta tgtttctatt aaagagacta ttgaaccgga agaaattaaa    1980
gaaaattgga accacatcac tgatttcagt cgcaacacta tcaacccgag ctccacagag    2040
gagtcttcta tggcaaacctt gcaagccgtg caaaaagcgc actcttcaaa ggagttggat    2100
gatggattat tcaagtacac taccaaggat tgtatcttgt acaatttagg acttggatgc    2160
acaagcaaag agcttaagta cacctacgag aatgatccag acttccaagt tttgcccacg    2220
ttcgccgtca ttccatttat gcaagctact gccacactag ctatggacaa tttagtcgat    2280
aacttcaatt atgcaatgtt actgcatgga gaacaatatt ttaagctctg cacgccgaca    2340
atgccaagta atggaactct aaagacactt gctaaacctt tacaagtact tgacaagaat    2400
ggtaaagccg ctttagttgt tggtggcttc gaaacttatg acattaaaac taagaaactc    2460
atagcttata cgaaggatc gttcttcatc agggggcgcac atgtacctcc agaaaaggaa    2520
gtgagggatg ggaaaagagc caagtttgct gtccaaaatt ttgaagtgcc acatggaaag    2580
gtaccagatt tgaggcgga gatttctacg aataaagatc aagccgcatt gtacaggtta    2640
tctggcgatt tcaatccttt acatatcgat cccacgctag ccaaagcagt taaatttcct    2700
acgccaattc tgcatgggct ttgtacatta ggtattagtg cgaaagcatt gtttgaacat    2760
tatggtccat atgaggagtt gaaagtgaga tttaccaatg ttgttttccc aggtgatact    2820
ctaaaggtta aagcttggaa gcaaggctcg gttgtcgttt ttcaaacaat tgatacgacc    2880
agaaacgtca ttgtattgga taacgccgct gtaaaactat cgcaggcaaa atctaaacta    2940
```

-continued

```
taatacaaaa aaagatttga ataatataaa aaatagcgat tatattcttt tcatttaaca    3000
gctttgttaa gccatatcct tacatacatc tttccctaca taactaacct acccatttta    3060 agtactttt cttacggac gcaacttttt tgtcatgtgt aatattaaca gttttaatct     3120
atatagagga agaggatgga taatattaca aagtgtatat aggttgtata tagatacatg    3180
catatgatgg gaagactatg aagagagaga tagtcatcat ggtaagacat ttatccagaa    3240
attcatgaat tc                                                         3252
```

```
<210> SEQ ID NO 4
<211> LENGTH: 1566
<212> TYPE: DNA
<213> ORGANISM: Saccharomyces cerevisiae
<220> FEATURE:
<221> NAME/KEY: CDS
<222> LOCATION: (1)..(1563)
<220> FEATURE:
<223> OTHER INFORMATION: Nucleotides 4-1566 of SEQ ID NO: 4 corresponds
      to nucleotides 1381-2943 of SEQ ID NO: 3.

<400> SEQUENCE: 4
```

```
atg gtc acc gaa gct cct ctc att atc caa act gca ata agt aag ttt      48
Met Val Thr Glu Ala Pro Leu Ile Ile Gln Thr Ala Ile Ser Lys Phe
 1               5                  10                  15 cag aga gta gac atc ttg gtc aat aac gct ggt att ttg cgt gac aaa      96
Gln Arg Val Asp Ile Leu Val Asn Asn Ala Gly Ile Leu Arg Asp Lys
            20                  25                  30 tct ttt tta aaa atg aaa gat gag gaa tgg ttt gct gtc ctg aaa gtc     144
Ser Phe Leu Lys Met Lys Asp Glu Glu Trp Phe Ala Val Leu Lys Val
        35                  40                  45 cac ctt ttt tcc aca ttt tca ttg tca aaa gca gta tgg cca ata ttt     192
His Leu Phe Ser Thr Phe Ser Leu Ser Lys Ala Val Trp Pro Ile Phe
    50                  55                  60 acc aaa caa aag tct gga ttt att atc aat act act tct acc tca gga     240
Thr Lys Gln Lys Ser Gly Phe Ile Ile Asn Thr Thr Ser Thr Ser Gly
65                  70                  75                  80 att tat ggt aat ttt gga cag gcc aat tat gcc gct gca aaa gcc gcc     288
Ile Tyr Gly Asn Phe Gly Gln Ala Asn Tyr Ala Ala Ala Lys Ala Ala
                85                  90                  95 att tta gga ttc agt aaa act att gca ctg gaa ggt gcc aag aga gga     336
Ile Leu Gly Phe Ser Lys Thr Ile Ala Leu Glu Gly Ala Lys Arg Gly
            100                 105                 110 att att gtt aat gtt atc gct cct cat gca gaa acg gct atg aca aag     384
Ile Ile Val Asn Val Ile Ala Pro His Ala Glu Thr Ala Met Thr Lys
        115                 120                 125 act ata ttc tcg gag aag gaa tta tca aac cac ttt gat gca tct caa     432
Thr Ile Phe Ser Glu Lys Glu Leu Ser Asn His Phe Asp Ala Ser Gln
    130                 135                 140 gtc tcc cca ctt gtt gtt ttg ttg gca tct gaa gaa cta caa aag tat     480
Val Ser Pro Leu Val Val Leu Leu Ala Ser Glu Glu Leu Gln Lys Tyr
145                 150                 155                 160 tct gga aga agg gtt att ggc caa tta ttc gaa gtt ggc ggt ggt tgg     528
Ser Gly Arg Arg Val Ile Gly Gln Leu Phe Glu Val Gly Gly Gly Trp
                165                 170                 175 tgt ggg caa acc aga tgg caa aga agt tcc ggt tat gtt tct att aaa     576
Cys Gly Gln Thr Arg Trp Gln Arg Ser Ser Gly Tyr Val Ser Ile Lys
            180                 185                 190 gag act att gaa ccg gaa gaa att aaa gaa aat tgg aac cac atc act     624
Glu Thr Ile Glu Pro Glu Glu Ile Lys Glu Asn Trp Asn His Ile Thr
        195                 200                 205
```

-continued

```
gat ttc agt cgc aac act atc aac ccg agc tcc aca gag gag tct tct    672
Asp Phe Ser Arg Asn Thr Ile Asn Pro Ser Ser Thr Glu Glu Ser Ser
    210                 215                 220 atg gca acc ttg caa gcc gtg caa aaa gcg cac tct tca aag gag ttg    720
Met Ala Thr Leu Gln Ala Val Gln Lys Ala His Ser Ser Lys Glu Leu
225                 230                 235                 240 gat gat gga tta ttc aag tac act acc aag gat tgt atc ttg tac aat    768
Asp Asp Gly Leu Phe Lys Tyr Thr Thr Lys Asp Cys Ile Leu Tyr Asn
                245                 250                 255 tta gga ctt gga tgc aca agc aaa gag ctt aag tac acc tac gag aat    816
Leu Gly Leu Gly Cys Thr Ser Lys Glu Leu Lys Tyr Thr Tyr Glu Asn
            260                 265                 270 gat cca gac ttc caa gtt ttg ccc acg ttc gcc gtc att cca ttt atg    864
Asp Pro Asp Phe Gln Val Leu Pro Thr Phe Ala Val Ile Pro Phe Met
        275                 280                 285 caa gct act gcc aca cta gct atg gac aat tta gtc gat aac ttc aat    912
Gln Ala Thr Ala Thr Leu Ala Met Asp Asn Leu Val Asp Asn Phe Asn
    290                 295                 300 tat gca atg tta ctg cat gga gaa caa tat ttt aag ctc tgc acg ccg    960
Tyr Ala Met Leu Leu His Gly Glu Gln Tyr Phe Lys Leu Cys Thr Pro
305                 310                 315                 320 aca atg cca agt aat gga act cta aag aca ctt gct aaa cct tta caa   1008
Thr Met Pro Ser Asn Gly Thr Leu Lys Thr Leu Ala Lys Pro Leu Gln
                325                 330                 335 gta ctt gac aag aat ggt aaa gcc gct tta gtt gtt ggc ggc ttc gaa   1056
Val Leu Asp Lys Asn Gly Lys Ala Ala Leu Val Val Gly Gly Phe Glu
            340                 345                 350 act tat gac att aaa act aag aaa ctc ata gct tat aac gaa gga tcg   1104
Thr Tyr Asp Ile Lys Thr Lys Lys Leu Ile Ala Tyr Asn Glu Gly Ser
        355                 360                 365 ttc ttc atc agg ggc gca cat gta cct cca gaa aag gaa gtg agg gat   1152
Phe Phe Ile Arg Gly Ala His Val Pro Pro Glu Lys Glu Val Arg Asp
    370                 375                 380 ggg aaa aga gcc aag ttt gct gtc caa aat ttt gaa gtg cca cat gga   1200
Gly Lys Arg Ala Lys Phe Ala Val Gln Asn Phe Glu Val Pro His Gly
385                 390                 395                 400 aag gta cca gat ttt gag gcg gag att tct acg aat aaa gat caa gcc   1248
Lys Val Pro Asp Phe Glu Ala Glu Ile Ser Thr Asn Lys Asp Gln Ala
                405                 410                 415 gca ttg tac agg tta tct ggc gat ttc aat cct tta cat atc gat ccc   1296
Ala Leu Tyr Arg Leu Ser Gly Asp Phe Asn Pro Leu His Ile Asp Pro
            420                 425                 430 acg cta gcc aaa gca gtt aaa ttt cct acg cca att ctg cat ggg ctt   1344
Thr Leu Ala Lys Ala Val Lys Phe Pro Thr Pro Ile Leu His Gly Leu
        435                 440                 445 tgt aca tta ggt att agt gcg aaa gca ttg ttt gaa cat tat ggt cca   1392
Cys Thr Leu Gly Ile Ser Ala Lys Ala Leu Phe Glu His Tyr Gly Pro
    450                 455                 460 tat gag gag ttg aaa gtg aga ttt acc aat gtt gtt ttc cca ggt gat   1440
Tyr Glu Glu Leu Lys Val Arg Phe Thr Asn Val Val Phe Pro Gly Asp
465                 470                 475                 480 act cta aag gtt aaa gct tgg aag caa ggc tcg gtt gtc gtt ttt caa   1488
Thr Leu Lys Val Lys Ala Trp Lys Gln Gly Ser Val Val Val Phe Gln
                485                 490                 495 aca att gat acg acc aga aac gtc att gta ttg gat aac gcc gct gta   1536
Thr Ile Asp Thr Thr Arg Asn Val Ile Val Leu Asp Asn Ala Ala Val
            500                 505                 510 aaa cta tcg cag gca aaa tct aaa cta taa                           1566
Lys Leu Ser Gln Ala Lys Ser Lys Leu
        515                 520
```

<210> SEQ ID NO 5
<211> LENGTH: 521
<212> TYPE: PRT
<213> ORGANISM: Saccharomyces cerevisiae
<220> FEATURE:
<223> OTHER INFORMATION: Nucleotides 4-1566 of SEQ ID NO: 4 corresponds to nucleotides 1381-2943 of SEQ ID NO: 3.

<400> SEQUENCE: 5

```
Met Val Thr Glu Ala Pro Leu Ile Ile Gln Thr Ala Ile Ser Lys Phe
  1               5                  10                  15

Gln Arg Val Asp Ile Leu Val Asn Asn Ala Gly Ile Leu Arg Asp Lys
                 20                  25                  30

Ser Phe Leu Lys Met Lys Asp Glu Glu Trp Phe Ala Val Leu Lys Val
             35                  40                  45

His Leu Phe Ser Thr Phe Ser Leu Ser Lys Ala Val Trp Pro Ile Phe
         50                  55                  60

Thr Lys Gln Lys Ser Gly Phe Ile Ile Asn Thr Thr Ser Thr Ser Gly
 65                  70                  75                  80

Ile Tyr Gly Asn Phe Gly Gln Ala Asn Tyr Ala Ala Lys Ala Ala
                 85                  90                  95

Ile Leu Gly Phe Ser Lys Thr Ile Ala Leu Glu Gly Ala Lys Arg Gly
            100                 105                 110

Ile Ile Val Asn Val Ile Ala Pro His Ala Glu Thr Ala Met Thr Lys
            115                 120                 125

Thr Ile Phe Ser Glu Lys Glu Leu Ser Asn His Phe Asp Ala Ser Gln
        130                 135                 140

Val Ser Pro Leu Val Leu Ala Ser Glu Glu Leu Gln Lys Tyr
145                 150                 155                 160

Ser Gly Arg Arg Val Ile Gly Gln Leu Phe Glu Val Gly Gly Trp
                165                 170                 175

Cys Gly Gln Thr Arg Trp Gln Arg Ser Ser Gly Tyr Val Ser Ile Lys
            180                 185                 190

Glu Thr Ile Glu Pro Glu Glu Ile Lys Glu Asn Trp Asn His Ile Thr
        195                 200                 205

Asp Phe Ser Arg Asn Thr Ile Asn Pro Ser Ser Thr Glu Glu Ser Ser
    210                 215                 220

Met Ala Thr Leu Gln Ala Val Gln Lys Ala His Ser Ser Lys Glu Leu
225                 230                 235                 240

Asp Asp Gly Leu Phe Lys Tyr Thr Thr Lys Asp Cys Ile Leu Tyr Asn
                245                 250                 255

Leu Gly Leu Gly Cys Thr Ser Lys Glu Leu Lys Tyr Thr Tyr Glu Asn
                260                 265                 270

Asp Pro Asp Phe Gln Val Leu Pro Thr Phe Ala Val Ile Pro Phe Met
            275                 280                 285

Gln Ala Thr Ala Thr Leu Ala Met Asp Asn Leu Val Asp Asn Phe Asn
        290                 295                 300

Tyr Ala Met Leu Leu His Gly Glu Gln Tyr Phe Lys Leu Cys Thr Pro
305                 310                 315                 320

Thr Met Pro Ser Asn Gly Thr Leu Lys Thr Leu Ala Lys Pro Leu Gln
                325                 330                 335

Val Leu Asp Lys Asn Gly Lys Ala Ala Leu Val Val Gly Gly Phe Glu
                340                 345                 350

Thr Tyr Asp Ile Lys Thr Lys Lys Leu Ile Ala Tyr Asn Glu Gly Ser
```

-continued

```
                355                 360                 365
    Phe Phe Ile Arg Gly Ala His Val Pro Pro Glu Lys Glu Val Arg Asp
        370                 375                 380

Gly Lys Arg Ala Lys Phe Ala Val Gln Asn Phe Glu Val Pro His Gly
    385                 390                 395                 400

Lys Val Pro Asp Phe Glu Ala Glu Ile Ser Thr Asn Lys Asp Gln Ala
                    405                 410                 415

Ala Leu Tyr Arg Leu Ser Gly Asp Phe Asn Pro Leu His Ile Asp Pro
                420                 425                 430

Thr Leu Ala Lys Ala Val Lys Phe Pro Thr Pro Ile Leu His Gly Leu
            435                 440                 445

Cys Thr Leu Gly Ile Ser Ala Lys Ala Leu Phe Glu His Tyr Gly Pro
        450                 455                 460

Tyr Glu Glu Leu Lys Val Arg Phe Thr Asn Val Val Phe Pro Gly Asp
    465                 470                 475                 480

Thr Leu Lys Val Lys Ala Trp Lys Gln Gly Ser Val Val Val Phe Gln
                    485                 490                 495

Thr Ile Asp Thr Thr Arg Asn Val Ile Val Leu Asp Asn Ala Ala Val
                500                 505                 510

Lys Leu Ser Gln Ala Lys Ser Lys Leu
            515                 520

<210> SEQ ID NO 6
<211> LENGTH: 1887
<212> TYPE: DNA
<213> ORGANISM: Saccharomyces cerevisiae
<220> FEATURE:
<221> NAME/KEY: CDS
<222> LOCATION: (1)..(1887)
<220> FEATURE:
<223> OTHER INFORMATION: Nucleotides 1-1887 of SEQ ID NO: 6 corresponds
      to nucleotides 241-2127 of SEQ ID NO: 3.

<400> SEQUENCE: 6 atg cct gga aat tta tcc ttc aaa gat aga gtt gtt gta atc acg ggc      48
Met Pro Gly Asn Leu Ser Phe Lys Asp Arg Val Val Val Ile Thr Gly
 1               5                  10                  15 gct gga ggg ggc tta ggt aag gtg tat gca cta gct tac gca agc aga      96
Ala Gly Gly Gly Leu Gly Lys Val Tyr Ala Leu Ala Tyr Ala Ser Arg
             20                  25                  30 ggt gca aaa gtg gtc gtc aat gat cta ggt ggc act ttg ggt ggt tca     144
Gly Ala Lys Val Val Val Asn Asp Leu Gly Gly Thr Leu Gly Gly Ser
         35                  40                  45 gga cat aac tcc aaa gct gca gac tta gtg gtg gat gag ata aaa aaa     192
Gly His Asn Ser Lys Ala Ala Asp Leu Val Val Asp Glu Ile Lys Lys
     50                  55                  60 gcc gga ggt ata gct gtg gca aat tac gac tct gtt aat gaa aat gga     240
Ala Gly Gly Ile Ala Val Ala Asn Tyr Asp Ser Val Asn Glu Asn Gly
 65                  70                  75                  80 gag aaa ata att gaa acg gct ata aaa gaa ttc ggc agg gtt gat gta     288
Glu Lys Ile Ile Glu Thr Ala Ile Lys Glu Phe Gly Arg Val Asp Val
                 85                  90                  95 cta att aac aac gct gga ata tta agg gat gtt tca ttt gca aag atg     336
Leu Ile Asn Asn Ala Gly Ile Leu Arg Asp Val Ser Phe Ala Lys Met
            100                 105                 110 aca gaa cgt gag ttt gca tct gtg gta gat gtt cat ttg aca ggt ggc     384
Thr Glu Arg Glu Phe Ala Ser Val Val Asp Val His Leu Thr Gly Gly
        115                 120                 125 tat aag cta tcg cgt gct gct tgg cct tat atg cgc tct cag aaa ttt     432
```

```
                Tyr Lys Leu Ser Arg Ala Ala Trp Pro Tyr Met Arg Ser Gln Lys Phe
                130                 135                 140 ggt aga atc att aac acc gct tcc cct gcc ggt cta ttt gga aat ttt      480
Gly Arg Ile Ile Asn Thr Ala Ser Pro Ala Gly Leu Phe Gly Asn Phe
145                 150                 155                 160 ggt caa gct aat tat tca gca gct aaa atg ggc tta gtt ggt ttg gcg      528
Gly Gln Ala Asn Tyr Ser Ala Ala Lys Met Gly Leu Val Gly Leu Ala
                165                 170                 175 gaa acc ctc gcg aag gag ggt gcc aaa tac aac att aat gtt aat tca      576
Glu Thr Leu Ala Lys Glu Gly Ala Lys Tyr Asn Ile Asn Val Asn Ser
            180                 185                 190 att gcg cca ttg gct aga tca cgt atg aca gaa aac gtg tta cca cca      624
Ile Ala Pro Leu Ala Arg Ser Arg Met Thr Glu Asn Val Leu Pro Pro
        195                 200                 205 cat atc ttg aaa cag tta gga ccg gaa aaa att gtt ccc tta gta ctc      672
His Ile Leu Lys Gln Leu Gly Pro Glu Lys Ile Val Pro Leu Val Leu
    210                 215                 220 tat ttg aca cac gaa agt acg aaa gtg tca aac tcc att ttt gaa ctc      720
Tyr Leu Thr His Glu Ser Thr Lys Val Ser Asn Ser Ile Phe Glu Leu
225                 230                 235                 240 gct gct gga ttc ttt gga cag ctc aga tgg gag agg tct tct gga caa      768
Ala Ala Gly Phe Phe Gly Gln Leu Arg Trp Glu Arg Ser Ser Gly Gln
                245                 250                 255 att ttc aat cca gac ccc aag aca tat act cct gaa gca att tta aat      816
Ile Phe Asn Pro Asp Pro Lys Thr Tyr Thr Pro Glu Ala Ile Leu Asn
                260                 265                 270 aag tgg aag gaa atc aca gac tat agg gac aag cca ttt aac aaa act      864
Lys Trp Lys Glu Ile Thr Asp Tyr Arg Asp Lys Pro Phe Asn Lys Thr
            275                 280                 285 cag cat cca tat caa ctc tcg gat tat aat gat tta atc acc aaa gca      912
Gln His Pro Tyr Gln Leu Ser Asp Tyr Asn Asp Leu Ile Thr Lys Ala
        290                 295                 300 aaa aaa tta cct ccc aat gaa caa ggc tca gtg aaa atc aag tcg ctt      960
Lys Lys Leu Pro Pro Asn Glu Gln Gly Ser Val Lys Ile Lys Ser Leu
305                 310                 315                 320 tgc aac aaa gtc gta gta gtt acg ggt gca gga ggt ggt ctt ggg aag     1008
Cys Asn Lys Val Val Val Val Thr Gly Ala Gly Gly Gly Leu Gly Lys
                325                 330                 335 tct cat gca atc tgg ttt gca cgg tac ggt gcg aag gta gtt gta aat     1056
Ser His Ala Ile Trp Phe Ala Arg Tyr Gly Ala Lys Val Val Val Asn
                340                 345                 350 gac atc aag gat cct ttt tca gtt gtt gaa gaa ata aat aaa cta tat     1104
Asp Ile Lys Asp Pro Phe Ser Val Val Glu Glu Ile Asn Lys Leu Tyr
            355                 360                 365 ggt gaa ggc aca gcc att cca gat tcc cat gat gtg gtc acc gaa gct     1152
Gly Glu Gly Thr Ala Ile Pro Asp Ser His Asp Val Val Thr Glu Ala
        370                 375                 380 cct ctc att atc caa act gca ata agt aag ttt cag aga gta gac atc     1200
Pro Leu Ile Ile Gln Thr Ala Ile Ser Lys Phe Gln Arg Val Asp Ile
385                 390                 395                 400 ttg gtc aat aac gct ggt att ttg cgt gac aaa tct ttt tta aaa atg     1248
Leu Val Asn Asn Ala Gly Ile Leu Arg Asp Lys Ser Phe Leu Lys Met
                405                 410                 415 aaa gat gag gaa tgg ttt gct gtc ctg aaa gtc cac ctt ttt tcc aca     1296
Lys Asp Glu Glu Trp Phe Ala Val Leu Lys Val His Leu Phe Ser Thr
                420                 425                 430 ttt tca ttg tca aaa gca gta tgg cca ata ttt acc aaa caa aag tct     1344
Phe Ser Leu Ser Lys Ala Val Trp Pro Ile Phe Thr Lys Gln Lys Ser
            435                 440                 445
```

-continued

| | | |
|---|---|---|
| gga ttt att atc aat act act tct acc tca gga att tat ggt aat ttt<br>Gly Phe Ile Ile Asn Thr Thr Ser Thr Ser Gly Ile Tyr Gly Asn Phe<br>450     455     460 | | 1392 |
| gga cag gcc aat tat gcc gct gca aaa gcc gcc att tta gga ttc agt<br>Gly Gln Ala Asn Tyr Ala Ala Ala Lys Ala Ala Ile Leu Gly Phe Ser<br>465    470     475     480 | | 1440 |
| aaa act att gca ctg gaa ggt gcc aag aga gga att att gtt aat gtt<br>Lys Thr Ile Ala Leu Glu Gly Ala Lys Arg Gly Ile Ile Val Asn Val<br>     485     490     495 | | 1488 |
| atc gct cct cat gca gaa acg gct atg aca aag act ata ttc tcg gag<br>Ile Ala Pro His Ala Glu Thr Ala Met Thr Lys Thr Ile Phe Ser Glu<br>500     505     510 | | 1536 |
| aag gaa tta tca aac cac ttt gat gca tct caa gtc tcc cca ctt gtt<br>Lys Glu Leu Ser Asn His Phe Asp Ala Ser Gln Val Ser Pro Leu Val<br>515     520     525 | | 1584 |
| gtt ttg ttg gca tct gaa gaa cta caa aag tat tct gga aga agg gtt<br>Val Leu Leu Ala Ser Glu Glu Leu Gln Lys Tyr Ser Gly Arg Arg Val<br>530     535     540 | | 1632 |
| att ggc caa tta ttc gaa gtt ggc ggt ggt tgg tgt ggg caa acc aga<br>Ile Gly Gln Leu Phe Glu Val Gly Gly Gly Trp Cys Gly Gln Thr Arg<br>545     550     555     560 | | 1680 |
| tgg caa aga agt tcc ggt tat gtt tct att aaa gag act att gaa ccg<br>Trp Gln Arg Ser Ser Gly Tyr Val Ser Ile Lys Glu Thr Ile Glu Pro<br>     565     570     575 | | 1728 |
| gaa gaa att aaa gaa aat tgg aac cac atc act gat ttc agt cgc aac<br>Glu Glu Ile Lys Glu Asn Trp Asn His Ile Thr Asp Phe Ser Arg Asn<br>580     585     590 | | 1776 |
| act atc aac ccg agc tcc aca gag gag tct tct atg gca acc ttg caa<br>Thr Ile Asn Pro Ser Ser Thr Glu Glu Ser Ser Met Ala Thr Leu Gln<br>595     600     605 | | 1824 |
| gcc gtg caa aaa gcg cac tct tca aag gag ttg gat gat gga tta ttc<br>Ala Val Gln Lys Ala His Ser Ser Lys Glu Leu Asp Asp Gly Leu Phe<br>610     615     620 | | 1872 |
| aag tac act acc aag<br>Lys Tyr Thr Thr Lys<br>625 | | 1887 |

<210> SEQ ID NO 7
<211> LENGTH: 629
<212> TYPE: PRT
<213> ORGANISM: Saccharomyces cerevisiae
<220> FEATURE:
<223> OTHER INFORMATION: Nucleotides 1-1887 of SEQ ID NO: 6 corresponds
   to nucleotides 241-2127 of SEQ ID NO: 3.

<400> SEQUENCE: 7

Met Pro Gly Asn Leu Ser Phe Lys Asp Arg Val Val Ile Thr Gly
1       5       10       15

Ala Gly Gly Gly Leu Gly Lys Val Tyr Ala Leu Ala Tyr Ala Ser Arg
     20       25      30

Gly Ala Lys Val Val Asn Asp Leu Gly Gly Thr Leu Gly Gly Ser
  35      40      45

Gly His Asn Ser Lys Ala Ala Asp Leu Val Val Asp Glu Ile Lys Lys
  50      55      60

Ala Gly Gly Ile Ala Val Ala Asn Tyr Asp Ser Val Asn Glu Asn Gly
65       70       75       80

Glu Lys Ile Ile Glu Thr Ala Ile Lys Glu Phe Gly Arg Val Asp Val
     85       90      95

Leu Ile Asn Asn Ala Gly Ile Leu Arg Asp Val Ser Phe Ala Lys Met
     100      105      110

-continued

```
Thr Glu Arg Glu Phe Ala Ser Val Val Asp Val His Leu Thr Gly Gly
        115                 120                 125

Tyr Lys Leu Ser Arg Ala Ala Trp Pro Tyr Met Arg Ser Gln Lys Phe
130                 135                 140

Gly Arg Ile Ile Asn Thr Ala Ser Pro Ala Gly Leu Phe Gly Asn Phe
145                 150                 155                 160

Gly Gln Ala Asn Tyr Ser Ala Ala Lys Met Gly Leu Val Gly Leu Ala
                165                 170                 175

Glu Thr Leu Ala Lys Glu Gly Ala Lys Tyr Asn Ile Asn Val Asn Ser
                180                 185                 190

Ile Ala Pro Leu Ala Arg Ser Arg Met Thr Glu Asn Val Leu Pro Pro
            195                 200                 205

His Ile Leu Lys Gln Leu Gly Pro Glu Lys Ile Val Pro Leu Val Leu
            210                 215                 220

Tyr Leu Thr His Glu Ser Thr Lys Val Ser Asn Ser Ile Phe Glu Leu
225                 230                 235                 240

Ala Ala Gly Phe Phe Gly Gln Leu Arg Trp Glu Arg Ser Ser Gly Gln
                245                 250                 255

Ile Phe Asn Pro Asp Pro Lys Thr Tyr Thr Pro Glu Ala Ile Leu Asn
                260                 265                 270

Lys Trp Lys Glu Ile Thr Asp Tyr Arg Asp Lys Pro Phe Asn Lys Thr
            275                 280                 285

Gln His Pro Tyr Gln Leu Ser Asp Tyr Asn Asp Leu Ile Thr Lys Ala
            290                 295                 300

Lys Lys Leu Pro Pro Asn Glu Gln Gly Ser Val Lys Ile Lys Ser Leu
305                 310                 315                 320

Cys Asn Lys Val Val Val Thr Gly Ala Gly Gly Leu Gly Lys
                325                 330                 335

Ser His Ala Ile Trp Phe Ala Arg Tyr Gly Ala Lys Val Val Val Asn
                340                 345                 350

Asp Ile Lys Asp Pro Phe Ser Val Val Glu Glu Ile Asn Lys Leu Tyr
            355                 360                 365

Gly Glu Gly Thr Ala Ile Pro Asp Ser His Asp Val Val Thr Glu Ala
370                 375                 380

Pro Leu Ile Ile Gln Thr Ala Ile Ser Lys Phe Gln Arg Val Asp Ile
385                 390                 395                 400

Leu Val Asn Asn Ala Gly Ile Leu Arg Asp Lys Ser Phe Leu Lys Met
                405                 410                 415

Lys Asp Glu Glu Trp Phe Ala Val Leu Lys Val His Leu Phe Ser Thr
                420                 425                 430

Phe Ser Leu Ser Lys Ala Val Trp Pro Ile Phe Thr Lys Gln Lys Ser
            435                 440                 445

Gly Phe Ile Ile Asn Thr Thr Ser Thr Ser Gly Ile Tyr Gly Asn Phe
            450                 455                 460

Gly Gln Ala Asn Tyr Ala Ala Ala Lys Ala Ala Ile Leu Gly Phe Ser
465                 470                 475                 480

Lys Thr Ile Ala Leu Glu Gly Ala Lys Arg Gly Ile Ile Val Asn Val
                485                 490                 495

Ile Ala Pro His Ala Glu Thr Ala Met Thr Lys Thr Ile Phe Ser Glu
            500                 505                 510

Lys Glu Leu Ser Asn His Phe Asp Ala Ser Gln Val Ser Pro Leu Val
            515                 520                 525
```

-continued

```
Val Leu Leu Ala Ser Glu Glu Leu Gln Lys Tyr Ser Gly Arg Arg Val
            530                 535                 540

Ile Gly Gln Leu Phe Glu Val Gly Gly Gly Trp Cys Gly Gln Thr Arg
545                 550                 555                 560

Trp Gln Arg Ser Ser Gly Tyr Val Ser Ile Lys Glu Thr Ile Glu Pro
                565                 570                 575

Glu Glu Ile Lys Glu Asn Trp Asn His Ile Thr Asp Phe Ser Arg Asn
            580                 585                 590

Thr Ile Asn Pro Ser Ser Thr Glu Glu Ser Ser Met Ala Thr Leu Gln
        595                 600                 605

Ala Val Gln Lys Ala His Ser Ser Lys Glu Leu Asp Asp Gly Leu Phe
    610                 615                 620

Lys Tyr Thr Thr Lys
625

<210> SEQ ID NO 8
<211> LENGTH: 6455
<212> TYPE: DNA
<213> ORGANISM: Pseudomonas oleovorans

<400> SEQUENCE: 8
gaattcctgc gcgtgcactc cccctccgcc gaggtccagg gccacggtaa cccccatcctg      60 cagttcggca agatcaacgt cggcctcagc ggcctggaac ctgccgggca atacgcactg     120
aaactgacct tcgacgacgg ccatgacagc ggcctgttca cctgggaata cctcgagcag     180
ctgtgcctgc gccaggaaca gctgtgggcc gagtacctcg acgaactgca caaggccggg     240
aaatcccgcg accctgccga gtcggtggtc aaactcatgc tctagcgcaa ggcctgcagg     300
atttagagcg catttcctaa aatcatctgt ttgaatgact tacagacagc ccagtgacgg     360
gctgtcttgc gcattacatg aaagtcgggt aaccaatggg ggtggcaagt tccctgcatc     420
aaattgcagg tagtcagaac cctcgcagca ccgctgttcc ttatcactgg tcacccgagt     480
agcagtaccg ggctcagaac tgtgcacccg ccacagcaac cggtactcgt ctcaggacaa     540
cggagcgtcg tagatgagta acaagaacaa cgatgagctg cagcggcagg cctcggaaaa     600
cacccctggg ctgaacccgg tcatcggtat ccgccgcaaa gacctgttga gctcggcacg     660
caccgtgctg cgccaggccg tgcgccaacc gctgcacagc gccaagcatg tggcccactt     720
tggcctggag ctgaagaacg tgctgctggg caagtccagc cttgccccgg aaagcgacga     780
ccgtcgcttc aatgacccgg catggagcaa caacccactt taccgccgct acctgcaaac     840
ctatctggcc tggcgcaagg agctgcagga ctggatcggc aacagcgacc tgtcgcccca     900
ggacatcagc gcgggccagt tcgtcatcaa cctgatgacc gaagccatgg ctccgaccaa     960
caccctgtcc aacccggcag cagtcaaacg cttcttcgaa accggcggca agagcctgct    1020
cgatggcctg tccaacctgg ccaaggacct ggtcaacaac ggtggcatgc cagccaggt    1080 gaacatggac gccttcgagg tgggcaagaa cctgggcacc agtgaaggcg ccgtggtgta    1140
ccgcaacgat gtgctggagc tgatccagta caagcccatc accgagcagg tgcatgcccg    1200
cccgctgctg gtggtgccgc cgcagatcaa caagttctac gtattcgacc tgagcccgga    1260
aaagagcctg gcacgctact gcctgcgctc gcagcagcag accttcatca tcagctggcg    1320
caacccgacc aaagcccagc gcgaatgggg cctgtccacc tacatcgacg cgctcaagga    1380
ggcggtcgac gcggtgctgg cgattaccgc agcaaggac ctgaacatgc tcggtgcctg    1440
ctccggcggc atcacctgca cggcattggt cggccactat gccgccctcg gcgaaaacaa    1500
```

-continued

| | |
|---|---|
| ggtcaatgcc ctgaccctgc tggtcagcgt gctggacacc accatggaca accaggtcgc | 1560 |
| cctgttcgtc gacgagcaga ctttggaggc cgccaagcgc cactcctacc aggccggtgt | 1620 |
| gctcgaaggc agcagagatgg ccaaggtgtt cgcctggatg cgccccaacg acctgatctg | 1680 |
| gaactactgg gtcaacaact acctgctcgg caacgagccg ccggtgttcg acatcctgtt | 1740 |
| ctggaacaac gacaccacgc gcctgccggc cgccttccac ggcgacctga tcgaaatgtt | 1800 |
| caagagcaac ccgctgaccc gcccggacgc cctggaggtt tgcggcactc cgatcgacct | 1860 |
| gaaacaggtc aaatgcgaca tctacagcct tgccggcacc aacgaccaca tcaccccgtg | 1920 |
| gcagtcatgc taccgctcgg cgcacctgtt cggcggcaag atcgagttcg tgctgtccaa | 1980 |
| cagcggccac atccagagca tcctcaaccc gccaggcaac cccaaggcgc gcttcatgac | 2040 |
| cggtgccgat cgcccgggtg acccggtggc ctggcaggaa aacgccacca gcatgccga | 2100 |
| ctcctggtgg ctgcactggc aaagctggct gggcgagcgt gccggcgagc tggaaaaggc | 2160 |
| gccgacccgc ctgggcaacc gtgcctatgc cgctggcgag gcatccccgg gcacctacgt | 2220 |
| tcacgagcgt tgagctgcag cgccgtggcc acctgcggga cgccacggtg ttcatttcac | 2280 |
| cccatgagtc acgcgcatgc cgcaacccta catcttcagg accgtcgagc tggacaacca | 2340 |
| gtccatccgc accgccgtcc gcccgggcaa accgcacctg acgccgttgc tgatcttcaa | 2400 |
| cggcatcggt gccaacctgg agctggtgtt tccgttcatc gaggcactgg acccggacct | 2460 |
| ggaagtcatt gcctttgacg tacccggggt cggcggctcg tccacgccgc gccacccata | 2520 |
| ccgcttcccc gggttggcca agctgacggc acgcatgctc gactacctcg actacggcca | 2580 |
| ggtcaatgtc atcggtgtgt cttggggcgg cgccctggcc cagcagttcg cccacgatta | 2640 |
| ccccgaacgc tgcaagaaac tggtgctggc cgccaccgca gccggtgcgg tgatggtgcc | 2700 |
| aggcaagccc aaggtgttgt ggatgatggc cagcccacgg cgttacgtgc agccgtcgca | 2760 |
| tgtcatccgc attgcgccga cgatctatgg cggcggcttc cggcgtgacc ccgaactggc | 2820 |
| catgcagcac gcctccaagg tgcgctccgg cggcaagatg ggctactact ggcagctgtt | 2880 |
| cgccgggctc ggctggacca gcatccactg gctgcacaag atccagcaac cgaccctggt | 2940 |
| gctggccggc gacgacgacc cgctgatccc gctgatcaac atgcgcctgc tggcctggcg | 3000 |
| gattcccaat gcccagctac acattatcga cgacggtcat tgttcctga tcacccgggc | 3060 |
| cgaggccgtc gccccgatca tcatgaagtt ccttcagcaa gaacgacagc gcgccgtcat | 3120 |
| gcaccctcgc ccggcttcgg gcgggtaaat cgatgcggcc ttcttcgcgg gcgcgcccgc | 3180 |
| tcccacaggg atggcgccga acctgtggga gcgggcatgc ccgcgaaggt ctcgacagcg | 3240 |
| aaatggctta gacgagggag tgttgccatg aaagacaaac cggccaaagg aacgccaacg | 3300 |
| cttcccgcca ccagcatgaa cgtgcagaac gccatcctcg gcctgcgcgg tcgtgacctg | 3360 |
| atttccacgc tgcgcaatgt cagccgccaa agcctgcgtc accgctgca caccgcacat | 3420 |
| cacctgttgg ccctgggtgg ccagctgggc cgggtgatac tgggtgacac accgcttcag | 3480 |
| ccgaacccgc gcgatccgcg cttcagcgac ccgacatgga gccagaaccc gttctaccgg | 3540 |
| cgcggcctgc aagcctacct ggcctggcag aagcagaccc gcctgtggat cgaggaaagc | 3600 |
| cacctggacg acgatgaccg ggcccgtgcg cacttcctgt tcaacctgat caacgatgcc | 3660 |
| ctggcgccaa gcaactcgct gctcaacccg ctggcggtca aggaactgtt caacagcggt | 3720 |
| ggccagagcc tggtgcgcgg cgtggcccac ctgctcgatg acctgcgcca caatgacggc | 3780 |
| ctgccacgcc aggtcgacga gcgcgccttc gaagtgggcg gcaacctggc cgcgactgcc | 3840 |
| ggcgccgtgg tgtttcgcaa cgagctgctg gaactgatcc agtacaagcc gatgagcgaa | 3900 |

-continued

| | |
|---|---|
| aagcagcacg cccggccact gctggtggtg ccgccacaga tcaacaagtt ctacatcttc | 3960 |
| gacctcagct cgaccaacag cttcgtccag tacatgctca agaatggcct gcaggtgttc | 4020 |
| atggtcagct ggcgcaaccc cgacccgcgc caccgcgaat ggggcctgtc cagctacgtg | 4080 |
| caggccctgg aagaagcgct caacgcttgc cgcagcatta gcggcaaccg cgaccccaac | 4140 |
| ctgatgggcg cctgcgccgg cggcctgacc atggccgcac tgcagggcca cctgcaggcc | 4200 |
| aagcaccagc tgcgccgggt gcgcagcgcc acctacctgg tcagcttgct ggacagcaag | 4260 |
| ttcgaaagcc ccgccagcct gttcgccgac gagcagacca tcgaggccgc caagcgccgc | 4320 |
| tcctaccagc gcggtgtgct ggatggcgcc gaggtggcgc ggatcttcgc ctggatgcgg | 4380 |
| cccaacgacc tgatctggaa ctactgggtc aacaactacc tgctcggcaa gacaccacca | 4440 |
| gccttcgaca tcctgtactg gaacgccgac agcacgcgcc tgcccgccgc gctgcatggc | 4500 |
| gacctgctgg acttcttcaa gctcaacccg ctgacccacc cagccggcct ggaggtatgc | 4560 |
| ggcacaccca tcgacctgca gaaggtcgag ctggacagtt tcaccgtggc cggcagcaac | 4620 |
| gaccacatca ccccgtggga tgcggtgtac cgctcggcct gctgctgggt ggcgaccgg | 4680 |
| cgcttcgtgc tggccaacag cgggcacatc cagagcatca tcaacccgcc cggcaacccc | 4740 |
| aaggcctact acctggccaa ccccaagctg tccagcgacc cgcgtgcctg gctccacgat | 4800 |
| gccaagcgca gcgaaggcag ctggtggccg ttgtggctgg agtggatcac cgcgcgctcc | 4860 |
| ggcccgctca aggcaccgcg cagcgaactg ggcaatgcca cctacccacc gctgggcccc | 4920 |
| gcgccgggca cctacgtgct gacccgatga gcatgccgac tggatgaaga ctcgcgaccg | 4980 |
| tatcctcgaa tgtgccctgc agctgttcaa ccagcagggc gaaccgaacg tatccaccct | 5040 |
| ggaaattgcc aacgaactgg gcatcagccc tggcaacctc tactaccact ccacggcaa | 5100 |
| ggagccgttg gtgctggggt tgttcgagcg ctttgaagaa gcgctgatgc ccttgctcga | 5160 |
| cccgccgctg gaggtacgcc tggacgccga ggattactgg ctgttcctgc acctgatcgt | 5220 |
| cgaacgcatg gcgcagtacc gcttcctgtt ccaggacctg tcgaacctga ccgggcgcct | 5280 |
| gcccaaactg gcccgcggca tgcgcaacct gatcaacgcg ctcaagcgca cactggcggc | 5340 |
| gttgctggcc agcctcaagg ccaagggtt ggtagagagc gagacccagg cgctggggca | 5400 |
| actggtggag cagatcaccc tgacactgat gttctcgctg gattatcagc gggtactggg | 5460 |
| gcgcgagggg gatgtgggga ttgtggtgta ccaggtgatg atgctggtgg cgccgcatct | 5520 |
| gcaggcccag gcgcgggggg cggcggagca attggcggtg cggtatctgg aggggtaagc | 5580 |
| ctgttgattc ggtgtcgcgg cttttcgcggg catgcccgct cccacaggtg aaatgcagtg | 5640 |
| ctcgagtgca cacaggacct gtgggagcgg gcaagcccgc gaagatggcg acgcggtatc | 5700 |
| agatcagggt accggtgcct gtctgtgccg aaggcgggtt gctggccgga gccgcagtgg | 5760 |
| gcgccgaagc tgcgctagcg gccggagcgg cgctggccgc tggagctgcc ggcttggcgg | 5820 |
| ctgccggctt ggccggtgct tcttcactg caggcttctt cgccacagcc ggtttggccg | 5880 |
| ctgccggttt gccgcaggct tggccgccgc agtcttggca gcaggtttag ccgctgcggc | 5940 |
| cttggctgcc ggcttggctg ccgcggtttt gccgcaggct tggccgctgc cgtcttggcc | 6000 |
| agtggcttgg ccgccgcctt gctgcagcc ggtttggctg cagtgcgcga cgaaatcggg | 6060 |
| gtaaccgaag cgccggtgag tttctcgatc tgcttggtca ggctgtccac ctgctggtgc | 6120 |
| agggccttga tctcgttgcg gctcggcacg ccaaggcgcg agatggcact gttcaggcgc | 6180 |
| ttgtcgaagg cctcttcgag ttcgctccac ttgcctagcg cacggtcctt cacgcccgac | 6240 |

-continued

| | |
|---|---|
| acacgcgaag tggtcgacga cttggcagtt tcagcaacat cttctgcggt cttcttcgcc | 6300 |
| tgtttctcgg ccttctcgcc atcctttacc agcgagtcga acagcttcgg gccgtcctgg | 6360 |
| tcgatcttcg aatagatacc aagccccgcc agccagatct tgcgggagta cttctcgatc | 6420 |
| ccgccgccca ggagctgcct tctttctcgg aattc | 6455 |

<210> SEQ ID NO 9
<211> LENGTH: 5054
<212> TYPE: DNA
<213> ORGANISM: Pseudomonas putida

<400> SEQUENCE: 9

| | |
|---|---|
| ctgcagtcga cctcgccttg ccagtgggcg gcgagcatca ggccctcttc atcgggcagg | 60 |
| atgaaaacct gcaaggccgg ctggcggcag tcgatctcga tgaccttgcc ctccagcgcg | 120 |
| gccagccgcg gcagggccgt gctgtccatg cgcaggacgc ggttcaggcc atgttcggcg | 180 |
| ctggcgagca gccggccag cagcatcagg gcttgatccc ccgatgcacg gcaacgatgc | 240 |
| cgctggtcat gttgtggtag gtgacccggt cgaaaccggc ctcgaccatc atggccttca | 300 |
| gggtttcctg atcggggtgc atgcggatcg actcggcgag gtaacggtag ctctccgaat | 360 |
| cgttggtgat cagcttgccg ccagcggca tgaaggcgaa cgagtaggcg tcgtaggcct | 420 |
| tggacatcag cttgttggtc ggcttggaga actccagcac cagcaggcga ccgcctggct | 480 |
| tgagcacgcg cagcatcgag cggatggctt cgtccttgtg ggtgacgttg cgcaggccga | 540 |
| aggcgatggt cacgcagtcg aagtggttgt ccgggaatgg cagcttctcg gcgtcggcct | 600 |
| gaacgaactc gatgttgccg gccacgccac ggtcgagcag gcggtcacga ccgaccttga | 660 |
| gcatcgattc gttgatgtcg gccagcacta cctgaccggt cgggccgacc agccgcgaga | 720 |
| acttggcggc caggtcgccg gtaccgccgg cgatgtccag tacacgattg ccggcgcgta | 780 |
| cgcccgacag ctcgatggtg aagcgcttcc acaggcggtg catgccgccg gaaagcacat | 840 |
| cgttcatcag gtcgtacttg gccgctaccg agtggaacac ctcggcgact tcttcgcct | 900 |
| tctggctttc agggacgtcc tggtaaccga aatgggtggt gggttcggcg tggtcgcctt | 960 |
| tgcgctggtc gttcatatcg cttcaccgga aaaattacc gccattctag ggcgaacggg | 1020 |
| cagatttgtc ttggcggggt gtgccagtgg gcagggcgg gcataatgcc cattatgtct | 1080 |
| tcatcttcag gaacacccgc atgacccaga tcagcgtcga acgcaaacat tccctcggcc | 1140 |
| gcgatgccgc ccgtgccaag gctgaagcgc tggtcgacaa actgaccgc gaatacgacc | 1200 |
| tcaaggccac ctggaacggc gacagggtcg acgtggcgcg cagcggtgcc aacggcagcg | 1260 |
| tgcacatctt cgatgaccgc atccgcgtcg aattgaagct gggcatgatg ctgtcgatga | 1320 |
| tgagcggcac catcaagggc gagatcgagc gggcgctgga caaagccctg gcctgacccc | 1380 |
| ttccggggc catgctcgtt caccttaggg tgaagattct aatttccctc tctaccttgt | 1440 |
| gctcaagccc aacctccatg gcggtttat cctccactca tgagcatgag gtacagagca | 1500 |
| tggccaaagt gactgtgaag aaaaaggacg acgccccggg cacgctgggc gaggtgcgcg | 1560 |
| gctacgcgcg caagatctgg ctggcgggca tcggcgccta tgcgcgtgtg gccaggaag | 1620 |
| gctccgacta cttcaatgag ctggtcaagg ccggcgaagg cgtcgagaag cgtggcaaga | 1680 |
| agcgcatcga caaggagctc gatgctgcca acaatcagat cgaagaagcg acccaggaag | 1740 |
| tcagtcgcgt acgcggcaag gtcgaagttc aactggacaa gatcgaaaaa gctttcgacg | 1800 |
| cgcgggtagg tcgcgccttg aatcgccttg gcattccgtc taaacatgac gttgaggcgt | 1860 |
| tgtccatcaa gcttgaacag ctgcacgagc tgctcgagcg cgtcgcgcac aaaccataag | 1920 |

-continued

```
gagagcagga tggctggcaa gaagaattcc gagaaagaag gcagctcctg ggtcggcggg    1980
atcgagaagt actcccgcaa gatctggctg gcggggcttg gtatctattc gaagatcgac    2040
caggacggcc cgaagctgtt cgactcgctg gtgaaggatg gcgagaaggc cgagaagcag    2100
gcgaagaaga ccgccgaaga tgttgctgaa actgccaagt cgtcgaccac ttcgcgtgtg    2160
tcgggcgtga aggaccgtgc gctgggcaag tggagcgaac tcgaagaggc cttcgacaag    2220
cgcctgaaca gcgccatctc gcgccttggc gtgccgagcc gcaacgagat caaggccctg    2280
caccagcagg tggacagcct gaccaagcag atcgagaaac ttaccggcgc ttcgcttacc    2340
ccgatttcgt cgcgcgctgc ggccaaaccg gctgcgagca aggcggcggc caagccactg    2400
gccaagacgg cagcggccaa gcctgcggcg aaaactgcgg cggccaagcc ggcggccaag    2460
actgctgcgg cgaaacctgc tgccaagact gcagcggcca agcctgcggc gaaaccggca    2520
gcggccaagc cggctgtggc gaagaagccg gcagtgaaga agcaccggca agccagca     2580 gccgccaagc cggcagctcc agcggcgagc gccgctccga ccgctagcgc agctcctgca    2640
ccaaccgcgg ctccgccag caatccgcct tcggcaccga caggcaccgg taccctgatc    2700
tgataccgcg tcgccttctt cgcgggcttg cccgctccca caggtcctgt gtgcactcga    2760
gcactgcatt tcacctgtgg gagcgggcat gcccgcgaaa gccgcgacac cgaaacaaca    2820
ggcttacccc tccagatacc tcaccgccaa ctgctccgcc gcccccgcg cctgggcctg      2880 cagatgcggc gccaccagca tcatcacctg gtacaccaca atcccacat cccctcgcg     2940 ccccagtacc cgctggtaat ccagcgagaa catcagtgtc agggtgatct gctccaccag    3000
ttgccccagc gcctgggtct cgctctctac cagcccctgg cccttgaggc tggccagcaa    3060
cgccgccagt gtgcgcttga gtgcgttgat caggctgcgc atgccgcggg ccagtttggg    3120
caggcgcccg gtcaggttcg acaggtcctg gaacaggaag cggtactgcg ccatgcgttc    3180
gacgatcagg tgcaggaaca gccagtaatc ctcggcatcc aggcgtacct ccagtggcgg    3240
gtcgagcaag ggcattagcg cttcttcaaa gcgctcgaac agccccagca ccaacggctc    3300
cttgccgtgg aagtgtagt agaggttgcc ggggctgatg cccagttcgt tggcaatttc    3360
cagggtggat acgttcggtt cgccctgctg gttgaacagc tgcagggcac attccaggat    3420 acgtcgcga gtcttcatcc agtcggcatg ctcatcgggt cagcacgtag gtgcccggcg    3480
cagggcccag cggtgggtag gtggcattgc ccagttcgct gcgtggtgcc ttgagcgggc    3540
cggagcgtgg tgtgatccac tccagccaca acggccacca gctgccttcg ctgcgcttgg    3600
cgtcgtggaa ccaggcacgg gggtcgctgg acagcttggg gttggccagg taataggcct    3660 tgggggttgcc gggcgggttg atgatgctct ggatgtgccc gctgttggcc agcacgaagc    3720
gacggtcgcc gcccagcagc aaggccgagc ggtacaccgc atcccacggg gtgatgtggt    3780
cgttgctgcc ggccacggtg aaactgtcca gatcgacctt ctgcaggtcg atggggtgc     3840 cgcatacctc caggccggct gggtgagtca gcgggttgag cttgaagaag tccagcaggt    3900
cgccatgcag cgcggcgggc aggcgcgtgc tgtcggcgtt ccagtacagg atgtcgaaag    3960
ctggtggtgt cttgccgagc aggtagttgt tgacccagta gttccagatc aggtcgttgg    4020
gccgcatcca ggcgaagatc cgcgccacct cggcgccatc cagcacgcct cgttggtagg    4080
agcggcgctt ggcggcttcg atggtctgct cgtcggcgaa caggctggcg gggctttcga    4140
acttgctgtc cagaaggctg accaggtagg tggcgctgcg cacccgacgc agctggtgct    4200
tggcctgcag gtgaccctgt agcgcggcca tggtcaggcc gccggcgcag gccccatca    4260
```

-continued

```
ggttggggtc gcggttgccg ctgatgctgc ggcaagcgtt gagcgcttct tccaggcct      4320 gcacgtagct cgacaggccc cattcgcggt ggcgcgggtc ggggttgcgc cagctcacca      4380
tgaacacctg caggccattc ttgagcatgt actggacgaa gctgttggtc gagctgaggt      4440
cgaagatgta gaacttgttg atctgtggcg gcactaccag cagtggccgg gcgtgctgct      4500
tttcgctcat cggcttgtac tggatcagct ccagcagctc gttgcgaaac accacggcgc      4560
cggcggttgc agccaggttg ccgcccactt cgaaggcgcg ctcgtcgacc tggcgtggta      4620
ggccatcgtt gtggcgcagg tcatcgagca ggtgggccac ccgcgtacc aggtctggc       4680 caccgctgtt gaacagttcc ttgaccgcca gcgggttgag cagcgagttg ctcggcgcca      4740
gtgcatcgtt gatcaggttg aacaggaagt gcgcacgggc ccggtcatcg tcgtccaggt      4800
ggctttcctc gatccacagg cgggtctgct tctgccaggc caggtaggct tgcaggccgc      4860
gccggtagaa cgggttctgg ctccatgtcg ggtcgctgaa gcgcggatcg cgcgggttcg      4920
gctgaaacgg tgtgtcaccc agcatcaccc tgcccagctg accacccagg ccaacaggt      4980 gatgcgcggt gtgcagcggg tgacgcaggc tttggcggct gacattgcgc agcgtggaaa      5040
tcaggtcacg gccg                                                        5054
```

<210> SEQ ID NO 10
<211> LENGTH: 7311
<212> TYPE: DNA
<213> ORGANISM: Pseudomonas aeruginosa

<400> SEQUENCE: 10

```
ctgcagggcc gcctgccgat ccgcgtggag ctcaaggccc tcagtccgaa cgatttcgag      60
cgcatcctca ccgagccgca tgcctcgctc accgagcagt accgcgagct gctgaagacc      120
gaggggctgg ccatcgagtt cgccgaggac ggcatcaagc gccttgccga gatcgcctgg      180
caggtcaacg agaagaccga gaacatcggt gcccgccgcc tgcatacgct gctcgagcgg      240
ctgctggaag aggtctcgtt cagcgccgcc gacctggcca gcgagcatag cgacaagccg      300
atcctgatcg atgccggcta cgtcaacagc cacctcggcg agctggccga ggacgaggac      360
ctgtcccgct acatcctttg accaccgccg ccgccacggc caacaccgtg gcggcgggcc      420
gcgcggtccc gaaccggggt atccttgtac tccgcccttc cgcgagtccg atgcgatgcg      480
tatcccttcc gccatccagc tgcacaaagc ctcgaagacc ctgaccctgc gctacggcga      540
ggatagctac gacctgcctg ccgagttcct ccgcgtgcat cgccctcgg ccaggtcca       600 gggccacggc aacccggtat gcagtacgg caagctgaac gtcggcctgg tcggcgtcga      660
acccgccggc cagtacgcac tgaagctgag cttcgacgac ggccacgaca gcggcctgtt      720
cacctgggac tacctgtacg agctggcgac ccgcaaggac cagctatggg ccgactacct      780
ggcggagctg ccagcgccg gcaagtcgcg cgaccccgac gagtcggtcg tcaagctgat      840
gctctgaagc gccgggccga gtgccccttc gcggcacacg gcatccaggc gatttttctc      900
cgctgccccg aacgagggca cgtcatttgc aacattcgcc ccgcagactg ccagaccaga      960
catccggtcg gcgcggtcgc cacggcgaat gtcctaccct gcacggcagc aacgctctag      1020
tccgcaggtc ggccgctcgc cgggccagcc acgccggcca ccgatgcttc tgccagcttg      1080
cacgccagcg gaaactcgcg taaccaagac ggtgcagccc cttgtccggg ttcccttccc      1140
tgacgtgcgt ccgccccgcc ctgaaacgtg cgggtgggct ggtagtcgag cagtagccgg      1200
ccggacacct agtccccggt ttcgttgcgg tcccctgttt cgcctcgaac aatggagcgt      1260
tgccgatgag tcagaagaac aataacgagc ttcccaagca agccgcggaa aacacgctga      1320
```

-continued

```
acctgaatcc ggtgatcggc atccggggca aggacctgct cacctccgcg cgcatggtcc   1380
tgctccaggc ggtgcgccag ccgctgcaca gcgccaggca cgtggcgcat ttcagcctgg   1440
agctgaagaa cgtcctgctc ggccagtcgg agctacgccc aggcgatgac gaccgacgct   1500
tttccgatcc ggcctggagc cagaatccac tgtacaagcg ctacatgcag acctacctgg   1560
cctggcgcaa ggagctgcac agctggatca gccacagcga cctgtcgccg caggacatca   1620
gtcgtggcca gttcgtcatc aacctgctga ccgaggcgat gtcgccgacc aacagcctga   1680
gcaacccggc ggcggtcaag cgcttcttcg agaccggcgg caagagcctg ctggacggcc   1740
tcggccacct ggccaaggac ctggtgaaca cggcgggat gccgagccag gtggacatgg   1800
acgccttcga ggtgggcaag aacctggcca ccaccgaggg cgccgtggtg ttccgcaacg   1860
acgtgctgga actgatccag taccggccga tcaccgagtc ggtgcacgaa cgcccgctgc   1920
tggtggtgcc gccgcagatc aacaagttct acgtcttcga cctgtcgccg gacaagagcc   1980
tggcgcgctt ctgcctgcgc aacggcgtgc agaccttcat cgtcagttgg cgcaacccga   2040
ccaagtcgca gcgcgaatgg ggcctgacca cctatatcga ggcgctcaag gaggccatcg   2100
aggtagtcct gtcgatcacc ggcagcaagg acctcaacct cctcggcgcc tgctccggcg   2160
ggatcaccac cgcgacgctg gtcggccact acgtggccag cggcgagaag aaggtcaacg   2220
ccttcaccca actggtcagc gtgctcgact tcgaactgaa tacccaggtc gcgctgttcg   2280
ccgacgagaa gactctggag gccgccaagc gtcgttccta ccagtccggc gtgctggagg   2340
gcaaggacat ggccaaggtg ttcgcctgga tgcgccccaa cgacctgatc tggaactact   2400
gggtcaacaa ctacctgctc ggcaaccagc cgccggcgtt cgacatcctc tactggaaca   2460
acgacaccac gcgcctgccc gccgcgctgc acggcgagtt cgtcgaactg ttcaagagca   2520
acccgctgaa ccgccccggc gcctggagg tctccggcac gcccatcgac ctgaagcagg   2580
tgacttgcga cttctactgt gtcgccggtc tgaacgacca catcaccccc tgggagtcgt   2640
gctacaagtc ggccaggctg ctgggtggca agtgcgagtt catcctctcc aacagcggtc   2700
acatccagag catcctcaac ccaccgggca accccaaggc acgcttcatg accaatccgg   2760
aactgcccgc cgagcccaag gcctggctgg aacaggccgg caagcacgcc gactcgtggt   2820
ggttgcactg gcagcaatgg ctggccgaac gctccggcaa gaccccgcaag gcgcccgcca   2880 gcctgggcaa caagacctat ccggccggcg aagccgcgcc cggaacctac gtgcatgaac   2940
gatgaaaagc gaccagcctg aagaacagcc gcaggagcga tccgcggcct ccgccgacga   3000
aaccccgcca gcgcctccgg cgcggccccg tgccgcgcgg aagccggcca ggccccgtat   3060
cgccgagccc gcggctgcgc cgccgaggac cccgagcatg cccagccct tcgtcttccg   3120 gaccatcgac ctcgacggcc agaccatccg caccgcagtg cggccgggca aggaaggaag   3180
cactccgctg ctgatcttca acggcatagg cgccaacctg gaactggtgt tcccttcgt   3240 ccaggcgctc gacccggaac tggaggtgat cgccttcgac gttcccggcg tcggcggttc   3300
ctcgacgccc agcgtgccct accgctttcc cggcctggcc aagctggcgg cgcggatgct   3360
cgactacctg gactacggcc aggtcaacgc gatcggcgtg tcctggggcg gcgcgctggc   3420
ccagcagttc gcccacgact atccggaacg ctgcaagaag ctgatcctcg ccgccacttc   3480
ggctggcgcg gtgatggtgc cgggcaagcc gaaggtactg atgcgcatgg ccagcccgcg   3540
gcgctacatc cagccctcct atggcgtaca catcgccccg gacatctacg gcggggcctt   3600
ccgccgcgac cccaagctgg ccatggcgca tgccagcaag gtgcgttcgt cgggcaagct   3660
```

```
gggctactac tggcaactgt tcgccgggct cggctggacc agcatccact ggctgcatag   3720
gatccgccag ccgaccctgg tgctggccgg cgacgacgac ccgatcatcc cgctgatcaa   3780
catgcgtgtg ctggcctggc gcattcccaa cgccgaactg cacgtgatcg acgacggcca   3840
cctgttcctg gtgacccgcg ccgaatcggt ggcgccgatc atcatgaagt tcctcgccga   3900
ggagcgccgt cgcgccgtca tgcaccctcg tccgttcctg cccaagaccg gctgaactgc   3960
tgcacgggca acaccagggc agcagacact gcttcgtcat ggtgcaggtg catagtcaat   4020
gttccgcaac ggcgcatggc gcctggcttc gccgcgacag cgcaagctct gcgacgcccc   4080
tcccggcgtt gtggtacagc gcttgctgcc ccactgtcgg gcggcaacct ccctgttcag   4140
gcaggtgtgc ggttctgccc cgggtgaaac ggaattcaca gctataact  gagtattccg   4200 agccagggga cgatcgcccg tggcatccag actgtggtcc tacgacggag tgtggtccat   4260
gcgagaaaag caggaatcgg gtagcgtgcc ggtgcccgcc gagttcatga gtgcacagag   4320
cgccatcgtc ggcctgcgcg gcaaggacct gctgacgacg tccgcagcc  tggctgtcca   4380 cggcctgcgc cagccgctgc acagtgcgcg gcacctggtc gccttcggag ccagttggg   4440 caaggtgctg ctgggcgaca ccctgcacca gccgaaccca caggacgccc gcttccagga   4500
tccatcctgg cgcctcaatc ccttctaccg gcgcaccctg caggcctacc tggcgtggca   4560
gaaacaactg ctcgcctgga tcgacgaaag caacctggac tgcgacgatc gcgcccgcgc   4620
ccgcttcctc gtcgccttgc tctccgacgc cgtggcaccc agcaacagcc tgatcaatcc   4680
actggcgtta aaggaactgt tcaataccgg cgggatcagc ctgctcaatg cgtccgcca   4740 cctgctcgaa gacctggtgc acaacggcgg catgcccagc caggtgaaca agaccgcctt   4800
cgagatcggt cgcaacctcg ccaccacgca aggcgcggtg gtgttccgca acgaggtgct   4860
ggagctgatc cagtacaagc cgctgggcga gcgccagtac gccaagcccc tgctgatcgt   4920
gccgccgcag atcaacaagt actacatctt cgacctgtcg ccggaaaaga gcttcgtcca   4980
gtacgccctg aagaacaacc tgcaggtctt cgtcatcagt tggcgcaacc ccgacgccca   5040
gcaccgcgaa tggggcctga gcacctatgt cgaggccctc gaccaggcca tcgaggtcag   5100
ccgcgagatc accggcagcc gcagcgtgaa cctggccggc gcctgcgccg cgggctcac   5160 cgtagccgcc ttgctcggcc acctgcaggt gcgccggcaa ctgcgcaagg tcagtagcgt   5220
cacctacctg gtcagcctgc tcgacagcca gatggaaagc ccggcgatgc tcttcgccga   5280
cgagcagacc ctggagagca gcaagcgccg ctcctaccag catggcgtgc tggacgggcg   5340
cgacatggcc aaggtgttcg cctggatgcg ccccaacgac ctgatctgga actactgggt   5400
caacaactac ctgctcggca ggcagccgcc ggcgttcgac atcctctact ggaacaacga   5460
caacacgcgg ctgcccgcgg cgttccacgg cgaactgctc gacctgttca gcacaaccc   5520 gctgacccgc ccgggcgcgc tggaggtcag cgggaccgcg gtggacctgg caaggtggc   5580 gatcgacagc ttccacgtcg ccggcatcac cgaccacatc acgccctggg acgcggtgta   5640
tcgctcggcc ctcctgctgg gcggccagcg ccgcttcatc ctgtccaaca gcgggcacat   5700
ccagagcatc ctcaaccctc ccggaaaccc caaggcctgc tacttcgaga cgacaagct   5760 gagcagcgat ccacgcgcct ggtactacga cgccaagcgc gaagagggca gctggtggcc   5820
ggtctggctg ggctggctgc aggagcgctc gggcgagctg gcaaccctg acttcaacct   5880 tggcagcgcc gcgcatccgc ccctcgaagc ggccccgggc acctacgtgc atatacgctg   5940
aaagatccgg cccgggcgcc tggagccggg cacctccatc cccagaagaa gtccggatga   6000
agacacgcga ccgaatcctc gaatgctcgc tgttgctgtt caacgaacag ggcgagccca   6060
```

-continued

```
acgtctcgac actggagatc gccaacgaac tgggcatcag cccgggcaat ctctactacc    6120
acttccatgg caaggaaccg ctggtgatgg cgctgttcga gcggttccag gccgagttgg    6180
cgccgctgct cgatccgccc gaggaggtgc gcctgggcgc ggaggactac tggctgttcc    6240
tgcacctgat cgtcgagcgc ctcgcccact accgcttcct gttccaggac ctgtccaacc    6300
tgaccgggcg cctgccacgg ctggctcgcg catccgtac ctggctcggc gcgctgaagc    6360
ggaccctggc caccctgctg gcccgcctca aggccgaccg gcagttgcgc agcgacgcgc    6420
cggcactcgg gcaactggtc gaagagatca ccctgaccct gctgttctcc ctggattacc    6480
agcgggtact gggcagcaag ggcgaggtgc gcacggtggt ctaccagatc atgatgctgg    6540 tcgcccccgca tctgcgcagc gaggcccaac gctcggcgga aagcctggcg cagcgctacc    6600
tgggaccgga atgaaaaacg cccggcgagt gccgggcgtg tgccttgccg ccaggactca    6660
gccctggctg ctcggcgtcg ccggagcgtt cgctgccgga gcgctggcag ccggtgtggc    6720
ggcgggggca gcgggcgcgc tcgaagacgc ggcgggagcg gccggtttcg ccgcggcggg    6780
cttggctgcc ggcttcttcg ccgcaggctt tttcgcagcc ggcttggcgg caggtttcgc    6840
cgcgggcttg gcggcggtcg cagcggccgg cttggctgcc ggcttgcgg caggcttggc    6900 tgcggcaggt ttcgcagcag gcttcgccgc ggccttggct gccggcttgg tcgccggttt    6960
cgctgcggcc ttcgcagtcg gttgcggc gggcttggct gccggcttgg cggccgcggt    7020
tttcgccgcg gttttttcg ccgcgggttt cgccgcaggc ttgcggcgg ccttggctgc    7080 cggtttagct gccggcttgg ccgctgcgt tttcgccgcg gcttggcag ccggtttcgc    7140 cgcaggcttg gccgctgcct tcgccgccgg cttgacgctg acgccggtga gtttctcgat    7200
ctgcttggtc agcgtatcga ccttgctgtg cagctccttc acctcgttgc ggctcggcac    7260
gccgagacgc gagatggcgc tgttcaggcg cttgtcgaaa gcttcctcga g            7311
```

<210> SEQ ID NO 11
<211> LENGTH: 5051
<212> TYPE: DNA
<213> ORGANISM: Aeromonas caviae

<400> SEQUENCE: 11

```
gatatccatc agcccctgac agagagcact gatatgaccg gcaggcatcg ccatcccctg     60
ccatcccgcc gcgtactggg tgtgattgga aaactgcacc gtattgacgg gccagacctc    120
catgccgaga cggcgcatgg ggaagacggg ggcgctgttg ccggcacagc cgaaaaccac    180
gtgggactgg atagagagaa tgcgtttcat cgacaccacc actgaagaag catgaggaaa    240
gcgggcaata tatcggatgc atagcgggct ctgccagcga ttcccggcaa ccctcgccat    300
ttatgcggca aaaagcccat tcaatggagt gttacaccaa cttcccccca cgcctgctca    360
acctggcaag ccaagagcgc ctcggccccg tcggtgtgat atgggctctt cacactcttg    420
tttgatggca tatgagggca tttttaatac aaggtggcgg atgcgggag aaagcgtcga    480 ggaagagcaa tgaggcgcgg cggcaggcaa gccggggccg acgccccggg ctttgtactt    540
aaggcttaag gcctgacgaa gtgatagacc cagccttcgt ccaggggaa atcggagggc    600 gcagagacaa gtgccggcag ggaggcgacg gcccctccgg cggcgtattg cagcgccatc    660
agggcgcaga gggcggcgtc gtaacgatcc gtcccggcca ccacatcagg tggcaaggag    720
gcggctatct ccgccctggc cggtgaggcc ttgcctgcta ccttggcaaa gagccgggat    780
agacctccag cacggcgcga tcggcgtggg gctgctgcct cgggcacaag ctgcagatcc    840
```

-continued

```
ccgaggcgcg gcaagatgga gagcgccagg gtggcgttgt tgcctagcct gtcgaaggtg      900
gccgacagcg gcttcttgcc gtattgctgc tgcagccagc gctcgcagtc ccgataggca      960
tagggggttgt ctatctcccg ctggggcacg gcgcactcga ctccctccc cgccagcaga     1020
tcgccgaggg ctcggggaaa ggccaggggg gcatcgatgc cgagcgccag tcgcgggcag     1080
gccagcacct gcatcagcgc catctcgtct tgcagcgccg ggcgcagcaa ggcgtccaga     1140
tccggcgcca cccgggagct caaccgaaac agggggggaga ccccgagcca gtgcaactgc    1200
tgcgtgcggg cctgccagcc caccacggcc accgcctggg cattgccctg ccagcccctt     1260
acatcccaac cgatgccgat ggcatccaag tgttccgttg tcatgcccct gtcacctctg     1320
cgcactattg atggagcaca gggtaatggc tgcgcccctc aaagcaaggc tggcggcacc     1380
gcttagaaag atttcttgaa gttgatcagc ggcaagatgg ggaagatgcc gttctctgcg     1440
tagttggcga gccctatctg caggccatcg aggtgcttgg tggcattgat gaagccaagc     1500
tggaaggtgg tgcgctcggc atagttgacg aagccgaggt tggccagggc attgcccttg     1560
gcgatgttga ccgcccccca gttcagcccc tgcacgttgt tggtcaggtt gacgaaaccc     1620
aggttgaccc cggtgtcctg cccctcatgc cagttgacgg cgttgatggc gaccccgccg     1680
aactgatggc gcacccgggc ggcgccgaag aagatgccaa gctgcaggcc ggtgaactga     1740
tccacgtcgg agagggcgaa caccggcaga tctatgccct tcacctgacc ggtgcggcca     1800
tacaggaagg aggcgcgcgc cccttccacc tggtgggagg aaggcaggtt gatgccgggc     1860
agggagatct ggaccggggt gctggcctgg gccacgccgg cgagggccag cgcggagcaa     1920
ccgagcagca gggcgagagg tttcatcggg attccttggc agtctgaatg acgtgccagc     1980
ctatcagcgc ggcgccggtg cggcgagggc gcgccggacc cagtgcgtca cctctcgtct     2040
gatccgcctc cctcgacggg cgtcgctgac aaaaaaattc aaacagaaat taacatttat    2100
gtcatttaca ccaaaccgca tttggttgca gaatgctcaa acgtgtgttt gaacagagca     2160
agcaacacgt aaacagggat gacatgcagt acccgtaaga agggccgatt ggcccacaac     2220
aacactgttc tgccgaactg gagaccgatg atgaatatgg acgtgatcaa gagctttacc     2280
gagcagatgc aaggcttcgc cgcccccctc acccgctaca accagctgct ggccagcaac     2340
atcgaacagc tgacccggtt gcagctggcc tccgccaacg cctacgccga actgggcctc     2400
aaccagttgc aggccgtgag caaggtgcag gacacccaga gcctggcggc cctgggcaca     2460
gtgcaactgg agaccgccag ccagctctcc cgccagatgc tggatgacat ccagaagctg     2520
agcgccctcg gccagcagtt caaggaagag ctggatgtcc tgaccgcaga cggcatcaag     2580
aaaagcacgg gcaaggcctg ataacccctg gctgcccgtt cgggcagcca catctcccca     2640
tgactcgacg ctacgggcta gttcccgcct cgggtgtggg tgaaggagag cacatgagcc     2700
aaccatctta tggcccgctg ttcgaggccc tggcccacta caatgacaag ctgctggcca     2760
tggccaaggc ccagacagag cgcaccgccc aggcgctgct gcagaccaat ctggacgatc     2820
tgggccaggt gctggagcag ggcagccagc aaccctggca gctgatccag gcccagatga     2880
actggtggca ggatcagctc aagctgatgc agcacaccct gctcaaaagc gcaggccagc     2940
cgagcgagcc ggtgatcacc ccggagcgca gcgatcgccg cttcaaggcc gaggcctgga     3000
gcgaacaacc catctatgac tacctcaagc agtcctacct gctcaccgcc aggcacctgc     3060
tggcctcggt ggatgccctg gagggcgtcc cccagaagag ccgggagcgg ctgcgtttct     3120
tcacccgcca gtacgtcaac gccatggccc ccagcaactt cctggccacc aaccccgagc     3180
tgctcaagct gaccctggag tccgacggcc agaacctggt gcgcggactg gccctcttgg     3240
```

```
ccgaggatct ggagcgcagc gccgatcagc tcaacatccg cctgaccgac gaatccgcct    3300
tcgagctcgg gcgggatctg gccctgaccc cgggccgggt ggtgcagcgc accgagctct    3360
atgagctcat tcagtacagc ccgactaccg agacggtggg caagacacct gtgctgatag    3420
tgccgccctt catcaacaag tactacatca tggacatgcg gccccagaac tccctggtcg    3480
cctggctggt cgcccagggc cagacggtat tcatgatctc ctggcgcaac ccgggcgtgg    3540
cccaggccca aatcgatctc gacgactacg tggtggatgg cgtcatcgcc gccctggacg    3600
gcgtggaggc ggccaccggc gagcgggagg tgcacggcat cggctactgc atcggcggca    3660
ccgccctgtc gctcgccatg ggctggctgg cggcgcggcg ccagaagcag cgggtgcgca    3720
ccgccaccct gttcactacc ctgctggact tctcccagcc cggggagctt ggcatcttca    3780
tccacgagcc catcatagcg gcgctcgagg cgcaaaatga ggccaagggc atcatggacg    3840 gcgccagct ggcggtctcc ttcagcctgc tgcgggagaa cagcctctac tggaactact    3900
acatcgacag ctacctcaag ggtcagagcc cggtggcctt cgatctgctg cactggaaca    3960
gcgacagcac caatgtggcg ggcaagaccc acaacagcct gctgcgccgt ctctacctgg    4020
agaaccagct ggtgaagggg gagctcaaga tccgcaacac ccgcatcgat ctcggcaagg    4080
tgaagacccc tgtgctgctg gtgtcggcg tggacgatca catcgccctc tggcagggca    4140
cctggcaggg catgaagctg tttggcgggg agcagcgctt cctcctggcg gagtccggcc    4200
acatcgccgg catcatcaac ccgccggccg ccaacaagta cggcttctgg cacaacgggg    4260
ccgaggccga gagcccggag agctggctgg caggggcgac gcaccagggc ggctcctggt    4320
ggcccgagat gatgggcttt atccagaacc gtgacgaagg gtcagagccc gtccccgcgc    4380
gggtcccgga ggaagggctg gccccgccc cggccacta tgtcaaggtg cggctcaacc    4440
ccgtgtttgc ctgcccaaca gaggaggacg ccgcatgagc gcacaatccc tggaagtagg    4500
ccagaaggcc cgtctcagca gcggttcgg ggcggcggag gtagccgcct cgccgcgct    4560 ctcggaggac ttcaaccccc tgcacctgga cccggccttc gccgccacca cggcgttcga    4620
gcggcccata gtccacggca tgctgctcgc cagcctcttc tccgggctgc tgggccagca    4680
gttgccgggc aaggggagca tctatctggg tcaaagcctc agcttcaagc tgccggtctt    4740
tgtcggggac gaggtgacgg ccgaggtgga ggtgaccgcc cttcgcgagg acaagcccat    4800
cgccaccctg accacccgca tcttcaccca aggcggcgcc ctcgccgtga cgggggaagc    4860
cgtggtcaag ctgccttaag caccggcggc acgcaggcac aatcagcccg ccccctgccg    4920
ggctgattgt tctccccgc tccgcttgcc ccctttttcg gggcaattg gcccaggccc    4980 tttccctgcc ccgcctaact gcctaaaatg gccgccctgc cgtgtaggca ttcatccagc    5040
tagaggaatt c                                                         5051
```

<210> SEQ ID NO 12
<211> LENGTH: 2849
<212> TYPE: DNA
<213> ORGANISM: Thiococcus pfennigii

<400> SEQUENCE: 12

```
ggatcctggt cgcgagcgcg ccgcccagcc acctgccggc gcgccccgcc gggaccgctc      60
gaggacgcct cgcgaaggct ctaggggctg tatcttcaag agtctacgcc cctttgttgc     120
agtgcacaaa tttccgtgct agcttcatgc tatcacgccc cagacgagga agattcaccg     180
tgaacgatac ggccaacaag accagcgact ggctggacat ccaacgcaag tactgggaga     240
```

-continued

```
cctggtcgga gctcggccgc aagaccttgg gtctggagaa gaccccggcc aatccttggg     300
ccggcgccct cgatcattgg tggcagacgg tctcgcccgc cgcccccaac gacctggttc     360
gcgacttcat ggagaagctc gccgagcagg gcaaggcctt cttcggcctc accgactact     420
tcacgaaggg cctcggcggc agtagcggta cgcagggctg ggacaccctc tcgaagacca     480
tcgacgacat gcaaaaggcc ttcgccagcg gccggatcga aggcgacgag accttccgcc     540
gcctgatggc cttctgggag atgccgctcg acaactggca gcgcaccatg tcctcgctgt     600
ccccggtgcc cggcgacctg ctgcgcaaca tgccgcacga ccaagtcagg gacagcgtcg     660
accgcatcct ctcggcaccc gggctcggct acacgcgcga ggagcaggcc cgctaccagg     720
atctgatccg ccgctcgctg gagtaccagt cggccctgaa cgaatacaac ggcttcttcg     780
gccagctcgg tgtcaagtcc ctcgagcgga tgcgcgcctt cctgcaggga caggccgaga     840
agggcgtcgc catcgagtcg gcgcgcaccc tctacgacgc ctgggtcggc tgctgcgaag     900
aggtctatgc cgaggaggtc agctccgccg actacgcgca catccacggc cgcctcgtca     960
acgcccagat ggccctcaag cagcgcatgt cgaccatggt cgacgaggtc ctcggcgcga    1020
tgccgctgcc gacccgcagc gagctgcgca cgctccagga tcggctccag gagtcgcgcg    1080
gcgagggcaa cgccagcgc caagagatcg agacgctgaa gcggcaggtc gcggccttgg    1140
ccggcggcgc ccagcccgcg ccccaggcct ccgcccagcc cagcacccgg cccgcgccgg    1200
cgacggcccc ggcggcgagc gcggcgccca agcgcagcac cacgacccgc cgcaagacca    1260
ccaagcccac caccggccag tgatgtcggc cgcccgtcca tcgccaccag gagagagtgc    1320
cgtgtcccca ttcccgatcg acatccggcc cgacaagctg accgaggaga tgctggagta    1380
cagccgcaag ctcggcgagg gtatgcagaa cctgctcaag gccgaccaga tcgacacagg    1440
cgtcaccccc aaggacgtcg tccaccgcga ggacaagctg gtcctctacc gctaccggcg    1500
cccggcgcag gtggcgaccc agacgatccc gctgctgatc gtctacgccc tcgtcaatcg    1560
gccctacatg accgacatcc aggaggatcg ctcgacgatc aagggcctgc tcgccaccgg    1620
tcaggacgtc tatctgatcg actggggcta cccggatcag gccgaccggg cgctgaccct    1680
cgatgactac atcaacggct acatcgaccg ctgcgtcgac tacctgcgcg agacccacgg    1740
cgtcgaccag gtcaacctgc tcgggatctg ccagggcggg gccttcagcc tctgctacac    1800
ggccctgcac tccgagaagg tcaaaaacct cgtcaccatg gtcacgccgg tcgacttcca    1860
gaccccgggc aacctgctct cggcctgggt ccagaacgtc gacgtcgacc tggccgtcga    1920
caccatgggc aacatcccgg gcgaactgct caactggacc ttcctgtcgc tcaagcccu    1980 cagcctgacc ggccagaagt acgtcaacat ggtcgacctg ctcgacgacg aggacaaggt    2040
caagaacttc ctgcggatgg agaagtggat cttcgacagc ccggaccagg ccggcgagac    2100
cttccgccag ttcatcaagg acttctacca gcgcaacggc ttcatcaacg gcggcgtcct    2160
gatcggcgat caggaggtcg acctgcgcaa catccgctgc ccggtcctga acatctaccc    2220
gatgcaggac cacctggtgc cgccggatgc ctccaaggcc ctcgcgggac tgacctccag    2280
cgaggactac acgagctcg ccttcccggg cgggcacatc ggcatctacg tcagcggcaa    2340
ggcgcaggaa ggagtcaccc cggcgatcgg ccgctggctg aacgaacgcg gctgagccgg    2400
gtcgacccac ccgctcgacg ggcgcggccg cggcatcga aggccgccgg ccggcgccca    2460
tgagccatcc gcgccgctgg cgccgccccc ccgaccttcg ccgccgcacc cgcatcgccc    2520
ccgcggctgg cgtacaatga cggtcttcgc gagcgagccc cgcatcgtca acggaggctg    2580
catgggcgcc gaccaccaac tgctggccgc gtacgacgcg ctggccgaga cctacgacgc    2640
```

```
ccaccgcggc tcttcgaca tgcgcgccgt gctcgaggac atcttcgccc gcctgccggc    2700
ctgcggcacc tcctcgacc tcggctgcgg cgccggggag ccgtgcgcgc gcgccttcct    2760
cgaccgcggc tggcgggtga ccggggtgga cttctgcccg gccatgctcg ccctcgcggc    2820
gcgctacgtc cccgagatgg agcggatcc                                      2849

<210> SEQ ID NO 13
<211> LENGTH: 2768
<212> TYPE: DNA
<213> ORGANISM: Ralstonia eutropha

<400> SEQUENCE: 13
cccgggcaag taccttgccg acatctatgc gctggcgcgc acgcgcctgg cgcgcgccgg      60
ctgtaccgag gtctacggcg gcgacgcctg caccgtggcc gacgccggtc gcttctactc     120
ctatcggcgc gatggcgtga ccggccgcat ggccagcctg gtctggctgg cggactgagc     180
ccgccgctgc ctcactcgtc cttgcccctg gccgcctgcg cgcgctcggc ttcagccttg     240
cgtcggcggc ggccgggcgt gcccatgatg tagagcacca cgccaccggc gccatgccat     300
acatcaggaa ggtggcaacg cctgccacca cgttgtgctc ggtgatcgcc atcatcagcg     360
ccacgtagag ccagccaatg ccacgatgt  atcaaaaa  ttcatccttc tcgcctatgc     420 tctgggcct  cggcagatgc gagcgctgca taccgtccgg taggtcggga agcgtgcagt     480
gccgaggcgg attcccgcat tgacagcgcg tgcgttgcaa ggcaacaatg gactcaaatg     540
tctcggaatc gctgacgatt cccaggtttc tccggcaagc atagcgcatg gcgtctccat     600
gcgagaatgt cgcgcttgcc ggataaaagg ggagccgcta tcggaatgga cgcaagccac     660
ggccgcagca ggtgcggtcg agggcttcca gccagttcca gggcagatgt gccggcagac     720
cctcccgctt tggggaggc  gcaagccggg tccattcgga tagcatctcc ccatgcaaag     780
tgccggccag ggcaatgccc ggagccggtt cgaatagtga cggcagagag acaatcaaat     840
catggcgacc ggcaaaggcg cggcagcttc cacgcaggaa ggcaagtccc aaccattcaa     900
ggtcacgccg gggccattcg atccagccac atggctggaa tggtcccgcc agtggcaggg     960
cactgaaggc aacggccacg cggccgcgtc cggcattccg ggcctggatg cgctggcagg    1020
cgtcaagatc gcgccggcgc agctgggtga tatccagcag cgctacatga aggacttctc    1080
agcgctgtgg caggccatgg ccgagggcaa ggccgaggcc accggtccgc tgcacgaccg    1140
gcgcttcgcc ggcgacgcat ggcgcaccaa cctcccatat cgcttcgctg ccgcgttcta    1200
cctgctcaat gcgcgcgcct tgaccgagct ggccgatgcc gtcgaggccg atgccaagac    1260
ccgccagcgc atccgcttcg cgatctcgca atgggtcgat gcgatgtcgc ccgccaactt    1320
ccttgccacc aatcccgagg cgcagcgcct gctgatcgag tcgggcggcg aatcgctgcg    1380
tgccggcgtg cgcaacatga tggaagacct gacacgcggc aagatctcgc agaccgacga    1440
gagcgcgttt gaggtcggcc gcaatgtcgc ggtgaccgaa ggcgccgtgg tcttcgagaa    1500
cgagtacttc cagctgttgc agtacaagcc gctgaccgac aaggtgcacg cgcgcccgct    1560
gctgatggtg ccgccgtgca tcaacaagta ctacatcctg gacctgcagc cggagagctc    1620
gctggtgcgc catgtggtgg agcagggaca tacggtgttt ctggtgtcgt ggcgcaatcc    1680
ggacgccagc atggccggca gcacctggga cgactacatc gagcacgcgg ccatccgcgc    1740
catcgaagtc gcgcgcgaca tcagcggcca ggacaagatc aacgtgctcg gcttctgcgt    1800
gggcggcacc attgtctcga ccgcgctggc ggtgctggcc gcgcgcggcg agcacccggc    1860
```

```
cgccagcgtc acgctgctga ccacgctgct ggactttgcc gacacgggca tcctcgacgt   1920
ctttgtcgac gagggccatg tgcagttgcg cgaggccacg ctgggcggcg cgccggcgc    1980 gccgtgcgcg ctgctgcgcg ccttgagct ggccaatacc ttctcgttct tgcgcccgaa    2040
cgacctggtg tggaactacg tggtcgacaa ctacctgaag ggcaacacgc cggtgccgtt   2100
cgacctgctg ttctggaacg cgacgccac caacctgccg gggccgtggt actgctggta   2160
cctgcgccac acctacctgc agaacgagct caaggtaccg ggcaagctga ccgtgtgcgg   2220
cgtgccggtg gacctggcca gcatcgacgt gccgacctat atctacggct cgcgcgaaga   2280
ccatatcgtg ccgtggaccg cggcctatgc ctcgaccgcg ctgctggcga caagctgcg    2340 cttcgtgctg ggtgcgtcgg gccatatcgc cggtgtgatc aacccgccgg ccaagaacaa   2400
gcgcagccac tggactaacg atgcgctgcc ggagtcgccg cagcaatggc tggccggcgc   2460
catcgagcat cacggcagct ggtggccgga ctggaccgca tggctggccg gcaggccgg    2520 cgcgaaacgc gccgcgcccg ccaactatgg caatgcgcgc tatcgcgcaa tcgaacccgc   2580
gcctgggcga tacgtcaaag ccaaggcatg acgcttgcat gagtgccggc gtgcgtcatg   2640
cacggcgccg gcaggcctgc aggttccctc ccgtttccat tgaaaggact acacaatgac   2700
tgacgttgtc atcgtatccg ccgccgcac cgcggtcggc aagtttggcg gctcgctggc   2760
caagatcc                                                             2768

<210> SEQ ID NO 14
<211> LENGTH: 1980
<212> TYPE: DNA
<213> ORGANISM: Acinetobacter sp.

<400> SEQUENCE: 14
ctgaattcaa atcggaattt gaaaagttag ttagcgaatc tatgcctaac aataaataac     60
actgctctga aaaccatgcg ttatcaggac gaatgttacg gggaagtgtg aaaatttccc    120
cgttttagtt tcagccctgc actcaatttg attgctaaaa gccatgtgct atggagcgat    180
gaaatgaacc cgaactcatt tcaattcaaa gaaaacatac tacaatttttt ttctgtacat    240 gatgacatct ggaaaaaatt acaagaattt tattatgggc aaagcccaat taatgaggct    300
ttggcgcagc tcaacaaaga agatatgtct ttgttctttg aagcactatc taaaaaccca    360
gctcgcatga tggaaatgca atggagctgg tggcaaggtc aaatacaaat ctaccaaaat    420
gtgttgatgc gcagcgtggc caaagatgta gcaccattta ttcagcctga agtggtgat    480 cgtcgtttta acagcccatt atggcaagaa cacccaaatt ttgacttgtt gtcacagtct    540
tatttactgt ttagccagtt agtgcaaaac atggtagatg tggtcgaagg tgttccagac    600
aaagttcgct atcgtattca cttctttacc cgccaaatga tcaatgcgtt atctccaagt    660
aactttctgt ggactaaccc agaagtgatt cagcaaactg tagctgaaca aggtgaaaac    720
ttagtccgtg gcatgcaagt tttccatgat gatgtcatga atagcggcaa gtattatct   780 attcgcatgg tgaatagcga ctctttcagc ttgggcaaag atttagctta caccctggt    840 gcagtcgtct ttgaaaatga catttttcaa ttattgcaat atgaagcaac tactgaaaat    900
gtgtatcaaa cccctattct agtcgtacca ccgtttatca ataaatatta tgtgctggat    960
ttacgcgaac aaaactcttt agtgaactgg ttgcgccagc aaggtcatac agtcttttta   1020
atgtcatggc gtaacccaaa tgccgaacag aaagaattga cttttgccga tctcattaca   1080
caaggttcag tggaagcttt gcgtgtaatt gaagaaatta ccggtgaaaa agaggccaac   1140
tgcattggct actgtattgg tggtacgtta cttgctgcga ctcaagccta ttacgtggca   1200
```

-continued

| | |
|---|---|
| aaacgcctga aaaatcacgt aaagtctgcg acctatatgg ccaccattat cgactttgaa | 1260 |
| aacccaggca gcttaggtgt atttattaat gaacctgtag tgagcggttt agaaaacctg | 1320 |
| aacaatcaat tgggttattt cgatggtcgt cagttggcag ttaccttcag tttactgcgt | 1380 |
| gaaaatacgc tgtactggaa ttactacatc gacaactact taaaaggtaa agaaccttct | 1440 |
| gattttgata ttttatattg gaacagcgat ggtacgaata tccctgccaa aattcataat | 1500 |
| ttcttattgc gcaatttgta tttgaacaat gaattgattt caccaaatgc cgttaaggtt | 1560 |
| aacggtgtgg gcttgaatct atctcgtgta aaaacaccaa gcttctttat tgcgacgcag | 1620 |
| gaagaccata tcgcactttg ggatacttgt ttccgtggcg cagattactt gggtggtgaa | 1680 |
| tcaaccttgg ttttaggtga atctggacac gtagcaggta ttgtcaatcc tccaagccgt | 1740 |
| aataaatacg gttgctacac caatgctgcc aagtttgaaa ataccaaaca atggctagat | 1800 |
| ggcgcagaat atcaccctga atcttggtgg ttgcgctggc aggcatgggt cacaccgtac | 1860 |
| actggtgaac aagtccctgc cgcaacttg gtaatgcgc agtatccaag cattgaagcg | 1920 |
| gcaccgggtc gctatgtttt ggtaaattta ttctaatcgg tcatataaca acagccatgc | 1980 |

<210> SEQ ID NO 15
<211> LENGTH: 4936
<212> TYPE: DNA
<213> ORGANISM: Alcaligenes latus

<400> SEQUENCE: 15

| | |
|---|---|
| ggttcttctc gttccggcgg gaccgggtca cggggcggca ggctgccgcc gtctggctgc | 60 |
| gcggatgaag cggtgtcctc ggcgcgcttg cgcgcccgtc gccgcgccgg cgtccccagg | 120 |
| aagtacagga cgatggacaa gggcagtacg ccatacagca gcagcgtgaa caccgcgccg | 180 |
| agcaaggtgc cgttgggcgc catggcttcg gccacggcca tcatcagcac cacgtacagc | 240 |
| catgccagag caaccaagta catagcaaaa acccgcaatt acgcagaatg acgtatttcg | 300 |
| tacaatgaaa actgttgtca tgatgcggta agacacgaag cctacaacgc gatccagcaa | 360 |
| cggttttcgt gaaaaagtcc tcaggagacg agcgtgacac tgcatcccat tcccgcactg | 420 |
| caacagcttg gcgacaacgc cacggcgctg agtgccgcca tctcggaagc gctgcgcgcg | 480 |
| atgtcgggcc tgaacctgcc gatgcaggcc atgaccaagc tgcagggcga gtacctcaac | 540 |
| gaggcgacgg cgctgtggaa ccagacgctg gccgcctgc agcccgacgg cagcgcccaa | 600 |
| ccggccaagc tgggcgaccg cgcttctcg gccgaggact gggccaagaa ccccgccgcg | 660 |
| gcctacctgg cgcaggtcta cctgctcaat gcccgcacgc tgatgcagat ggccgagtcc | 720 |
| atcgagggcg acgccaaggc caaggcgcgc gtgcgcttcg ccgtgcagca gtggatcgac | 780 |
| gccgcggcgc cgagcaactt cctggcgctc aatcccgagg cgcagcgcaa ggcgctggag | 840 |
| accaagggg agagcatcag ccagggcctg cagcagctgt ggcatgacat ccagcagggc | 900 |
| cacgtgtcgc agacggacga gagcgtgttc gaggtgggca agaacgtcgc caccaccgag | 960 |
| ggcgcggtcg tgtacgagaa cgacctgttc cagctcatcg agtacaagcc gctgacgccc | 1020 |
| aaggtgcacg agaagccgat gctgttcgtg ccgccgtgca tcaacaagta ctacatcctg | 1080 |
| gacctgcagc cggacaacag cctcatccgc tacaccgtcg cccagggcca ccgggtgttc | 1140 |
| gtggtgagct ggcgcaaccc cgacgcctcc gtcgccggca agacctggga cgactacgtg | 1200 |
| gagcagggcg tgatccgcgc catccgcgtg atgcagcaga tcacgggca cgagaaggtc | 1260 |
| aacgcgctgg gcttctgcgt cggcggcacc atcctgagca cggcgctggc ggtgctggcc | 1320 |

-continued

```
gcgcgcggcg agcagcccgc ggcgagcctg acgctgctga ccacgctgct ggacttcagc    1380
aacaccggcg tgctggacct gttcatcgac gaggccggcg tgcgcctgcg cgagatgacc    1440
atcggcgaga aggcgcccaa cggcccgggc ctgctcaacg caaggagct ggccaccacc     1500 ttcagcttcc tgcgcccgaa cgacctggtc tggaactacg tggtgggcaa ctacctcaag    1560
ggcgaggcgc cgccgccctt cgacctgctg tactggaact ccgacagcac caacatggcc    1620
gggcccatgt tctgctggta cctgcgcaac acctacctgg agaacaagtt gcgcgttccc    1680
ggtgccctga ccatctgcgg cgagaaggtg gacctctcgc gcatcgaggc gccggtgtac    1740
ttctacggtt cgcgcgagga ccacatcgtg ccctgggaat cggcctacgc cggcacgcag    1800
atgctgagcg gccccaagcg ctatgtcctg ggtgcgtctg gccacatcgc cggcgtgatc    1860
aaccccccgc agaagaagaa gcgcagctac tggaccaacg agcagctcga cggcgacttc    1920
aaccagtggc tggaaggctc caccgagcat cctggcagct ggtggaccga ctggagcgac    1980
tggctcaagc agcacgcggg caaggaaatc gccgcaccca agactcccgg caacaagacc    2040
cacaagccca tcgagcccgc ccccgggcgt tacgtgaagc agaaggcctg agccgcggcc    2100
cctgagcctt ctttaacccg accttgacaa acgaggagat aagcatgacc gacatcgtca    2160
tcgtcgccgc agcccgcacc gccgtgggca agttcggcgg cacgctggcc aagacccccg    2220
ctccggagct gggcgccgtg gtcatcaagg ccctgctgga agacggggc gtcaagcccg    2280 accagatcgg tgaagtcatc atgggccagg tgctggccgc cggcgcgggc cagaaccccg    2340
cgcgccaggc gatgatgaag gcgggcatcg ccaaggaaac gccggcgctg accatcaacg    2400
ccgtgtgcgg ctccggcctc aaggccgtga tgctggccgc ccaggccatc gcctggggcg    2460
acagcgacat cgtcatcgcc ggcggccagg agaacatgag cgccagcccg cacgtgctga    2520
tgggcagccg cgacggccag cgcatgggcg actggaagat ggtcgacacc atgatcaacg    2580
acggcctgtg ggacgtgtac aacaagtacc acatgggcat cacggccgag aacgtcgcca    2640
aggaacacga catcagccgc gaccagcagg acgccctggc cctggccagc cagcagaagg    2700
ccaccgccgc gcaggaagcc ggccgcttca aggacgagat cgttccggtc tcgatcccgc    2760
agcgcaaggg cgacccggtg ctgttcgaca ccgacgagtt catcaacaag aagaccaccg    2820
ccgaagcgct ggcgggcctg cgcccggcct tcgacaaggc cggcagcgtg accgcgggca    2880
acgcctcggg catcaacgac ggcgccgctg cggtgatggt gatgtccgcc gccaaggcga    2940
aggagctggg cctgacgccc atggcgcgca tcaagagctt cggcaccagc ggcctggatc    3000
cggccaccat gggcatgggc ccggtgccgg cctcgcgcaa ggcgctggag cgcgccggct    3060
ggcaggtcgg tgacgtggac ctgttcgagc tcaacgaagc cttcgccgcc caggcctgcg    3120
cggtgaacaa ggagctgggc gtggatccgg ccaaggtcaa cgtcaacggc ggtgccatcg    3180
ccatcggcca ccccatcggc gcctccggct gccgcgtgct ggtgacgctg ctgcacgaga    3240
tgcagcgccc ggacgccaag aagggcctgg ccgcgctgtg catcggcggc ggcatgggcg    3300
tgtcgctgac cgtcgagcgc tgatcagaag aaccgggcgg ccccgcgccg cccgcccggc    3360
gttccacgcg ggtgcgccgg ataccagac gaaccaaacc accaagggct tcgagacggg    3420
ccgaagaagg agagacagat ggcacagaaa ctggcttacg tgaccggcgg catgggcggc    3480
atcggcacct cgatgtgcca cgcgctgcac aaggacggct tcaaggtgat cgccggctgc    3540
ggtccgagcc gcgaccacca gaagtggatc gatgaacagg ccgcgctggg ctataccttc    3600
tacgcctccg tgggcaacgt ggccgactgg gactccaccg tggccgcctt cgagaaggtc    3660
aaggccgagc acggcaccgt ggacgtgctg gtgaacaacg ccggcatcac gcgtgacggg    3720
```

-continued

```
cagttccgca agatgagcaa ggccgattgg caggccgtga tgtcgaccaa cctcgacagc      3780
atgttcaacg tcaccaagca ggtgatcgag ggcatgctgg acaagggctg gggccggatc      3840
atcaacatct cctcggtcaa cggcgagaag ggccagttcg ccagaccaa ctactccgcc       3900 gccaaggccg gcatgcacgg cttctcgatg gcgctggcgc aggaagtggc ggccaagggc      3960
gtgacggtga acaccgtgag cccgggctac atcgccacgg acatggtcaa ggccatccgc      4020
caggacgtgc tggacaagat catcgccacc attcccatcc gtcgcctggg tacgccggag      4080
gagatcgcct ccatcgtcgc ctggctggcc ggcgaggagt cgggcttcac caccggtgcc      4140
gacttcagct gcaacggcgg cctgcacatg ggctgaggcc cgcggctcca tgcccacctg      4200
cgtgggcatg gacgggccga aggacccgag ctctgcgagg gtgcggcctg caaggctgag      4260
gcctgctgcg ccgcgtgccc gcgagggcac gtgccgaagc accaaaaggc cgcgcattgc      4320
gcggcctttt cctttctgga tcggtgcgga cgggtgccgc gtcaggcagg cagggcccc       4380 cgggccttca ctccaccatg cccgacatga agtacttgat cagcccttg ccgcgaagc        4440 ccagcatgcc gaagcccagc gccaggaaca gcacgaaggt gccgaacttg ccggccttcg      4500
actcgcgcgc gagctgaaag atgatgaatg ccatgtagag catgaaggcc gtgacgccga      4560
cggtcaggcc cagctgggca atgttttcct cgttgatttc gaacatcgtt tgttgtctca      4620
ggctgctgca cgcggctgac gtgctcgccg cgcggccggg ccccaactgc ccgcagcggt      4680
tctcgatcag gttctcaagg catctcgtgc cactgggagg tgtccaccag gtcgcggtag      4740
gcgtgccagc tcgaatgcgc cagccacggc actaccacga tcaggcccag cagcagcgtg      4800
gccatgccca gcagcgtcag cgccatgatc agcgccgccc acagcgccag cggcagtggg      4860
tgctgcatca ccacgcgcca gctcgtgagc accgccacca gcacgcccac gtggcggtcc      4920
agcagcatcg ggatcc                                                    4936
```

<210> SEQ ID NO 16
<211> LENGTH: 1752
<212> TYPE: DNA
<213> ORGANISM: Azorhizobium caulinodans

<400> SEQUENCE: 16

```
atggaggcgt tcgcccagaa ccttgcgaag atggtggagg aaggcggcaa ggccgtcgcc       60
gcttacatgc gtccgcgcga ggagggcaag ccggacgaca tgacggacga tatcgccgat      120
gcgctcaaga ccatcggcga ggtggccaat tactggatgt ccgatccaaa gcgctccttc      180
gaggcccagt cgcgcctcat gatgggctac atgggcgtct gggcggggc gctccagaag       240 ctctccggcg agaaggccga gcccatcgcg aaggccgacc ccaaggacgg ccgcttcaag      300
gacccggaat gggaaagccc gttcttcgac gccctgaagc agacctatct cgtgaccagc      360
aactgggccg agtccatggt caaggaggcc gaggggctcg atccccacac caagcacaag      420
gccgaattcc tggtgcgcca gctctcgaat gcggtggcgc cctcgaactt cctcatgacc      480
aacccggagc tgatccgcga aacgctctcc tccagcggcg agaacctcgt gcgcggcatg      540
aagaatctgg ccgaggatct ggtggagggc aaaggcgatc tcaagatccg ccagacggac      600
atgagcgcct cgaggtggg ccgcaatctg gcgctcagcc ccgcaaggt catcttcgag        660 accgagctga tgcagctcat ccagtatgcg ccctcgacgc ccagcgtgaa gaagacgccg      720
gtgctgatcg tgccgccctg gatcaacaag ttctacatcc tcgacctgac gcccgagaaa     780
tccctcatca agtggatggt ggatcagggg ctgacggtct tcgtcatctc gtgggtcaat      840
```

```
ccggacgccc gtctcgccga caagggcttc gacgactaca tgcgcgatgg catcttcgcc      900
gcgctcgatg cggtggagaa ggcgaccggc gagcatcagg cgcacaccat cggctattgc      960
gtgggcggca cgctgctcgc ggtcacgctt gcctacatgg cggcgaccgg cgatgaccgg     1020
gtggcgagct ccaccttcct caccacccag atcgacttca cccacgcggg cgatctcaag     1080
gtcttcgtgg acgaggcgca gctctcggtc atcgagcgtc gcatgaagga gatgggctat     1140
cttgaaggac gcaagatggc cgacgccttc aacatgctgc ggtccaacga cctgatctgg     1200
ccctatgtgg tgaacaatta tctcaagggg aagcagccgt tccccttcga tcttctgttc     1260
tggaatgccg attccacccg catgccggcg gcgaaccact cctattacct gcgcaactgc     1320
tatctccaga caacatcgc caaggggctg gcggagatcg cgggcgtcaa gatcgacatg     1380
ggcaaggtga cgatcccggt ctattcgctc gccacccgcg aggaccatat cgcgccgccc     1440
aactccgctt atatcggtgc aggcctgctc ggcggccccg tgcgcttcgt gctggccggg     1500
tccggccata ttgcgggcgt ggtcaatccg ccggtgaagc acaagtacca gtactggacc     1560
ggcggtccga ccggcgggga ctatgacgtc tggctgaagg gggcgcagga gcacaagggc     1620
tcgtggtggc cggattgggc gcagtggttc agcgccctgc atccggacga ggtccctgcc     1680
cgcgagccag gcggcagcgc gttcaatccc atcgaggatg cccccggccg ctacgtacgc     1740
gagaagtcct ga                                                         1752

<210> SEQ ID NO 17
<211> LENGTH: 3973
<212> TYPE: DNA
<213> ORGANISM: Comamonas acidovorans

<400> SEQUENCE: 17
cccgggcaag cggcgcagca gaccctggcc tggctgggac cctgcatcgg tccgcgctcc       60
ttcgaagtgg gagccgaggt gcgcgcggcc ttcatcgcgc atgacgcggc ggccggggcg      120
catttcaccg ccgtggcgca agagggcggg ggcgcaccca agtacctggc caacctggcc      180
gggcttgcgc gccagcgcct ggcggcgctg gcatcaccg ccatctacgg caatgacggc      240
ggcgacgcat ggtgcacggt gctcaacggc tcacggttct tttcgcaccg gcgcgacgct      300
gcccgcctcg gcagcagcgg gcggttcgcc gcctgcatct ggaaggactg agcgcgcctg      360
cgtgccgggg ccgttttgcg aggcctgctg ctgcgcgagc caggcctcgc gctcggccaa      420
ttcgcgtgca tggcgttttc gcttgcgcgc gggcgtgccc atgatgtaga tcacgatcga      480
cagcggcagc agtccgtaga gtgcgaacgt gatcacggcg ccgagtatgc tgcccgtggg      540
gctggcggcc tcggccactg ccatcatcag agtgacatac agccaggcga taacaacgag      600
atacatggtc gaaccaaaaa aacgagcggg gcacgggttt tcgtggaggt ctgtgccggg      660
caaggcgggg ctcgcctggg tcacaatcaa acggatgcc ccgcaagccc caggctattg      720
catggcatcc acgaacaagg atgcagcatg aattttgacc cactcgctgg cctgtcaggc      780
caatccgtcc agcaattctg gaacgagcaa tggagccgca cgctgcagac actgcagcag      840
atggggcaac caggccttcc gggaatccag ggcatgccag gcatgccgga catggcccag      900
gcctggaaag cggccgtccc cgaacccggc gccctgcccg agaacgcgct gtcgctggac      960
cccgaaaagc tgctggagct gcagcgccag tacctggatg cgccaaggc catggccgaa     1020
cagggcggcg cccaggcgct gctggccaag gacaagcgct tcaataccga atcgtgggcc     1080
ggcaaccccgc tgacgcggc cacggccgcc acctatctgc tcaacagccg catgctcatg     1140
ggcctggccg atgccgtgca ggccgatgac aagacgcgca accgcgtgcg cttcgccatc     1200
```

-continued

```
gagcaatggc tggcggccat ggcgcccagc aacttcctgg cactcaatgc cgaggcccag    1260
aagaaggcca tcgaaaccca gggcgagagc ctggcccagg gcgtggccaa cctgctggcc    1320
gacatgcgcc agggccatgt gtccatgacc gacgagagcc tgttcaccgt gggcaagaac    1380
gtcgccacca ccgaaggcgc cgtggtgttc gagaacgagc tgttccagct catcgaatac    1440
aagccgctga cggacaaggt gcacgagcgg cccttcctca tggtgccgcc ctgcatcaac    1500
aagttctaca tcctggacct gcagcctgac aactcgctga tccgctacgc cgtcagccag    1560
ggccatcgca ccttcgtgat gagctggcgc aaccccgacg aaagcctggc gcgcaagacc    1620
tgggacaact acatcgagga cggcgtgctc accggcatcc gcgtggcgcg cgagatcgcg    1680
ggagccgagc agatcaatgt gctgggcttt tgcgtgggcg gcaccatgct gtccaccgcg    1740
ctggcggtgc tgcaggcacg ccacgaccgc gagcatggcg cagttgctgc tccggcggcc    1800
aaggcgcctg cggccaagcg cgcggctggc agccgcagcg ccgcccgcac atccacagcc    1860
cgcgccacgg cgccggccgg cgtgccgttt cccgtggcca gcgtcacgct gctgaccacc    1920
ttcatcgact tcagcgacac cggcatcctc gatgtcttca tcgacgaatc cgtggtgcgc    1980
ttccgcgaga tgcagatggg cgagggcggc ctcatgaagg ccaggacct ggcgtccacc    2040 ttcagctttc tgcggcccaa cgacctggtc tggaactacg tggtgggcaa ctacctcaag    2100
ggcgagacgc ccccgccgtt cgacctgctg tactggaaca cgactccac caacctgccc    2160 ggcccctact acgcctggta cctgcgcaac ctctacctgg aaaacaggct ggcccagccc    2220
ggcgcgctga ccgtctgcgg cgagcgcatc gacatgcacc agctgcgcct gccggcctat    2280
atctacggct cgcgcgagga ccacatcgtg cccgtgggcg ctcctatgc gtccacccag    2340 gtgctgggcg cgacaagcg ttttgtgatg ggcgcgtcgg gccacatcgc gggcgtgatc    2400
aatccgccgg ccaagaaaaa gcgcagctac tggctgcgcg aggacggcca gctgcccgcc    2460
acgctcaagg agtggcaggc cggcgccgac gagtacccgg gcagctggtg ggccgactgg    2520
agcccctggc tggccgagca cggcggcaag ctggtcgcgg cgccaaagca gtacggcaag    2580
ggcagggaat acacggccat cgagccggcc ccgggccgct acgtactggt caaggcctga    2640
ggcacaatcg tttcgatgct gcagcgcaat aacgcttcgg cttgaatgca gggtgccgct    2700
gccgcgactg cggccgcgtg cgcccaggca tcccttcaag agtccaaaga aggtccgtc    2760 atcatggaag acatcgtcat cgtttccgct gtccgtactg ccgttggcaa gtttggcggc    2820
acccttgcca agatccccgc caccgaactg ggctccatcg tgatccgcga ggcactgaac    2880
cgtgccaagg tcggcaccga tcaggtcggt gaagtcatca tgggccaggt gctggccgct    2940
ggcgcaggcc agaaccccgc acgccaggcc atgatgaagg ccggcgttgc caaggaaacc    3000
ccggccctca ccatcaacgc cgtctgcggc tcgggcctga aggccgtgat gctggcagcc    3060
caggccgtgg ccacgggcga cagcgagatc gtcgtggccg gcggccagga aacatgagc    3120 ctgtcgcccc acgtgctgcc gggctcgcgc gacggccagc gcatgggcga ctggaagatg    3180
gccgacacca tgatcgtgga cggcctgtgg gacgtctaca accagtacca catgggcatc    3240
acggccgaga acgtggccaa ggaaaagagc gtcagccgcg agcagcagga tgccctggcc    3300
ctggccagcc agcaaaaggc cacggccgcg caggacgccg gcaagttcgt ggacgaaatc    3360
gttcccgtca gcattcccca gcgcaagggc gatcccgtgg tgttcgctgc cgacgagtac    3420
atcaaccgca agaccaatgc cgacgccctg gcaggcctgc gcccggcctt cgacaaggcc    3480
ggctcggtga cggccggcaa cgcctcgggc ctgaacgacg gcgcggccgc cgtggtggtg    3540
```

-continued

```
atgagcgcct ccaaggccaa ggccctgggc ctgacgccgc tggcgcgcat cgtctcctac   3600
gccaccagcg gcctggaccc cgccaccatg ggcctgggcc cggtgttcgc ctcgcgcaag   3660
gcgctggagc gtgcgggctg gaccgcgcag gacgtggacc tgttcgagct gaacgaagcc   3720
ttcgcggccc aggcctgtgc ggtgaaccag gagctgggca tcgacccggc caaggtcaac   3780
gtcaacggcg cgccattgc catcggccac cccatcggcg catcgggcgc ccgcatcctg    3840
gtgaccctgc tgcacgagat gcagcgcagc ggcgccaaga agggcctggc cggcctgtgc   3900
atcggcggcg gcatgggcgt ggccatggcg gtggagcgcg tttgagaggc tccgggaaaa   3960
cgttagcaag ctt                                                      3973

<210> SEQ ID NO 18
<211> LENGTH: 3690
<212> TYPE: DNA
<213> ORGANISM: Methylobacterium extorquens

<400> SEQUENCE: 18
cgtgtccggg ttgaggctca ccccgaagcg ccgctggtag tagccggcct gggcgcggcg     60
caggccggca atgcccttgg aggcggagta gcggtcggtg cgcggcttgc cggccgtctc    120
gacgagcttc tcgatgacgt ggcggggcgc gtcgagatcg ggattgccca tgccgagatc    180
gatgatgtcg gcgccgcggg ctcggccggc ggccttgatc cggttcacct gctcgaagac    240
gtaaggcgga aggcgcttga tgcggtggaa atcggtcatg gcgttggtct gtccggtgtc    300
gcggaactga tcctcccgcg aggatgcgtc ggcggtgagg agcctgcctg tttaccatcg    360
acgcgttcac gcgccgactt aaaaatcaac atcgcgaggc cccgccacga tcggggtgga    420
acgatcactc caccgggttg ggcgcgagcc cctgcgcggc attcttggcc gcccccttccg    480
ccgcgcgccc tttggactcg ttgcggttgc gcgcgccttc cagctcggcc tgcagagcgc    540
tttgtccggc cgaattgcgg gcgcggacgc gcgccggggg cgccgattcg cctaccggca    600
tgtagctcgc atcgctcttg cgggattgcg gccacgaaat cgggcgcctc caccggcttg    660
atgccggagc ccgccccgac catcgccgcc ttcagcggat tcacgtcgcc ggagcagccg    720
ccggtcgccg ccgcggcggc gaaaaccggc aaggcgatgg cgatggcgcg gacggtgcgg    780
cgcacgttca tgacaacggt ctgaaaatgg agtctgggat gggcgacttc tgctgggtgg    840
agcgttaatt tgtcggaaac gaggctcggg ccgccccacg gggcgggatg cgggcagacc    900
tttgggagga cgtgtcgcgt gggcaccgag cggacgaacc cggcagcgcc ggatttcgag    960
accatcgcgc gcaacgcgaa tcagctcgcg gaggtgttcc ggcaatcggc cgccgcctcg   1020
ctgaagccgt tcgagccggc gggccaggga gccctgctcc cgggcgcgaa cctccagggc   1080
gccagcgaga tcgacgagat gacccggacc ctcacgcggg tcgcggagac atggctgaag   1140
gatcccgaga aggcgcttca ggcccagacc aagctcggcc agtccttcgc cgcgctctgg   1200
gcctcgaccc tgacccggat gcaggggcc gtcaccgagc ccgtcgtcca gccccgccc    1260
acggacaagc gcttcgccca tgccgattgg agcgcgaacc cggtcttcga cctgatcaag   1320
cagagctacc tgctccttgg ccgctgggcc gaggagatgg tcgagacggc cgaaggcatc   1380
gatgagcaca cccgccacaa ggcggagttc tacctgcgcc agctcctctc ggcctactcg   1440
ccctcgaact tcgtgatgac gaaccccgag ctcctgcgcc agacgctgga ggagggggc    1500
gccaacctga tgcgcggcat gaagatgctg caggaggatc tggaagccgg cggcggtcag   1560
ctccgggtgc ggcagacgga cctgtccgcc ttcaccttcg gcaaggacgt ggcggtgacc   1620
cccggcgagg tcatcttccg caacgatctg atggagttga tccagtacgc gcccacgacc   1680
```

-continued

```
gagacggtgc tgaagcgtcc gctgctgatc gtgccgccct ggatcaacaa gttctacatc    1740
ctcgatctca acccgcagaa gagcctcatc ggctggatgg tgtctcaagg gatcacggtg    1800
ttcgtgatct cctgggtgaa cccggacgag cgccaccgcg acaaggactt cgagtcctac    1860
atgcgggaag gcatcgagac cgccatcgac atgatcggcg tggcgaccgg cgagaccgat    1920
gtcgcggcgg cgggctactg cgtcggcggc acgctgctcg ccgtcacgct ggcctaccag    1980
gcggcgaccg gcaaccgccg gatcaagagc gcgaccttcc tcaccacgca ggtcgatttc    2040
acccatgcgg gcgatctcaa ggtcttcgcc gacgaggggc agatcaaggc gatcgaggag    2100
cggatggccg agcacggcta cctggagggc gcgcgcatgg ccaacgcctt caacatgctc    2160
aggcccaacg acctgatctg gtcctacgtc gtcaacaact acgtacgcgg caaggcgccg    2220
gccgccttcg acctgctcta ctggaacgcc gacgccacgc ggatgcccgc ggccaaccac    2280
tcgttctacc tgcgcaactg ctacctcaac aacacgctcg ccaaggggca gatggtgctc    2340
ggcaacgtgc gcctcgacct caagaaggtg aaggtgccgg tcttcaacct cgccacccgc    2400
gaggaccaca tcgccccggc gctctcggtc ttcgaagggt cggccaagtt cggcggcaag    2460
gtcgattacg tgctggcggg ctcgggccac atcgccggcg tcgtcgcccc gccgggcccc    2520
aaggccaaat acggctttcg caccggcggc ccggcccgag gccggttcga ggattgggtc    2580
gcggcggcga cggagcatcc gggctcgtgg tggccctact ggtacaagtg gctcgaggag    2640
caggcgcccg agcgcgtgcc cgcccgcatt cctggaacgg ggccctgcc ttccctggcg    2700 ccagcaccgg gcacctatgt ccgcatgaag gcgtgagggc atgaaggtgt gagggatcga    2760
caggaaccgt gcacgcactg catcgctgtt gcggacacgg gaccgtgatt tgccttatct    2820
gatcctgggg ccggctcctg ccccaggagg atagaagcgc gttgcaacac gccaccgatc    2880
tcatttcgat catcgcgctg gggctggtct gcgcgttcat cggcggcatg ctggcccagc    2940
gaatgcggct tccccgctc gtcggctacc tgtcgccgg catcgccatc ggcccgttca    3000
cgccgggttt cgtcggcgat ccggctttag cgagccagct cgccgaactc ggcgtcatcc    3060
tgctgatgtt cggcgtcggg cttcacttct ccatcggtga cctactcgcg gtccgcacca    3120
tcgccctgcc cggtgcgatc gtgcagatca ccgtggcgac cgccatgggc gcgggtctcg    3180 cctgggctt cggctggggg gccggggcgg gcctcgtgtt cggctggcg ctctcggtgg    3240 cgagcactgt cgtgctgttg cgggcgctcg aagggcaggg gcttctcgac tcggacaagg    3300
gccgcatcgc cgtcggctgg ctgatcgtcg aggatctcgc catggtggtg gccctggtgc    3360
tgctgccggc gttggcgccc tcgctcggcg gcgaggcgat gcaggccgcc ggccatcacg    3420
gcccgccgga gcacggcctg tgggtgacgc tcgggctgac gctcgccaag gtcggcgtgt    3480
tcgtcgccgt gatgcttgtc ggcgggcggc gcctcattcc ctacctgctg ggtctggccg    3540
cccgcaccgg ctcgcgcgag ctgttcaccc tggccgtgct ggcgagcgcc gtcggtatcg    3600
ccttcgcctc ctccgagctg ttcggcgtgt ccttcgccct cggcgcgttc ttcgccggga    3660
tggtgctcgc cgaatccgac ctcagccatc                                     3690
```

<210> SEQ ID NO 19
<211> LENGTH: 2712
<212> TYPE: DNA
<213> ORGANISM: Paracoccus denitrificans

<400> SEQUENCE: 19

```
gggcccgcgc gctggcgccc atccattcat tggtgttgcg gatcgtctcc atcgcatcat     60
```

-continued

```
agagagatga tccctctcaa acccttgtac gtcgtcattg caaccttctc ccatgaaccc    120
gccggattcg gccttgccgg ggaaggacac ggctttacct gcgtattgtg ctgggcataa    180
tgattttacg gttcagggag gattgtcaat tatggcgggc aaggacgaaa aaccggaagc    240
tgcgggcgcg gccgaagccg ggggcaaacc acgcaggggc cgcggggcag gggccaaggg    300
ccgtaccggg gacagcgaaa caggagccga agcctgccga ttcggaaaag ccggcgcgac    360
cgcggcgcga aaaggccgcg gtgaagaccc cgcccgagcc cgtgccggag cccgcggcgc    420
ctgccaggtc caaggcggcc gcggcctccg atcccgccaa gcctgccgcc aaggccggca    480
cacgcaaacg ccgcgttgcg cgcgggcggg ggccggtcgc agcgatccgc gccccggtcc    540
gcgccgaaag ccctcgggca aggccgccgc gaaggcgcag gccgagaccg cctcgctcag    600 tatgccgac gaggcgctgc gtccgctggg cgccgtcgga ccgggcggcg gcgtgccgcc    660
catggccgcg ccccgcgccc aggctgccgc cccggcgggg accggccagt ctgccggact    720
cgctgccgag ccgcatccag cccgaacacc gccgccttcg tcgaggcggc cttcggtccc    780
ggcagccgcc tcccaacagc tgcccagaa catcgagcgc atcgaatcgc tgacccagcg    840
cctgatcagc gcgctggcgc agcgccgtcc ctcgaatccc ggcgtcgaga tgccgggccc    900 cgacttttc gccaccgcga cctcggcctg gatcaagctt ctggccgagc agcccgagcg    960
ggtgatcggc cagcaggtca gctattgggg cgaaaccttg cgccatttcg ccgaggccca   1020
ggccgccttt gcccgcggca ccgtgacgcc gccgcccagc gaagggccgc gggaccggcg   1080 cttttgccaac ccgctgtggg aggcgcatcc cttcttcaac ttcatcaagc ggcaatacca   1140
gatcaacgcc caggccctgc aggaggcggc cagcacactg gacctgcccg agatgaccga   1200
ccggcgccgg atcgaatggt tcacccgcca gatgatcgac atgatggcgc cgacgaattt   1260
tctggccacc aatcccgacg acagctggaa aaggcgctgg agaccgaggg acgaaagcct   1320
ggtcaggggc cttgagaacc tggtgcgcga cgtcgagcag aacagcggcg agctgatcgt   1380
gtcgctggcc gaccgcgatg ccttccgtgt gggcgagaac atcggcacca ccgagggcac   1440
ggtggtcgcg cgcaccaagc tttacgagct gatccagtac aagcccacca ccgcgcaggt   1500
gcatgagatc ccgctggtga tctttccgcc ctggatcaac aaattctaca tcctcgacct   1560
caagccgcag aacagcctga tcaaatggat cgtggaccag ggccatacgc tgttcgtggt   1620
ggcctggaag aaccccgacc ccagctatgg cgacaccggc atggacgatt acgtcagcgc   1680
ctatctggag gtgatggacc gggttctgga tctgaccgac cagaaaaagc tgaatgcggt   1740
gggctattgc atcgccggca ccaccctggc gctgaccct gtcgtgctga agcagcgcgg   1800
cgacgaccgg gtgaacgcgg ccaccttctt caccgcgctg accgatttcg ccgaccaggg   1860
cgagttcact gcctatctgc aggaggattt cgtctcaggc atcgaggagg aggcggcgcg   1920
gaccggcatc ctgggcgcgc agctgatgac gcgcaccttc agcttcctgc gcgccaacga   1980
cctggtctgg gggccggcga tccgcagcta catgctgggc gagacgccgc cggccttcga   2040
cctgctgttc tggaacggcg acggcaccaa cctgcccggg cgcatggccg tggaatacct   2100
gcgcggcctg tgccagcaga accgcttcgt caaggagggg ttcgatctga tgggccaccg   2160
cctgcatgtc ggcgacgtga ccgtgccgct ttgcgccatc gcctgcgaga ccgaccatat   2220
cgcgccctgg aaggacagct ggcgcggcat cgcgcagatg ggctccaggg acaagacctt   2280
catcctgtcc gaatcgggcc atatcgccgg catcgtcaac ccgcccagca agaagaaata   2340
cggccattat acctcggacg ccggtttcgg tcagggcgag cagcactggc tggacaaggc   2400
cagccatcac gagggcagct ggtggggccg ctggggcgaa tggctggccc ggcgggcggg   2460
```

-continued

```
gggcatggtc gatgcccgcg acccgggcga gggcttcggc cctgcgccgg gcctttacgt    2520
ccacgagcgg gcgtaaaatt tttctgcacc gcagcaagaa aaccttgcaa tgctgcggtg    2580
cagaaagtat atgttggaca gaacagttca accggtgccg aagcttcgcg ccgacctagg    2640
agagagcaaa tggccaagac ccctgacttt accaagacca tgcaagaagt tatggcgaaa    2700
ttcccggtcg ac                                                         2712
```

<210> SEQ ID NO 20
<211> LENGTH: 2587
<212> TYPE: DNA
<213> ORGANISM: Zoogloea ramigera

<400> SEQUENCE: 20

```
gtcgacctgg gcaaggtcgg gccgcagcaa gtgcccgagg cggacgccag catgaccacc      60
atcgccggca aggtgtgctg gtgatgacgg ccgactgcct gccggtgctg ttttgcgaca     120
cgcgcggcac cgttcgtggc tgccgcccac gccggtcggc gcggcctggc cgctggcgtg     180
ctggaaaaca cctacgcgag cagtgcgcgt ccgcggcgcc ggcgactgat ggcctggatg     240
gggccggcca tcggcgccta ccagttcgag gtgggcggcg atgtgcgcca ggcctttctg     300
caaaccgcac ctgacgattc aagcgtgcgg cacgtgacgg cagcgtttac gccactcgaa     360
caccggccgg gcaagttcct ggccgacatc tacgcgctgg cccggcatcg catgctgcgc     420
gccggcgtgg cgcaagtgca tggcggcgaa tactgcacgg tggccaattc cgggcgcttc     480
tattcgttcc gtcgcgacgg cgtcaccgga cgccaggcaa gtttgatctg gctcaaataa     540
gtatcaggta gggggcgctg gactttttag cgtctcgcgc cgcctgtcgc gctttgcggc     600
gtgctttctc ttgcccgttc ccgcgatgta aatcaaggtc cccagcggca gcacgcaata     660
gaacaaaaac gcaatagcaa caatcagcat gtagcaaccc aggttaagag atattcaata     720 ttttttttagg gaatcacaca tgaatttgcc cgatccgcaa gccattgcca acgcctggat     780
gtcccaggtg ggcgacccca gccaatggca atcctggttc agcaaggcgc ccaccaccga     840
ggcgaacccg atggccacca tgttgcagga tatcggcgtt gcgctcaaac cggaagcgat     900
ggagcagctg aaaaacgatt atctgcgtga cttcaccgcg ttgtggcagg attttttggc     960
tggcaaggcg ccagccgtcc agcgaccgcg cttcagctcg gcagcctggc agggcaatcc    1020
gatgtcggcc ttcaatgccg catcttacct gctcaacgcc aaattcctca gtgccatggt    1080
ggaggcggtg gacaccgcac cccagcaaaa gcagaaaata cgctttgccg tgcagcaggt    1140
gattgatgcc atgtcgcccg cgaacttcct cgccaccaac ccggaagcgc agcaaaaact    1200
gattgaaacc aagggcgaga gcctgacgcg tggcctggtc aatatgctgg gcgatatcaa    1260
tatgctgggc gatatcaaca acggccatat ctcgctgtcg gacgaatcgg cctttgaagt    1320
gggccgcaac ctggccatta cccgggcac cgtgatttac gaaaatccgc tgttccagct    1380
gatccagtac acgccgacca cgccgacggt cagccagcgc ccgctgttga tggtgccgcc    1440
gtgcatcaac aagttctaca tcctcgacct gcaaccggaa aattcgctgg tgcgctacgc    1500
ggtggagcag ggcaacaccg tgttcctgat ctcgtggagc aatccggaca agtcgctggc    1560
cggcaccacc tgggacgact acgtggagca gggcgtgatc gaagcgatcc gcatcgtcca    1620
ggacgtcagc ggccaggaca agctgaacat gttcggcttc tgcgtgggcg gcaccatcgt    1680
tgccaccgca ctggcggtac tggcggcgcg tggccagcac ccggcggcca gcctgaccct    1740
gctgaccacc ttcctcgact tcagcgacac cgggtgctcg acgtcttgtc gagaaaccca    1800
```

```
ggtcgcgctg cgtgaacagc aattgcgcga tggcggcctg atgccgggcc gtgacctggc    1860
ctcgaccttc tcgagcctgc gtccgaacga cctggtatgg aactatgtgc agtcgaacta    1920
cctcaaaggc aatgagccgg cggcgtttga cctgctgttc tggaattcgg acagcaccaa    1980
tttgccgggc ccgatgttct gctggtacct gcgcaacacc tacctggaaa acagcctgaa    2040
agtgccgggc aagctgacgg tggccggcga aaagatcgac ctcggcctga tcgacgcccc    2100
ggccttcatc tacggttcgc gcgaagacca catcgtgccg tggatgtcgg cgtacggttc    2160
gctcgacatc ctgaaccagg gcaagccggg cgccaaccgc ttcgtgctgg cgcgtccgg    2220 ccatatcgcc ggcgtgatca actcggtggc caagaacaag cgcacgtact ggatcaacga    2280
cggtggcgcc gccgatgccc aggcctggtt cgatggcgcg caggaagtgc cgggcagctg    2340
gtggccgcaa tgggccgggt tcctgaccca gcatggcggc aagaaggtca gcccaaggc    2400 caagcccggc aacgcccgct acaccgcgat cgaggcggcg cccggccgtt acgtcaaagc    2460
caagggctga ccacggggaa ctgccagact accggactcg gctattggaa gcgttgcaat    2520
aaatgccagc actattgcga gtttctgcaa tctttctact ttcccctcta taataggatc    2580
cgtcgac                                                             2587

<210> SEQ ID NO 21
<211> LENGTH: 3187
<212> TYPE: DNA
<213> ORGANISM: Aeromonas caviae

<400> SEQUENCE: 21
agatctggac cggggtgctg gcctgggcca cgccggcgag ggccagcgcg gagcaaccga      60
gcagcagggc gagaggtttc atcgggattc cttggcagtc tgaatgacgt gccagcctat     120
cagcgcggcg ccggtgcggc gagggcgcgc cggacccagt gcgtcacctc tcgtctgatc     180
cgcctccctc gacgggcgtc gctgacaaaa aaattcaaac agaaattaac atttatgtca     240
tttacaccaa accgcatttg gttgcagaat gctcaaacgt gtgtttgaac agagcaagca     300
acacgtaaac agggatgaca tgcagtaccc gtaagaaggg ccgattggcc cacaacaaca     360
ctgttctgcc gaactggaga ccgatgatga atatggacgt gatcaagagc tttaccgagc     420
agatgcaagg cttcgccgcc ccctcaccc gctacaacca gctgctggcc agcaacatcg     480
aacagctgac ccggttgcag ctggcctccg ccaacgccta cgccgaactg ggcctcaacc     540
agttgcaggc cgtgagcaag gtgcaggaca cccagagcct gcggccctg gcacagtgc     600 aactggagac cgccagccag ctctcccgcc agatgctgga tgacatccag aagctgagcg     660
ccctcggcca gcagttcaag gaagagctgg atgtcctgac cgcagacggc atcaagaaaa     720
gcacgggcaa ggcctgataa cccctggctg cccgttcggg cagccacatc tccccatgac     780
tcgacgctac gggctagttc ccgcctcggg tgtgggtgaa ggagagcaca tgagccaacc     840
atcttatggc ccgctgttcg aggccctggc ccactacaat gacaagctgc tggccatggc     900
caaggcccag acagagcgca ccgcccaggc gctgctgcag accaatctgg acgatctggg     960
ccaggtgctg gagcagggca gccagcaacc ctggcagctg atccaggccc agatgaactg    1020
gtggcaggat cagctcaagc tgatgcagca caccctgctc aaaagcgcag ccagccgag     1080 cgagccggtg atcaccccgg agcgcagcga tcgccgcttc aaggcgagg cctgagcga    1140 acaacccatc tatgactacc tcaagcagtc ctacctgctc accgccaggc acctgctggc    1200
ctcggtggat gccctggagg gcgtccccca gaagagccgg gagcggctgc gtttcttcac    1260
ccgccagtac gtcaacgcca tggcccccag caacttcctg gccaccaacc ccgagctgct    1320
```

-continued

| | |
|---|---|
| caagctgacc ctggagtccg acggccagaa cctggtgcgc ggactggccc tcttggccga | 1380 |
| ggatctggag cgcagcgccg atcagctcaa catccgcctg accgacgaat ccgccttcga | 1440 |
| gctcgggcgg gatctggccc tgaccccggg ccgggtggtg cagcgcaccg agctctatga | 1500 |
| gctcattcag tacagcccga ctaccgagac ggtgggcaag acacctgtgc tgatagtgcc | 1560 |
| gcccttcatc aacaagtact acatcatgga catgcggccc cagaactccc tggtcgcctg | 1620 |
| gctggtcgcc cagggccaga cggtattcat gatctcctgg cgcaacccgg gcgtggccca | 1680 |
| ggcccaaatc gatctcgacg actacgtggt ggatggcgtc atcgccgccc tggacggcgt | 1740 |
| ggaggcggcc accggcgagc gggaggtgca cggcatcggc tactgcatcg gcggcaccgc | 1800 |
| cctgtcgctc gccatgggct ggctggcggc gcggcgccag aagcagcggg tgcgcaccgc | 1860 |
| caccctgttc actaccctgc tggacttctc ccagcccggg gagcttggca tcttcatcca | 1920 |
| cgagcccatc atagcggcgc tcgaggcgca aaatgaggcc aagggcatca tggacgggcg | 1980 |
| ccagctggcg gtctccttca gcctgctgcg ggagaacagc ctctactgga actactacat | 2040 |
| cgacagctac ctcaagggtc agagcccggt ggccttcgat ctgctgcact ggaacagcga | 2100 |
| cagcaccaat gtggcgggca agaccacaa cagcctgctg cgccgtctct acctggagaa | 2160 |
| ccagctggtg aaggggagc tcaagatccg caacacccgc atcgatctcg gcaaggtgaa | 2220 |
| gaccctgtg ctgctggtgt cggcggtgga cgatcacatc gccctctggc agggcacctg | 2280 |
| gcagggcatg aagctgtttg gcggggagca gcgcttcctc ctggcggagt ccggccacat | 2340 |
| cgccggcatc atcaacccgc cggccgccaa caagtacggg ttctggcaca acggggccga | 2400 |
| ggccgagagc ccggagagct ggctggcagg ggcgacgcac cagggcggct cctggtggcc | 2460 |
| cgagatgatg ggctttatcc agaaccgtga cgaagggtca gagcccgtcc ccgcgcgggt | 2520 |
| cccggaggaa gggctggccc ccgcccccgg ccactatgtc aaggtgcggc tcaaccccgt | 2580 |
| gtttgcctgc ccaacagagg aggacgccgc atgagcgcac aatccctgga agtaggccag | 2640 |
| aaggcccgtc tcagcaagcg gttcggggcg gcggaggtag ccgccttcgc cgcgctctcg | 2700 |
| gaggacttca ccccctgca cctggacccg gccttcgccg ccaccacggc gttcgagcgg | 2760 |
| cccatagtcc acggcatgct gctcgccagc ctcttctccg ggctgctggg ccagcagttg | 2820 |
| ccgggcaagg ggagcatcta tctgggtcaa agcctcagct tcaagctgcc ggtctttgtc | 2880 |
| ggggacgagg tgacggccga ggtggaggtg accgcccttc gcgaggacaa gcccatcgcc | 2940 |
| accctgacca cccgcatctt cacccaaggc ggcgccctcg ccgtgacggg ggaagccgtg | 3000 |
| gtcaagctgc cttaagcacc ggcggcacgc aggcacaatc agcccggccc ctgccgggct | 3060 |
| gattgttctc ccccgctccg cttgcccct ttttcgggc aatttggccc aggccctttc | 3120 |
| cctgccccgc ctaactgcct aaaatggccg ccctgccgtg taggcattca tccagctaga | 3180 |
| ggaattc | 3187 |

<210> SEQ ID NO 22
<211> LENGTH: 2535
<212> TYPE: DNA
<213> ORGANISM: Rattus norvegicus

<400> SEQUENCE: 22

| | |
|---|---|
| gagcagtacc ccggccactg ccagtgtgtg cgtggtgcag gatagactca tggcttcgcc | 60 |
| tctgaggttc gacgggcgtg tggtcctggt caccggcgcc gggggagggt tgggcagagc | 120 |
| ttatgccctg gctttgcag aaagaggagc attagttgtt gtgaatgact taggagggga | 180 |

-continued

```
cttcaaaggc gttgggaaag gctcttctgc cgcagacaag gtcgtggaag aaataagaag      240
gagaggcggg aaagcggtgg ccaattacga ttcaggcgaa gcaggcgaga agcttgtgaa      300
gacagcactg gacacattcg gcagaataga tgttgtggtg aacaatgctg ggatcctgag      360
ggaccgttcc ttctctagga taagtgatga agactgggat ataattcaaa gagttcattt      420
gcggggctcc ttccaagtga cccgggcagc atgggatcat atgaagaagc agaattatgg      480
aagaatcatt atgacggcct cagcttctgg aatatacagc aactttggcc aggcaaatta      540
tagtgctgca aagctgggcc ttctgggtct cgccaatact ctcgtgattg aaggcaggaa      600
gaacaacatt cattgtaaca ccattgcccc aaacgctggg tcacggatga cagagacggt      660
gatgccagaa gacctcgttg aagccctgaa gccagagtat gtggcaccgc tggtcctttg      720
gctttgccat gagagctgtg aggaaaatgg tggcttgttt gaggttggag caggatggat      780
tggaaaattg cgctgggaga ggaccctggg agccattgtc aggaagcgga atcagcccat      840
gactcccgag gcagtgaggg acaactgggt gaagatctgt gacttcagca atgccagcaa      900
gccgaagagc attcaagagt ccacaggtgg tataatcgaa gttttacata aaatagattc      960
agaaggaatc tcacaaaatc acaccggtca agtggcatct gcagatgcat caggatttgc     1020
tggcgtcgtt ggccacaaac ttccttcatt ttcttcttca tatacggaac tgcagtgcat     1080
tatgtatgcc ctcggagtag gagcttcagt caaaaatcca aaggactgaa gtttgttta      1140 tgaagggagt gctgacttct cctgtttgcc tacatttgga gtcattgtcg ctcagaagtc     1200
cttgacgagt ggaggcttag cagaggttcc tgggctgtca atcaactttg caaaggttct     1260
tcatggggag cagtacttgg agttgtataa gccacttccc cgatcagggg aattaaaatg     1320
tgaagcagtt attgctgaca tcctggataa aggctctggc atagtgattg ttatggacgt     1380
ctattcttat tctggcaagg aacttatatg ctataatcag ttctctgtct tcgttgttgg     1440
ctctggaggc tttggtggaa aacggacatc agaaaaactc aaagcagctg tagccgtacc     1500
ggatcggcct ccagatgctg tactgagaga taccacttca ctgaatcagg ccgctctgta     1560
ccgcctcagt ggagactcga atcctttaca cattgacccg agctttgcga gcattgccgg     1620
ttttgagaaa cccatattac acggattatg tacttttggg ttttctgcaa ggcatgtttt     1680
acagcagttt gcggataatg atgtgtcaag attcaaggcc attaaggttc gttttgccaa     1740
accagtgtat ccaggacaaa ctctacaaac tgagatgtgg aaggaaggaa acagaattca     1800
ttttcaaacc aaggtccaag agactggaga cattgtcatt tccaatgcat atgtggatct     1860
tgttcctaca tctggagttt ccgctcagac accttctgag ggtggagcac tgcagagtgc     1920
tcttgtattt ggggaaatag gtcgacgcct caaggatgtt ggacgtgagg tggtaaagaa     1980
agtaaatgct gtatttgaat ggcatatcac gaaaaatggg aatgttgcag ccaagtggac     2040
cattgacctg aagaacggct ctggagaggt ttaccaaggc cctgccaaag gctctgctga     2100
cacgaccatc acaatttctg atgaggattt catggaagtg gtcctgggca gcttaaccc      2160 acagaatgcc ttcttcagtg gcagactgaa ggcccgagga acatcatgc tgagccagaa      2220 gctacagatg attctgaaag actatgccaa gctctgaagg acccactgcg tgctttaata     2280
aaaccagaat cattacgttc tgtctacgca gtcatgctcc agccttcttt gaaacgatcc     2340
acggtaatgt gcagcagaaa tcgcttaaca ttttcagatt cagataactt tcagattttc     2400
attttctact aattttttcac atattatttt tataaggaac tgtaatctag ctagcaaata     2460
attgttctgt tcatagatct gtatcttaat aaaaaaaaag tcaaccgaaa aaaaaaaaa      2520 aaaaaaaaaa aaaaa                                                      2535
```

<210> SEQ ID NO 23
<211> LENGTH: 2328
<212> TYPE: DNA
<213> ORGANISM: Ralstonia eutropha

<400> SEQUENCE: 23

| | | | | | |
|---|---|---|---|---|---|
| ctgcaggttc | cctcccgttt | ccattgaaag | gactacacaa | tgactgacgt | tgtcatcgta | 60 |
| tccgccgccc | gcaccgcggt | cggcaagttt | ggcggctcgc | tggccaagat | cccggcaccg | 120 |
| gaactgggtg | ccgtggtcat | caaggccgcg | ctggagcgcg | ccggcgtcaa | gccgagcag | 180 |
| gtgagcgaag | tcatcatggg | ccaggtgctg | accgccggtt | cgggccagaa | ccccgcacgc | 240 |
| caggccgcga | tcaaggccgg | cctgccggcg | atggtgccgg | ccatgaccat | caacaaggtg | 300 |
| tgcggctcgg | gcctgaaggc | cgtgatgctg | gccgccaacg | cgatcatggc | gggcgacgcc | 360 |
| gagatcgtgg | tggccggcgg | ccaggaaaac | atgagcgccg | ccccgcacgt | gctgccgggc | 420 |
| tcgcgcgatg | gtttccgcat | gggcgatgcc | aagctggtcg | acaccatgat | cgtcgacggc | 480 |
| ctgtgggacg | tgtacaacca | gtaccacatg | ggcatcaccg | ccgagaacgt | ggccaaggaa | 540 |
| tacggcatca | cacgcgaggc | gcaggatgag | ttcgccgtcg | gctcgcagaa | caaggccgaa | 600 |
| gccgcgcaga | aggccggcaa | gtttgacgaa | gagatcgtcc | cggtgctgat | cccgcagcgc | 660 |
| aagggcgacc | cggtggcctt | caagaccgac | gagttcgtgc | gccagggcgc | cacgctggac | 720 |
| agcatgtccg | gcctcaagcc | cgccttcgac | aaggccggca | cggtgaccgc | ggccaacgcc | 780 |
| tcgggcctga | cgacggcgc | cgccgcggtg | gtggtgatgt | cggcggccaa | ggccaaggaa | 840 |
| ctgggcctga | ccccgctggc | cacgatcaag | agctatgcca | acgccggtgt | cgatcccaag | 900 |
| gtgatgggca | tgggcccggt | gccggcctcc | aagcgcgccc | tgtcgcgcgc | cgagtggacc | 960 |
| ccgcaagacc | tggacctgat | ggagatcaac | gaggcctttg | ccgcgcaggc | gctggcggtg | 1020 |
| caccagcaga | tgggctggga | cacctccaag | gtcaatgtga | acggcggcgc | catcgccatc | 1080 |
| ggccacccga | tcggcgcgtc | gggctgccgt | atcctggtga | cgctgctgca | cgagatgaag | 1140 |
| cgccgtgacg | cgaagaaggg | cctggcctcg | ctgtgcatcg | gcggcggcat | gggcgtggcg | 1200 |
| ctggcagtcg | agcgcaaata | aggaagggt | tttccggggc | cgcgcgcggt | tggcgcggac | 1260 |
| ccggcgacga | taacgaagcc | aatcaaggag | tggacatgac | tcagcgcatt | gcgtatgtga | 1320 |
| ccggcggcat | gggtggtatc | ggaaccgcca | tttgccagcg | gctggccaag | gatggctttc | 1380 |
| gtgtggtggc | cggttgcggc | cccaactcgc | gcgccgcga | aaagtggctg | agcagcaga | 1440 |
| aggccctggg | cttcgatttc | attgcctcgg | aaggcaatgt | ggctgactgg | gactcgacca | 1500 |
| agaccgcatt | cgacaaggtc | aagtccgagg | tcggcgaggt | tgatgtgctg | atcaacaacg | 1560 |
| ccggtatcac | ccgcgacgtg | gtgttccgca | agatgacccg | cgccgactgg | gatgcggtga | 1620 |
| tcgacaccaa | cctgacctcg | ctgttcaacg | tcaccaagca | ggtgatcgac | ggcatggccg | 1680 |
| accgtggctg | gggccgcatc | gtcaacatct | cgtcggtgaa | cgggcagaag | ggccagttcg | 1740 |
| gccagaccaa | ctactccacc | gccaaggccg | gcctgcatgg | cttcaccatg | gcactggcgc | 1800 |
| aggaagtggc | gaccaagggc | gtgaccgtca | acacggtctc | tccgggctat | atcgccaccg | 1860 |
| acatggtcaa | ggcgatccgc | caggacgtgc | tcgacaagat | cgtcgcgacg | atcccggtca | 1920 |
| agcgcctggg | cctgccggaa | gagatcgcct | cgatctgcgc | ctggttgtcg | tcggaggagt | 1980 |
| ccggtttctc | gaccgcgcc | gacttctcgc | tcaacggcgg | cctgcatatg | ggctgacctg | 2040 |
| ccggcctggt | tcaaccagtc | ggcagccggc | gctggcgccc | gcgtattgcg | gtgcagccag | 2100 |

| | |
|---|---|
| cgcggcgcac aaggcggcgg gcgtttcgtt tcgccgcccg tttcgcgggc cgtcaaggcc | 2160 |
| cgcgaatcgt ttctgcccgc gcggcattcc tcgcttttg cgccaattca ccgggttttc | 2220 |
| cttaagcccc gtcgcttttc ttagtgcctt gttgggcata gaatcagggc agcggcgcag | 2280 |
| ccagcaccat gttcgtgcag cgcggccctc gcggggggcga ggctgcag | 2328 |

<210> SEQ ID NO 24
<211> LENGTH: 1462
<212> TYPE: DNA
<213> ORGANISM: Raphanus sativus

<400> SEQUENCE: 24

| | |
|---|---|
| gactagtcgc gcgctctctg aactgaagta caagatttcc cgatggccca ttcagcagat | 60 |
| tcctccgaca atcccagaga tgtttgcatc gtgggtgttg cacgcactcc tatgggtggc | 120 |
| tttctcggat ctctctcctc cttacccgcc acaaagcttg gatcccttgc catcacagct | 180 |
| gctctgaaga gagaaatgtt gacccgtctc tggtccaagg aagttgtgtt tgggaatgtt | 240 |
| ctcagtgcta atttgggtca agctcccgct cgtcaggccg ctttaggtgc tgggatctct | 300 |
| aactctgtta tctgtaccac tgtcaacaag gtctgtgcct caggcatgaa agctgtgatg | 360 |
| attgctgctc agagtatcca gctggggatc aatgatgtag tcgtggcggg tggtatggaa | 420 |
| agcatgtcta atacaccaaa gtatcttgca gaagcaagaa aaggatctag gtttggtcat | 480 |
| gattctctcg tagatgggat gcttaaggat ggactgtggg atgtctataa cgactgtggg | 540 |
| atgggaagct gtgcagagtt atgcgctgag aagtttgaga taaccaggga gcagcaagat | 600 |
| gattacgctg ttcagagctt tgagcgtggt attgctgctc aggaatctgg cgccttcaca | 660 |
| tgggagatcg tcccggttga gtttctggga ggaaggggta ggccatcaac cattgttgac | 720 |
| aaggatgaag gtcttgggaa gtttgatgct gcaaaactga ggaaactccg tccgagtttc | 780 |
| aaggagaatg gaggcacagt tacagctgga aatgcctcta gcataagtga tggtgcagct | 840 |
| gctattgtcc tagtgagtgg agagaaggcg cttcagctag gacttcaagt acttgcaaaa | 900 |
| gttaaaggtt atggtgatgc agctcaggag ccagagtttt tcactactgc tcctgctctg | 960 |
| gcaataccaa aagctattgc acccaattcg ccctatagtg agtcgtatca agttgattac | 1020 |
| tatgagatca atgaagcatt tgcagtttgta gcacttgcaa atcaaaagct acttgggatt | 1080 |
| agtccggaga aggtgaatgt aaatggagga gccgtctcct taggacatcc tctaggctgc | 1140 |
| agtggagccc gtattctaat cacattgctt gggatactga agaagagaaa cggcaagtac | 1200 |
| ggtgtgggag gagtgtgcaa cggaggagga ggtgcttctg ctcttgttct tgaagtcgtg | 1260 |
| tgatgcattt atatgaatcc caggttgttg aactatatag agcgtatcta ctatcattct | 1320 |
| accaacttgc acttcaagtt tgatattggt tggtctctct caataaatga gtgatgatga | 1380 |
| tctttgatgt tgttaagttt atttagttat attatatgaa aactatgttt ctgttaaaaa | 1440 |
| aaaaaaaaaa aaaaaaaaa ac | 1462 |

<210> SEQ ID NO 25
<211> LENGTH: 1440
<212> TYPE: DNA
<213> ORGANISM: Pichia membranifaciens

<400> SEQUENCE: 25

| | |
|---|---|
| atggcactcg tcctgcgcag gttcttctcc ggctccgtgg ccagggccac ggcgccagcc | 60 |
| agcctgatca agctccaccc ggtctcgcag ctcaaacaga gacagctgcc cacctacgtg | 120 |
| ggccagtcga actcgatcgt gaagtcgctg gtgtggacca cgccgcccag caacgtgctc | 180 |

-continued

```
attgtgaaga agccgtggca ctccaaggtg ctcgacgccg ccatcacctt catcaagcat      240
ctccacgcaa actacccgtc cgtgaacatc atcgtggtgc ccgaggtcgc cgaggagctc      300
aactcgatcg aacgcaagag ctccgaccca gacacgccca tcggcatcta cacaggcccg      360
ctcaacgaga tcatctccaa gacagacctc attgtctccc tcggcggaga cggcaccatc      420
ctccggggcg tgtcgctctt ctccaacacg acggtcccac ccgtcttgtc cttctccctc      480
ggcacactag ggttccttct cccgttcgac ttcaacaact acgcggaggc gttcaaacag      540
atgttcgagt cccgctccag catcctcaaa agagaacgca tagagtgcca catcgtcaag      600
gctagcccgc aatcggaggc gctcaaccag cagcggaagg acctcgaaac gtcctaccag      660
aacacacgct ccctaaacgc acaagaagag gtggaaaggt tgaagcgctt gtccgcagcc      720
atggatgctc cgttcgacaa tctgacagtc tcctccgagc tcgaggccct caagaaattg      780
aaaatccacg ccatgaacga cattgtcctc cacagaggct ctctcccggg attggtcaac      840
ctcgacgtct acatcaacgg caacctactc acacggacaa ccgcagacgg cctcatcttt      900
gccaccccaa caggctccac agcgtactct cttccggcag gcggttccat cgtcccaccca     960 gtcgtcaagt gcatccttct cacccgatc tgtccgcgaa gcttgtcctt caggcccttg     1020
atcctcccac taaactccca tatcttgatc aaggtcatcg gcaaggaaaa cgtgaagatc     1080
gactacacca agtgcaacgc caaattgagc atagacggaa ttccgcaact gaaaatggtc     1140
cccggcgacg agatccacat catctccgag tccgtctcca gacttaactc cgtaaacgac     1200
gacgaagacg acatcgcctc cggaacaact gcagacgcac cggactgcgt caatgcttcc     1260
actactgtct cgaaggaatc taagacgaag tctctgggaa gacgccgtgg cgtccaaaag     1320
agaaccgcca acgaagtggt cgtctggtgt gttgtccaga gtaagggcga ctgggtcaac     1380
ggcatcaacg gaatgttggg attcaaccta ggattcaagt cttccaagtc aacaaatga     1440
```

<210> SEQ ID NO 26
<211> LENGTH: 3967
<212> TYPE: DNA
<213> ORGANISM: Saccharomyces cerevisiae

<400> SEQUENCE: 26

```
gatcaattct gttaagctct ttacgcatgc ttttattttc ttcactttgg cacattcgct      60
aaagagaaag cgtttgatag ccgcttttgc gatttggtcc tatggtatct ttacactatt     120
catcaatcaa aaaatgaaaa atctccccctt taataatatt gctatcatcc taagtcccat     180
ggatcaatgg tataagggta tcgttcctcg atgggatttt ttttttcaatt ttacattatt     240 gcgtttgtta agttactcca tggattttttt ggaaagatgg catgaacaat tgagccgcca     300
accttcgata gattacgatg atagacgacc tgaattcaga aaaagtttat ctggttctac     360
tctacaaacc atttatgagt caggtaagaa tgttctggag gaaaaggaac gactggtagc     420
agaacatcac atccaggatt acaactttat caatttatc gcttatatta cttacgcgcc     480
attgttttta gtgggcccaa ttatcacttt taatgactac ctttatcaat cagaaaataa     540
gcttccttcg ctaacgaaaa aaaacatagg cttctatgcc ctcaaagtat tttcgagttt     600 gctttttgatg gaaattatcc tacattatat ctatgtgggt gcaatagcaa ggaccaaggc     660
atggaacaat gatacaccct tgcaacaggc tatgatcgcg ctgttcaact gaacattat     720 gtatttaaaa cttttgatcc catggaggct ctttcggctg tgggccatgg tcgatggtat     780
tgatgcacct gaaaatatgc tacgatgtgt ggataataat tatagtacag tgggattctg     840
```

```
gagagcctgg catacaagtt ttaacaagtg ggtaatccgt tacatctatg ttccatttgg      900
cgggtccaat aacaaaatat taacgagctt tgccgtattc tcatttgtag caatatggca      960
tgacatccaa ttacgagtgt tgttttgggg gtggttaaca gtcctttat tattaggcga      1020
aacctacatt actaactgtt ttagtagata tagattcaga agctggtaca ggtttgtttg      1080
cggtatcggt gctgcaataa atatttgcat gatgatgatt attaatgtct atggattttg      1140
cttgggtgca gagggaacga agcttctatt gaagggcata tttaacaatt cacatagtcc      1200
ggagttttg actgcggtaa tggtaagcct atttattgct gttcaggtaa tgtttgagat      1260
tagagaagaa gaaaaaagac atggcatcaa cttgaaatgt tgatctagtt attagataag      1320
ctatgaaagt caatccttt aatcgagaat gtaaatatgt ggaatacaca attttaacca      1380
aagtactata tatgcgttac aagtaattta aatttaagtt caccgaagta aaactaactg      1440
caagattgtt acaagaaca atgcactatt taaatcacac aatggctatt gaaaactgta      1500
actgtcagaa atgctgcatg tatctatatg catcactaag ttgcgactt taagaaactt      1560
ccacagttct caactcttct ttgtgctttt cacacatttt cacaatttc cgaaatctcc      1620
aaattgaaaa aaaaataaaa ataaaaaaag gcaggagaag actaagtatt cattattcgc      1680
tgtttcataa ataaaggat aaaaggtta aggatactga ttaaaatgtt tgtcagggtt      1740
aaattgaata aaccagtaaa atggtatagg ttctatagta cgttggattc acattccta      1800
aagttacaga gcggctcgaa gtttgtaaaa ataaagccag taaataactt gaggagtagt      1860
tcatcagcag atttcgtgtc cccaccaaat tccaaattac aatctttaat ctggcagaac      1920
cctttacaaa atgtttatat aactaaaaaa ccatggactc catccacaag agaagcgatg      1980
gttgaattca taactcattt acatgagtca taccccgagg tgaacgtcat tgttcaaccc      2040
gatgtggcag aagaaattc ccaggattc aaatctcctt tggagaatga tcccaaccga      2100
cctcatatac tttatactgg tcctgaacaa gatatcgtaa acagaacaga cttattggtg      2160
acattgggag gtgatgggac tattttacac ggcgtatcaa tgttcggaaa tacgcaagtt      2220
cctccggttt tagcatttgc tctgggcact ctgggcttc tatcaccgtt tgatttaag      2280
gagcataaaa aggtctttca ggaagtaatc agctctagag ccaaatgttt gcatagaaca      2340
cggctagaat gtcatttgaa aaaaaaggat agcaactcat ctattgtgac ccatgctatg      2400
aatgacatat tcttacatag gggtaattcc cctcatctca ctaacctgga catttcat      2460
gatggggaat ttttgacaag aacgacagca gatggtgttg cattggccac tccaacgggt      2520
tccacagcat attcattatc agcaggtgga tctattgttt ccccattagt ccctgctatt      2580
ttaatgacac caatttgtcc tcgctctttg tcattccgac cactgatttt gcctcattca      2640
tcccacatta ggataaagat aggttccaaa ttgaaccaaa aaccagtcaa cagtgtggta      2700
aaactttctg ttgatggtat tcctcaacag gatttagatg ttggtgatga aatttatgtt      2760
ataaatgagg tcggcactat atacatagat ggtactcagc ttccgacgac aagaaaaact      2820
gaaaatgact ttaataattc aaaaagcct aaaggtcag ggatttattg tgtcgccaag      2880
accgagaatg actggattag aggaatcaat gaacttttag gattcaattc tagctttagg      2940
ctgaccaaga gacagactga taatgattaa acgctctgaa tgcaaagatt caatgagatt      3000
ctctaagaat tctattgata agatttaaag gtatttgaca agtagagatc tttatttttt      3060
cttgcatttt gtctagagaa atctcaactg acatactcga catgaaattt ttggtattgt      3120
gtctttatt ctattgcttt aagaaaactg tgacatatag gaagacatg cttaacaaga      3180
agatataatt atataatata tatattatta ataataacat ccttactgca gtcctgttgt      3240
```

-continued

```
gggagaaaat ggagagagac tatgtttcgt atcaattcct aaaatcaaaa aaaaaaaaaa      3300
aaaaaagtta aacaagcact cgctgttcat ttgttttaca agtattcata ctctaatagg      3360
tcattgagct tctttcttg aggagagatc caatttgaag tcggaataag atttgctttc       3420
attagcgtag gcaataatta tgagataaat ggtgcagcac tattaagtag tgtggatttc      3480
aataatttcc gaattaggaa taaatgcgct aaatagacat cccgttctct ttggtaatct     3540
gcataattct gatgcaatat ccaacaacta tttgtgcaat tatttaacaa aatccaatta     3600
actttcctaa ttagtccttc aatagaacat ctgtattcct tttttttatg aacaccttcc     3660
taattaggcc atcaacgaca gtaaattttg ccgaatttaa tagcttctac tgaaaaacag     3720
tggaccatgt gaaagatgc atctcattta tcaaacacat aatattcaag tgagccttac      3780
ttcaattgta ttgaagtgca agaaaaccaa aaagcaacaa caggttttgg ataagtacat      3840
atataagagg gcctttgtt cccatcaaaa atgttactgt tcttacgatt catttacgat      3900
tcaagaatag ttcaaacaag aagattacaa actatcaatt tcatacacaa ataaacgat     3960 taaaaga                                                                3967
```

<210> SEQ ID NO 27
<211> LENGTH: 1728
<212> TYPE: DNA
<213> ORGANISM: Saccharomyces cerevisiae
<400> SEQUENCE: 27

```
gttattagat aagctatgaa agtcaatcct tttaatcgag aatgtaaata tgtggaatac       60
acaattttaa ccaaagtact atatatgcgt tacaagtaat ttaaatttaa gttcaccgaa     120
gtaaaactaa ctgcaagatt gttacaaaga acatgcact atttaaatca cacaatggct      180
attgaaaact gtaactgtca gaaatgctgc atgtatctat atgcatcact aagttgcgac     240
ttttaagaaa cttccacagt tctcaactct ctttgtgct tttcacacat tttcacaatt      300
ttccgaaatc tccaaattga aaaaaaata aaaataaaaa aaggcaggag aagactaagt      360
attcattatt cgctgtttca taaataaaag gataaaagg ttaaggatac tgattaaaat      420
gtttgtcagg gttaaattga ataaaccagt aaaatggtat aggttctata gtacgttgga     480
ttcacattcc ctaaagttac agagcggctc gaagtttgta aaaatagagg cagtaaataa     540
cttgaggagt agttcatcag cagatttcgt gtccccacca aattccaaat tacaatcttt     600
aatctggcag aacccttac aaaatgttta tataactaaa aaaccatgga ctccatccac      660
aagagaagcg atggttgaat tcataactca tttacatgag tcataccccg aggtgaacgt    720
cattgttcaa cccgatgtgg cagaagaaat ttcccaggat ttcaaatctc ctttggagaa     780
tgatcccaac cgacctcata tactttatac tggtcctgaa caagatatcg taaacagaac    840
agacttattg gtgacattgg gaggtgatgg gactatttta cacggcgtat caatgttcgg    900
aaatacgcaa gttcctccgg ttttagcatt tgctctgggc actctgggct ttctattacc    960
gtttgatttt aaggagcata aaaaggtctt tcaggaagta atcagctcta gagccaaatg   1020
tttgcataga acacggctag aatgtcattt gaaaaaaaag gatagcaact catctattgt   1080 gaccccatgct atgaatgaca tattcttaca taggggtaat tcccctcatc tcactaacct   1140
ggacattttc attgatgggg aattttttgac aagaacgaca gcagatggtg ttgcattggc   1200
cactccaacg ggttccacag catattcatt atcagcaggt ggatctattg tttcccatt    1260 agtccctgct attttaatga caccaatttg tcctcgctct ttgtcattcc gaccactgat   1320
```

-continued

| | | | | | |
|---|---|---|---|---|---|
| tttgcctcat | tcatcccaca | ttaggataaa | gataggttcc | aaattgaacc | aaaaaccagt  1380 |
| caacagtgtg | gtaaaacttt | ctgatgatgg | tattcctcaa | caggatttag | atgttggtga  1440 |
| tgaaagttat | gttataaatg | aggtcggcac | tatatacata | gatggtactc | agcttccgac  1500 |
| gacaagaaaa | actgaaaatg | actttaataa | ttcaaaaaag | cctaaaaggt | cagggattta  1560 |
| ttgtgtcgcc | aagaccgaga | atgactggat | tagaggaatc | aatgaacttt | gtaggattca  1620 |
| ttctagcttt | aggctgacca | agagacagac | tgataatgat | taaacgctct | gaatgcaaag  1680 |
| attcaatgag | attctctaag | aattctattg | ataagattta | aaggtacc | 1728 |

PRODUCTION OF POLYHYDROXYALKANOATE IN PLANTS

CROSS-REFERENCE TO RELATED APPLICATIONS

This application claims the benefit of U.S. Provisional Patent Application No. 60/156,807, filed Sep. 29, 1999.

FIELD OF THE INVENTION

The present invention relates to the genetic manipulation of plants for the production of biodegradable thermoplastics, particularly polyhydroxyalkanoate copolymers.

BACKGROUND OF THE INVENTION

Composed of polymers of a variety of organic compounds, plastics can be molded, extruded, cast into various shapes and films, and even drawn into fibers. It is such versatility that has led to incorporation of plastics into a seemingly endless number of products. Thus, plastic products have become an integral part of everyday life in industrialized society, and the demand for these products is expected to grow as the world population grows and developing countries move up the economic ladder. However, synthetic plastics are slow to degrade in landfills. If and when they do breakdown, the monomers and their derivatives resulting from degradation may actually be more hazardous to human health than the undegraded polymers (Selenskas et al. (1995) Amer. J. Indust. Med. 28:38R–398; Tosti et al. (1993) Toxicol. Indust. Health 9:493–502; Yin et al. (1996) J. Food Drug Anal. 4:313–318). These concerns have raised to a new level the urgency of exploring the use of the environmentally friendly, compostable polymers as substitutes for synthetic plastics. Polyhydroxyalkanoates (PHAs) are polyesters of hydroxyalkanoic acids that are synthesized by a variety of bacteria as storage polymers under stressful conditions (Steinbuchel, A. (1991) *Biomaterials: Novel materials from biological materials*, D. Byrom, ed. (New York: Macmillan Publishers Ltd.), pp. 123–213). Since PHAs have thermoplastic properties, that is they become soft when heated and hard when cooled, and are fully biodegradable, they offer an attractive alternative to synthetic plastics (Brandl et al. (1995) *Can. J. Microbiol.* 41: 143–153; Byrom, D. (1993) *Int. Biodeterior. Biodegrad.* 31:199–208; Lee, S. Y. (1996) *Biotechnol. Bioeng* 49:1–14; Nawrath et al. (1993) *Abst. Pap. Amer. Chem. Soc.* 206: 22–27; Poirier et al. (1995) *Bio/technology Nat. Publ. Co.* 13:142–150; Steinbuechel, A. (1992) *Curr. Opin. Biotechnol.* 3:291–297). Unlike man-made plastics, the production of PHA by living organisms is not dependent on finite natural resources like petroleum.

Currently, only one type of polyhydroxyalkanoate (PHA), Biopol, a copolymer made by fermentation, is commercially available (Poirier et al. (1995) *Bio/technology Nat. Publ. Co.* 13:142–150). However, at approximately $7 per pound, this polymer is much too expensive in comparison to the synthetic plastics that have similar properties but are cheaper with a price of approximately $0.5 per pound (Poirier et al. (1995) *Bio/technology Nat. Publ. Co.* 13:142–150). The higher cost of Biopol results primarily from its cost of production, the main contributing factor being the substrate (Poirier et al. (1995) *Bio/technology Nat. Publ. Co.* 13:142–150). If the PHAs can be produced in plants, the cost of production can be lowered substantially because these polymers would compete with seed oil as natural storage constituents of the cell. The current market price of plant seed oil is between 26 and 28 cents per pound (Anonymous (1998) *Economic Research Service* (Washington, D.C. 20036: U.S. Department of Agriculture). Only about 40% of the energy required to extend a fatty acid chain by two carbons is expended on extending a PHA chain by the same length. Starting with acetyl-CoA, a two carbon extension in oil biosynthesis requires two NADPH and one ATP. In comparison, only one NADPH is needed to accomplish the same for PHA biosynthesis (FIG. 1). Theoretically, more than two units of PHA should be formed for every unit of oil replaced.

Until recently, the only PHA that has been produced in plants was polyhydroxybutyrate (PHB), a homopolymer of 3-hydroxybutyric acid (John et al. (1996) *Proc. Natl. Acad. Sci. USA* 93:12768–12773; Nawrath et al. (1994) *Proc. Natl. Acad. Sci. USA* 91:12760–12764; Padgette et al. (1997) *Plant Physiol.* 114 (Suppl.) 3S; Poirier et al. (1992) *Science* 256:520–523)). Because this polymer is crystalline and brittle with a melting point too close to its degradation point, PHB is difficult to mold into desirable products (Lee, S. Y. (1996) *Biotechnol. Bioeng.* 491:1–14). Many bacteria make copolymers of 3-hydroxyalkanoic acids with a carbon chain length greater than or equal to five (Steinbuchel, A. (1991) *Biomaterials: Novel materials from biological materials*, D. Byrom, ed. (New York: Macmillan Publishers Ltd.), pp. 123–213). Such copolymers are polyesters composed of different 3-hydroxyalkanoic acid monomers. Depending on the composition, these copolymers can have properties ranging from firm to elastic (Anderson et al. (1990) *Microbiol. Rev.* 54:450–472; Lee, S. Y. (1996) *Biotechnol. Bioeng.* 49:1–14). Unlike PHB, the PHA copolymers are suitable for a variety of applications because they exhibit a wide range of physical properties.

Initial attempts at producing PHA in the cytosol proved toxic to the plant (Poirier et al. (1992) *Science* 256:520–523). This problem was overcome by targeting the PHA-producing enzymes to plastids (Nawrath et al. (1994) *Proc. Natl. Acad. Sci. USA* 91:12760–12764). In either cellular compartment, however, only PHB was accumulated, not any of the copolymers. With both of these methods, the genes from *Ralstonia eutropha* (also known as *Alcaligenes eutrophus*) were used. The PHA synthase of this bacterium can utilize only short chain ($C_3$–$C_5$) monomers (Steinbuchel, A. (1991) *Biomaterials. Novel materialsfrom biological materials*, D. Byrom, ed. (New York: Macmillan Publishers Ltd.), pp. 123–213).

Recently, the synthesis of PHA containing 3-hydroxyalkanoic acid monomers ranging from 6 to sixteen carbon in *Arabidopsis thaliana* was reported (Mittendorf et al. (1998) *Proc. Natl. Acad. Sci. USA* 95:13397–13402). To accumulate PHA, the *Arabidopsis* plants were transformed with a nucleotide sequence encoding PHA synthase from *Pseudomonas aeuginosa* that was modified for peroxisome targeting by the addition of a nucleotide sequence encoding the C-terminal 34 amino acids of a *Brassica napus* isocitrate lyase. In these plants, PHA was produced in glyoxysomes, leaf-type peroxisomes and vacuoles. However, PHA production was very low in the *Arabidopsis* plants, suggesting that either the introduced PHA synthase did not function properly in the intended organelle or more likely that the necessary substrates for the introduced PHA synthase were present at levels that were limiting for PHA synthesis. While this report demonstrated that PHA can be produced in peroxisomes of plants, the level of PHA produced in the plants was far below levels necessary for the commercial production of PHA in plants.

SUMMARY OF THE INVENTION

Methods are provided for producing PHA and intermediate molecules thereof in plants. The methods find use in the production of high-quality, biodegradable thermoplastics. The invention provides environmentally friendly alternatives to petroleum-based methods for producing plastics. The methods involve genetically manipulating a plant to produce enzymes for PHA synthesis in its peroxisomes. The methods comprise stably integrating in the genome of a plant nucleotide sequences encoding enzymes involved in the synthesis of PHA, preferably PHA copolymers.

Also provided are plants, plant tissues, plant cells, and seeds thereof, that are genetically manipulated to produce at least one enzyme involved in the synthesis of PHA in plant peroxisomes.

Nucleotide molecules and expression cassettes comprising nucleotide sequences encoding enzymes that can be employed in the synthesis of PHA in the peroxisomes of plants are provided. In particular, the invention provides nucleotide molecules encoding a maize MFP2-like polypeptide, and fragments and variants thereof. Additionally, the invention provides nucleotide molecules comprising nucleotide sequences which encode for either the hydratase or the dehydrogenase domain of the yeast multifunctional protein-2 (MFP2). Such nucleotide molecules encode novel enzymes which find use in PHA synthesis in host cells and plants, particularly in peroxisomes of plants. Isolated polypeptides encoded by the nucleotide molecules of the invention and host cells transformed with such nucleotide molecules are additionally provided.

DETAILED DESCRIPTION OF THE INVENTION

Figure 1:
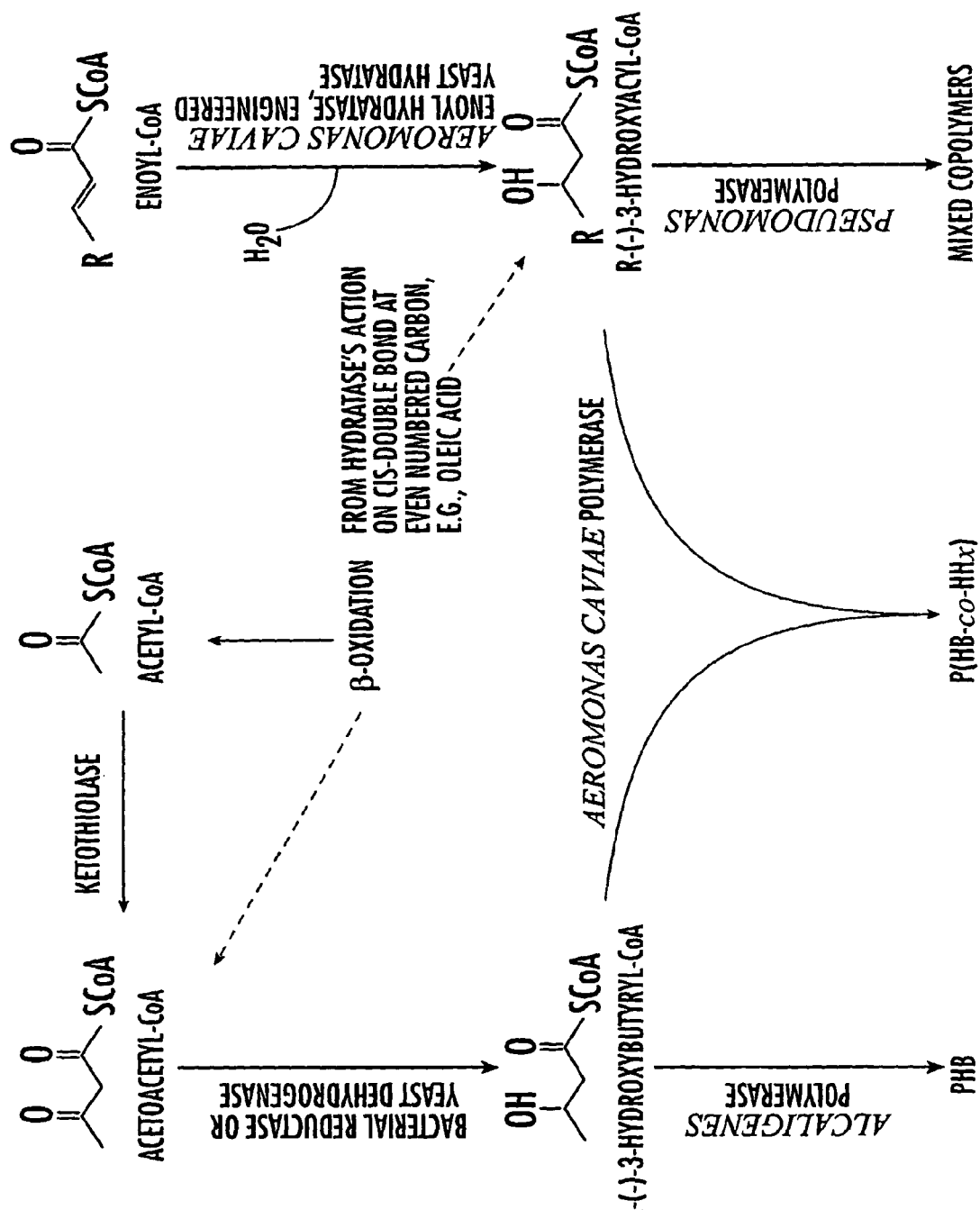
FIG. 1 schematically depicts possible biosynthetic steps for producing PHA in plant peroxisomes utilizing enzymes from bacteria.

A number of terms used herein are defined and clarified in the following section.

By "PHA copolymer" is intended a polymer composed of at least two different 3-hydroxyalkanoic acid monomers.

By "PHA homopolymer" is intended a polymer that is composed of a single 3-hydroxyalkanoic acid monomer.

By "intermediate molecule" is intended a precursor in the biosynthetic pathway for PHA in a plant. Because PHA is not known to occur naturally in a plant, the biosynthetic pathway for PHA in plant additionally encompasses enzymes and products thereof that are involved in PHA synthesis which result from the genetic manipulation of the plant. Intermediate molecules of the present invention include, but are not limited to, fatty acids and β-oxidation products derived therefrom, acetyl-CoA, acetoacetyl-CoA and other 3-ketoacyl-CoAs, 3-hydroxybutyryl-CoA, and other 3-hydroxyacyl-CoAs.

By "modified or unusual" fatty acids is intended fatty acids that have structural features such as, for example, an epoxy group, a triple bond, and methyl branching. Such "modified or unusual" fatty acids include, but are not limited to, vernolic acid, petroselinic acid, sterculic acid, chaulmoogric acid, erucic acid, ricinoleic acid, labellenic acid, crepenynic acid, and stearolic acid.

The present invention is drawn to methods and compositions for producing PHA in plants. Particularly, the present invention provides improved methods for producing PHA in plant peroxisomes. The methods involve increasing the level of PHA produced in a plant by increasing the synthesis of at least one intermediate molecule in PHA synthesis. Thus, the methods involve modifying the metabolic functions of the peroxisome to allow for increased production of PHA in a plant. Furthermore, the invention provides methods for producing PHA copolymers in plant peroxisomes.

Methods for producing PHB in the cytosol or plastids of plants and for producing PHA in plant peroxisomes are known in the art. However, such methods do not achieve the synthesis of high levels of PHA in plants. An object of the present invention is to provide improved methods for producing PHA, preferably PHA copolymers, in plants. The present invention involves genetically modifying plants in such a manner as to alter the metabolic functions of the peroxisome to increase the flux of carbon toward PHA synthesis. Such plants find use in preferred methods for producing high levels of PHA in plants, particularly in seeds, more particularly in oilseeds.

Methods for producing PHA in plants are provided. The methods involve genetically manipulating the genome of a plant to direct the synthesis of PHA to the peroxisomes, preferably peroxisomes in developing seeds. The invention encompasses plants and seeds thereof, that have been genetically manipulated to produce enzymes involved in PHA synthesis and expression cassettes containing coding sequences for such enzymes. The invention further encompasses genetically manipulated plant cells and plant tissues.

Peroxisomes, which are also known as microbodies, are small spherical organelles. In plants, there are generally two types of peroxisomes, leaf-type peroxisomes and glyoxysomes. Glyoxysomes are present in seeds containing oil, particularly during germination (Heldt (1997) *Plant Biochemistry and Plant Molecular Biology*, Oxford University Press, NY). In the present invention, "peroxisome" is intended to encompass all peroxisomes found in plant cells, including, but not limited to, leaf-type peroxisomes, microbodies, and glyoxysomes.

Methods are provided for producing PHA in a plant involving genetically manipulating the plant to produce in its peroxisomes at least two enzymes in the PHA biosynthetic pathway. The plants of the invention each comprise in their genomes at least two stably incorporated DNA constructs, each DNA construct comprising a coding sequence for an enzyme involved in PHA synthesis operably linked to a promoter that drives the expression of a gene in a plant.

Plants of the invention are genetically manipulated to produce a PHA synthase (also known as a PHA polymerase) that catalyzes polymer synthesis. Preferably, such a PHA synthase catalyzes the synthesis of copolymers. More preferably such a PHA synthase catalyzes the synthesis of copolymers comprised of 3-hydroxybutanoic acid monomers and at least one additional monomer having a chain length of greater than four carbons. Most preferably such a PHA synthase catalyzes the synthesis of copolymers comprised of 3-hydroxybutanoic acid monomers and at least one additional monomer having a hydroxyacyl-chain length of from about 5 to about 18 carbons. Preferred PHA synthases include PHA synthases encoded by nucleotide sequences isolatable from *Pseudomonas oleovorans* (GenBank Accession No. M58445, SEQ ID NO: 8), *Pseudomonas putida* (GenBank Accession No. AF042276, SEQ ID NO: 9), *Pseudomonas aeruginosa* (EMBL Accession No. X66592, SEQ ID NO:10), *Aeromonas caviae* (DDBJ Accession No. D88825, SEQ ID NO:11), and *Thiocapsa pfennigii* (EMBL Accession No. A49465, SEQ ID NO:12). The preferred PHA synthases additionally include the PHA synthases encoded by nucleotide sequences isolatable from *Pseudomonas fluorescens* (See U.S. Provisional Patent Application No. 60/156,770 filed Sep. 29, 1999; herein incorporated by reference.). In certain methods of the invention, the majority of PHA copolymers produced are comprised of monomers of chain-length $C_4$ to $C_{18}$.

The DNA constructs of the invention each comprise a coding sequence for an enzyme involved in PHA synthesis operably linked to a promoter that drives expression in a plant cell. Preferably, the promoters are selected from seed-preferred promoters, chemical-regulatable promoters, germination-preferred promoters, and leaf-preferred promoters. If necessary for directing the encoded proteins to the peroxisome, the DNA construct can include an operably linked peroxisome-targeting signal sequence.

It is recognized that for producing high levels of PHA copolymers in certain plants, particularly in their peroxisomes, it may be necessary to genetically manipulate plants to produce additional enzymes involved in PHA synthesis. Generally, the additional enzymes are directed to the peroxisome to increase the synthesis of at least one intermediate molecule. For example, such an intermediate molecule can be the substrate for a PHA synthase including, but not limited to, an R-(−)-3-hydroxyacyl-CoA. The methods of the invention comprise genetically modifying plants to produce, in addition to the PHA synthase described supra, one, two, three, four, or more additional enzymes involved in PHA synthesis. Preferably, each DNA construct comprising the coding sequence of one of these additional enzymes is operably linked to a promoter that drives expression in a plant and also to a nucleotide sequence encoding a peroxisome-targeting signal sequence. Depending on the plant, the addition of one or more of these enzymes may be necessary to achieve high-level PHA synthesis in the plant. The additional enzymes include, but are not limited to, an enzyme that catalyzes the synthesis of R-(−)-3-hydroxyacyl-CoA, a 3-ketoacyl-CoA reductase, and an acetyl-CoA:acetyl transferase.

Additionally, the plant of the invention can comprise in its genome a DNA construct comprising a coding sequence for second PHA synthase. Preferably, the second PHA synthase is capable of synthesizing PHB. Preferred second PHA synthases include those encoded by nucleotide sequences isolatable from *Ralstonia eutropha* (GenBank Accession No. J05003, SEQ ID NO: 13), *Acinetobacter* sp. (GenBank Accession No. U04848, SEQ ID NO: 14), *Alcaligenes latus* (GenBank Accession No. AF078795, SEQ ID NO:15), *Azorhizobium caulinodans* (EMBL Accession No. AJ006237, SEQ ID NO:16), *Comamonas acidovorans* (DDBJ Accession No. AB009273, SEQ ID NO:17), *Methylobacterium extorquens* (GenBank Accession No. L07893, SEQ ID NO:18), *Paracoccus denitrificans* (DDBJ Accession No. D43764, SEQ ID NO:19), and *Zoogloea ramigera* (GenBank U66242, SEQ ID NO: 20)

The methods of the invention additionally comprise growing the plant under conditions favorable for PHA production, harvesting the plant, or one or more parts thereof, and isolating the PHA from the plant or part thereof. Such parts include, but are not limited to, seeds, leaves, stems, roots, fruits, and tubers. The PHA can be isolated from the plant or part thereof by methods known in the art. See, U.S. Pat. Nos. 5,942,597; 5,918,747; 5,899,339; 5,849,854; and 5,821,299; herein incorporated by reference. See also, EP 859858A1, WO 97/07229, WO 97/07230, and WO 97/15681; herein incorporated by reference.

The invention provides methods for producing increased levels of PHA in the peroxisomes of plants that involve increasing the synthesis of one or more intermediate molecules in the peroxisome. The methods involve diverting the flux of carbon in the peroxisome to favor PHA synthesis over endogenous metabolic processes such as, for example, β-oxidation. In a first aspect of the invention, plants are genetically manipulated to increase the synthesis of R-(−)-3-hydroxyacyl-CoAs. In a second aspect of the invention, plants are genetically manipulated to increase the synthesis of a specific R-(−)-3-hydroxyacyl-CoA, R-(−)-3-hydroxybutyryl-CoA. In a third aspect of the invention, the first and second aspects are combined to provide plants that are genetically manipulated to increase the synthesis of both R-(−)-3-hydroxyacyl-CoAs and R-(−)-3-hydroxybutyryl-CoA.

Further, it is recognized that each of the aspects of the invention can be used to produce PHA with substantially different monomer compositions. In particular, the level of 3-hydroxybutanoic acid in the PHA produced in a plant will vary with each aspect. For each particular type of plant, PHA produced by plants of the second or third aspect of the invention is expected to have a higher 3-hydroxybutanoic acid monomer content than PHA produced by plants of the first aspect. Similarly, PHA produced by plants of the second aspect is expected to have a higher 3-hydroxybutanoic acid monomer content than PHA produced by plants of the third aspect.

In a first embodiment of the invention, methods are provided for producing PHA involving genetically manipulating a plant for increased synthesis of R-(−)-3-hydroxyacyl-CoA, a key intermediate molecule in PHA synthesis in the peroxisome. The methods comprise stably integrating into the genome of a plant a first DNA construct comprising a coding sequence for a PHA synthase, and a second DNA construct comprising a coding sequence for an enzyme that catalyzes the formation R-(−)-3-hydroxyacyl-CoA, a substrate of PHA synthase. In β-oxidation in plant peroxisomes, acyl-CoA oxidase catalyzes the conversion of fatty acyl-CoA into 2-enoyl-CoA which is subsequently converted to S-(−)-3-hydroxyacyl-CoA via the 2-enoyl-CoA hydratase of a multifunctional protein. While some R-(−)-3-hydroxyacyl-CoA may be present in peroxisomes, the level is believed to be very low and insufficient to allow for the synthesis of an economically acceptable level of PHA in a plant. Furthermore, all known PHA synthases require that 3-hydroxyacyl-CoA monomers be in R-(−)-form for PHA synthesis. To overcome the substrate limitation for PHA synthesis, the present invention discloses methods for PHA synthesis which involve providing a plant with an enzyme in its peroxisomes that catalyzes the formation of R(−)-3-hydroxyacyl-CoA. By genetically manipulating a plant to increase the synthesis of R-(−)-3-hydroxyacyl-CoA, the present invention overcomes a major impediment to achieving high-level production in plants of PHA, particularly copolymers. Such an enzyme can be an enoyl-CoA hydratase that catalyzes the synthesis of R-(−)-3-hydroxyacyl-CoA, particularly an 2-enoyl-CoA hydratase from *Aeromonas caviae* (DDBJ Accession No. E15860, SEQ ID NO: 21).

Alternatively, two proteins from yeast and one from maize can each be utilized as the enzyme. One such protein is the yeast multifunctional protein (encoded by GenBank Accession No. M86456, SEQ ID NO: 3) which possesses an 2-enoyl-CoA hydratase activity and a 3-hydroxyacyl dehydrogenase (reductase) activity. Similarly, the invention provides an isolated MFP2-like polypeptide (previously designated as a multifunctional protein-2 or MFP-2) from maize (SEQ ID NO: 2) which also possesses an 2-enoyl-CoA hydratase activity. The invention further provides isolated nucleotide molecules encoding such a maize MFP2-like polypeptide (SEQ ID NO: 1). The hydratase of the yeast multifunctional protein and maize MFP2-like polypeptide is known to yield R-(−)-3-hydroxyacyl-CoA products. If necessary, the dehydrogenase activity of the yeast multifunctional protein can be eliminated or neutralized by methods known to those of ordinary skill in the art such as, for example, site-directed mutagenesis, and truncation of the coding sequence to only the portion necessary to encode the desired hydratase activity. The invention provides isolated nucleotide molecules comprising nucleotide sequences which encode either the hydratase or reductase of the yeast multifunctional protein (SEQ ID NOs: 4 and 6). Additionally provided are isolated polypeptides encoded by such sequences (SEQ ID NOs: 5 and 7).

Other multifunctional proteins known in the art can be utilized in the methods of the present invention. Any multifunctional protein possessing a domain comprising a 2-enoyl-CoA hydratase that is capable of catalyzing the synthesis of R-(−)-3-hydroxyacyl-CoA can be employed in the methods of the invention.

The other yeast protein that can be utilized as the enzyme that catalyzes the formation of R-(−)-3-hydroxyacyl-CoA is an enzyme identified as a 3-hydroxybutyryl-CoA dehydrogenase (Leaf et al. (1996) *Microbiology* 142:1169–1180). The gene encoding this enzyme can be cloned from *Saccharomyces cervisae*, sequenced and employed in the methods of the present invention. It is recognized that the nucleotide sequence encoding this enzyme can be modified to alter the amino acid sequence of the enzyme in such a manner as to favorably affect the production of R-(−)-3-hydroxyacyl-CoA in a plant. Such modifications can affect characteristics of the enzyme such as, for example, substrate specificity, product specificity, product inhibition, substrate binding affinity, product binding affinity, and the like. A method such as, for example, DNA shuffling can be employed to modify this enzyme in the desired manner. Any method known in the art for altering the characteristics of an enzyme to favorably affect the mass action ratio toward the desired product is encompassed by the methods of the present invention. Such methods typically involve modifying at least a portion of the nucleotide sequence encoding the enzyme and include, but are not limited to, DNA shuffling, site-directed mutagenesis, and random mutagenesis.

In a second embodiment of the invention, methods are provided for producing PHA involving genetically manipulating a plant for increased synthesis of R-(−)-3-hydroxybutyryl-CoA, a substrate of PHA synthase, in peroxisomes. The methods of the invention provide a plant that is genetically manipulated for increased synthesis of a substrate for a PHA synthase and thus provide a plant that is genetically manipulated for high-level PHA synthesis in its peroxisomes. The methods involve stably integrating into the genome of a plant a first DNA construct comprising a coding sequence for a PHA synthase, and a second DNA construct comprising a coding sequence for 3-ketoacyl-CoA reductase and a third DNA construct comprising a coding sequence for an acetyl-CoA:acetyl transferase. The first, second, and third DNA constructs each additionally comprise an operably linked promoter that drives expression in a plant cell, and if necessary, an operably linked peroxisome-targeting signal sequence. Acetyl-CoA:acetyl transferase, also referred to as ketothiolase, catalyzes the synthesis of acetoacetyl-CoA from two molecules of acetyl-CoA. Acetoacetyl-CoA can then be converted into R-(−)-3-hydroxybutyryl-CoA via a reaction catalyzed by a 3-ketoacyl-CoA reductase, particularly an acetoacetyl-CoA reductase.

Preferred 3-ketoacyl-CoA reductases of the invention are those that utilize NADH and include, but are not limited to, at least a portion of the multifunctional proteins from yeast (encoded by GenBank Accession No. M86456, SEQ ID NO: 3) and rat (encoded by GenBank Accession No. U37486, SEQ ID NO: 22), wherein such a portion comprises a 3-ketoacyl-CoA reductase domain. Any multifunctional protein having a 3-ketoacyl-CoA reductase (dehydrogenase) domain can be employed in the methods of the invention. However, in the methods of the invention, NADPH-dependent 3-ketoacyl-CoA reductases can also be employed including, but not limited to, the 3-ketoacyl-CoA reductases encoded by GenBank Accession No. J04987 (SEQ ID NO: 23).

Preferred acetyl-CoA:acetyl transferases of the invention include a radish acetyl-CoA:acetyl transferase encoded by the nucleotide sequence having EMBL Accession No. X78116 (SEQ ID NO: 24).

If necessary to increase the level of NADPH in the peroxisome, the methods of the second embodiment can additionally involve, stably integrating into the genome of a plant a fourth DNA construct comprising a nucleotide sequence encoding an NADH kinase or an NAD$^+$ kinase and an operably linked promoter that drives expression in a plant cell. Such NADH and NAD$^+$ kinases catalyze the synthesis of NADPH and NADP$^+$, respectively. Nucleotide sequences encoding such kinases include, but are not limited to, DDJB Accession No. E13102 (SEQ ID NO: 25) and EMBL Accession Nos. Z73544 (SEQ ID NO: 26) and X84260 (SEQ ID NO: 27). The fourth construct can additionally comprise an operably linked peroxisome-targeting signal sequence. By targeting such NADH and NAD$^+$ kinases to the peroxisome, the level of NADPH and NADP$^+$ can be increased in the plant peroxisome for use by enzymes, such as, for example, an NADPH-dependent 3-ketoacyl-CoA reductase.

In a third embodiment of the invention, methods are provided for producing PHA in a plant involving genetically manipulating a plant for increased synthesis of R-(−)-3-hydroxybutyryl-CoA and other R-(−)-3-hydroxyacyl-CoA molecules. Such methods provide a plant that is genetically manipulated to overcome substrate limitations for PHA copolymer synthesis in its peroxisomes. The methods involve stably integrating into the genome of a plant a first, a second, a third, and a fourth DNA construct comprising a coding sequence for an enzyme involved in PHA synthesis in a plant. The first DNA construct comprises a coding sequence for a PHA synthase that is capable of catalyzing the synthesis of PHA copolymers. The second DNA construct comprises a coding sequence for an enzyme that catalyzes the synthesis of R-(–)-3-hydroxyacyl-CoA. The third DNA construct comprises a coding sequence for a 3-ketoacyl-CoA reductase, and the fourth DNA construct comprises a coding sequence for an acetyl-CoA:acetyl transferase. If desired, a fifth DNA construct can also be stably integrated into the genome of the plant. The fifth DNA construct comprises a nucleotide sequence encoding a NADH kinase or an $NAD^+$ kinase.

Preferred enzymes of the third embodiment include the enzymes of the first and second embodiments, described supra. The DNA constructs each additionally comprise an operably linked promoter and, if necessary, an operably linked peroxisome-targeting signal to direct the encoded protein to the peroxisome. By targeting such enzymes to the peroxisome, the plant is capable of increased synthesis of intermediate molecules, particularly intermediate molecules that are substrates for a PHA synthase that catalyzes the formation of copolymers.

Methods are provided for increasing the synthesis of PHA in a plant. Such methods find use with methods known in the art for producing PHA in plants, particularly in peroxisomes. The methods of the invention involve increasing the synthesis of an intermediate molecule in PHA synthesis. Preferably, such an intermediate molecule is limiting for PHA synthesis in the peroxisome and that increasing the synthesis of such a molecule in the peroxisome increases the level of PHA produced in a plant. It is recognized that increasing the synthesis of an intermediate molecule in a plant peroxisome might not lead to an increased level of the intermediate molecule in the plant because the intermediate molecule can be further metabolized into, for example, PHA.

The methods for increasing the synthesis of PHA in a plant involve stably incorporating into the genome of a plant at least one DNA construct comprising a coding sequence for an enzyme involved in the synthesis of an intermediate molecule, operably linked to a promoter that drives expression in a plant. If necessary for peroxisome-targeting of the encoded enzyme, the DNA construct additionally comprises a peroxisome-targeting signal operably linked to the coding sequence.

The methods of the invention can be used to increase the synthesis of any intermediate molecule in PHA synthesis. Preferred intermediate molecules include those that can be limiting for PHA synthesis, particularly in the peroxisome, such as, for example, R-(–)-3-hydroxybutyryl-CoA, other R-(–)-3-hydroxyacyl-CoAs, acetoacetyl-CoA, and other 3-ketoacyl-CoAs.

A plant can be genetically manipulated to produce any one or more of the enzymes involved in the synthesis of the intermediate molecule in the plant including, but not limited to, the enzymes for PHA synthesis of the present invention described supra. Preferred enzymes for increasing the synthesis of an intermediate molecule include enzymes, described supra, that catalyze the formation of R-(–)-3-hydroxyacyl-CoA, 3-ketoacyl-CoA reductases that utilize NADH and acetyl-CoA:acetyl transferases.

In a fourth embodiment of the invention, methods are provided for increasing in a plant the synthesis of a R-(–)-3-hydroxyacyl-CoA, key intermediate molecule in PHA synthesis. The level in the peroxisome of R-(–)-3-hydroxyacyl-CoA, a substrate of PHA synthase, is known to be very low and is believed to limit the level of PHA produced in the peroxisome. Thus, increasing the synthesis of R-(–)-3-hydroxyacyl-CoA can increase the synthesis of PHA in a plant. The methods comprise genetically manipulating plants to produce an enzyme that catalyzes the synthesis of R-(–)-3-hydroxyacyl-CoA, preferably an enzyme selected from a 2-enoyl-CoA hydratase from *Aeromonas caviae* (encoded by DDBJ Accession No. E15860, SEQ ID NO: 21), a maize MFP2-like polypeptide (SEQ ID NO: 2), a modified yeast multifunctional protein (SEQ ID NO: 5) possessing a 2-enoyl-CoA hydratase activity and a 3-hydroxyacyl-CoA dehydrogenase activity wherein the latter activity is neutralized, or a modified yeast 3-hydroxyacyl-CoA dehydrogenase, wherein the enzyme utilizes NADH and its mass action ratio has been shifted in favor of R-(–)-3-hydroxyacyl-CoA over 3-ketoacyl-CoA.

Methods are provided for producing novel enzymes for the synthesis of PHA, particularly in peroxisomes, more particularly in plant peroxisomes. The methods find use in providing novel peroxisome-localized enzymes for PHA synthesis in plant peroxisomes. Additionally, the methods find further use in providing DNA constructs that can be used to transform a plant for the production of a PHA synthesis enzyme in its peroxisomes. The methods involve modifying the coding sequence of a multifunctional protein, particularly an MFP2, more particularly an MFP2 from yeast (encoded by GenBank Accession No. M86456, SEQ ID NO: 3) or rat (encoded by GenBank Accession No. U37486, SEQ ID NO: 22). The coding sequence is modified to eliminate or substantially reduce of one of the two separate enzymatic activities of the protein encoded thereby. The coding sequence can be modified by methods known in the art including, but not limited, to site-directed mutagenesis and deletion of a portion of the coding sequence. If necessary, an initiation codon, a stop codon or both can be added to facilitate translation in a host cell. The methods can further involve preparing a DNA construct by operably linking a nucleotide sequence encoding a peroxisome-targeting signal to the modified coding sequence. If desired for expression in a plant or host cell, the DNA construct can additionally comprise an operably linked promoter that drives expression in the plant or cell. The novel enzymes of the invention can be produced by transforming a plant or host cell with such a DNA construct.

Figure 2:
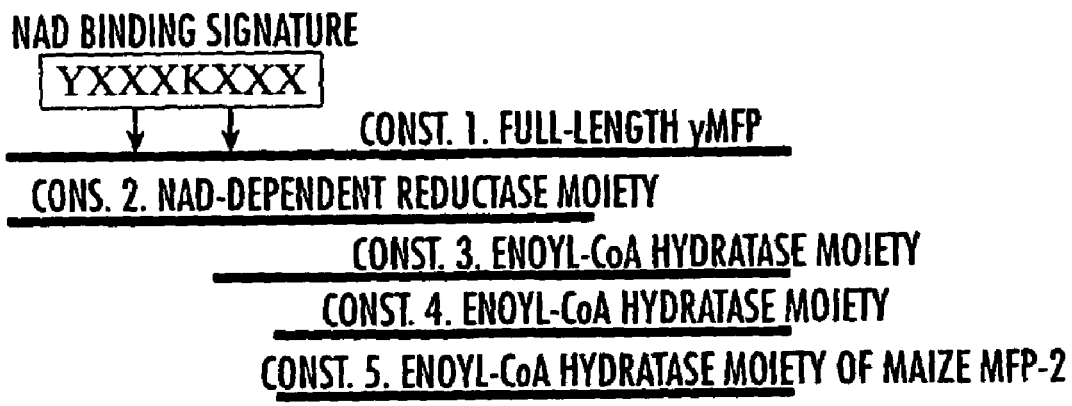
FIG. 2 schematically illustrates the full-length yeast multifunctional protein (yMFP), truncated versions of yMFP, and the maize MFP2-like polypeptide.

In a fifth embodiment of the invention, methods are provided for producing a peroxisome-targeted 2-enoyl-CoA hydratase employing the coding sequence of a yeast MFP2 (GenBank Accession No. M86456, SEQ ID NO: 3). The methods involve modifying the coding sequence to eliminate the dehydrogenase (also referred to as reductase) activity of the encoded protein. This can be accomplished by, for example, deleting from the 5' end of the coding sequence a portion that encoded at least part of the dehydrogenase domain (FIG. 2, SEQ ID NO: 4). To facilitate translation of the encoded protein, an initiation codon can be added to the truncated nucleotide sequence (SEQ ID NO: 4). A DNA construct can be prepared by operably linking a nucleotide sequence encoding a plant peroxisome-targeting signal to such a truncated coding sequence. Such a DNA construct can additionally comprise an operably linked promoter that drives expression in a plant.

In a sixth embodiment of the invention, methods are provided for producing a NADH-dependent, peroxisome-targeted 3-ketoacyl-CoA reductase employing the coding sequence of a yeast multifunctional protein (GenBank Accession No. M86456, SEQ ID NO: 3). The methods involve modifying the coding sequence of a multifunctional protein to eliminate the hydratase activity of the encoded protein. Because the reductase of the yeast multifunctional protein is known to be NADH dependent, a peroxisome-targeted 3-ketoacyl-CoA reductase is expected to be NADH dependent. Such an NADH-dependent reductase finds use in the high-level synthesis of PHA in plant peroxisomes where NADPH, but not NADH, is known to be limiting. This can be accomplished by, for example, deleting from the 3' end of the coding sequence a portion that encoded at least a part of the hydratase domain (FIG. 2, SEQ ID NO: 6). To facilitate translation of the desired polypeptide, an appropriate stop codon can be operably linked to the 3' end of the truncated coding sequence (SEQ ID NO: 6). In addition, a DNA construct can be prepared by operably linking a nucleotide sequence encoding a plant peroxisome-targeting signal to such a truncated coding sequence. Such a DNA construct can additionally comprise an operably linked promoter that drives expression in a plant.

Methods are provided for increasing the level in a plant of at least one intermediate molecule in PHA synthesis in the plant. Such intermediate molecules include molecules naturally synthesized by the plant as well as those that are synthesized by the plant after being genetically manipulated to comprise at least one enzyme involved in PHA synthesis that does not occur naturally in the plant. The methods involve the buildup of intermediate molecules as well as the use of additional enzymes for the production of specialty chemicals. Thus, plants containing intermediate molecules or PHA can be obtained. It is recognized that methods of the present invention can be used in combination with methods for producing PHA homopolymers, copolymers or both.

To increase the level of at least one intermediate molecule in a plant, the plant can be genetically manipulated to produce any one or more of the enzymes involved in the synthesis of the intermediate molecule in the plant including, but not limited to, the enzymes for PHA synthesis of the present invention described supra. Preferred enzymes for increasing the synthesis of an intermediate molecule include enzymes, described supra, that catalyze the formation of R-(−)-3-hydroxyacyl-CoA, 3-ketoacyl-CoA reductases that utilize NADH and acetyl-CoA:acetyl transferases.

Further, it is recognized that it may be necessary to lower or eliminate the activity of an endogenous enzyme in a plant that in some way limits the synthesis of the desired intermediate molecule. Such an endogenous enzyme may, for example, catabolize or modify the intermediate molecule in an undesirable way. Methods for lowering or eliminating the activity of an enzyme in a plant include, but are not limited to, sense and antisense suppression methods. For example, the activity of the 2-enoyl-CoA hydratase of an endogenous multifunctional protein that catalyzes the formation of S-(+)-3-hydroxyacyl-CoA can be reduced or eliminated in the peroxisome to favor, instead, the synthesis of R-(−)-3-hydroxyacyl-CoA therein.

While the methods of the invention can be used with any plant, preferred plants are oilseed plants genetically manipulated to produce PHA copolymers in their peroxisomes, particularly in seeds. More preferably, the oilseed plants have been genetically manipulated to have seeds with increased levels of short-chain fatty acids, modified or unusual fatty acids, cytosolic acyl-CoA oxidase activity, or combinations thereof. Such oilseed plants have increased rates of β-oxidation in their seeds and find use in methods of producing high levels of PHA copolymers, particularly in seeds.

While the compositions and methods disclosed herein are drawn to the production of PHA and PHA intermediates in plants, the present invention is not limited to methods involving PHA production in plant and cells thereof. Those skilled in the art will recognize that the compositions and methods can be employed with any host cell for the production of PHA and intermediates thereof. Host cells include, but are not limited to, plant cells, animal cells, bacterial cells and fungal cells, particularly yeast cells.

Compositions comprising nucleic acid molecules which comprise coding sequences for enzymes involved in the synthesis of PHA in the peroxisomes of plants are provided. Compositions of the invention include nucleotide molecules encoding a maize MFP2-like polypeptide and fragments and variants thereof. In particular, the present invention provides for isolated nucleic acid molecules comprising nucleotide sequences encoding the amino acid sequence set forth in SEQ ID NO: 2. Further provided are polypeptides having an amino acid sequence encoded by a nucleic acid molecule described herein, for example that set forth in SEQ ID NO: 1, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein of the invention. Alternatively, fragments of a nucleotide sequence that are useful as hybridization probes generally do not retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a nucleotide sequence of the invention that encodes a biologically active portion of a multifunctional protein will encode at least 15, 25, 30, 50, 100, 150, 200, 250 or 300 contiguous amino acids, or up to the total number of amino acids present in a full-length multifunctional protein of the invention (for example, 314 amino acids for SEQ ID NO: 2). Fragments of a multifunctional protein nucleotide sequence that are useful as hybridization probes for PCR primers generally need not encode a biologically active portion of a multifunctional protein.

Thus, a fragment of a multifunctional protein nucleotide sequence may encode a biologically active portion of a multifunctional protein, or it may be a fragment that can be used as a hybridization probe or PCR primer using methods disclosed below. A biologically active portion of a multifunctional protein can be prepared by isolating a portion of one of the multifunctional protein nucleotide sequences of the invention, expressing the encoded portion of the multifunctional protein (e.g., by recombinant expression in vitro), and assessing the activity of the encoded portion of the multifunctional protein. Nucleic acid molecules that are fragments of a multifunctional protein nucleotide sequence comprise at least 16, 20, 50, 75, 100, 150, 200, 250, 300, 350, 400, 450, 500, 550, 600, 650, 700, 800, 900, 1,000, 1,100, 1,200 or 1,300 nucleotides, or up to the number of nucleotides present in a full-length multifunctional protein nucleotide sequence disclosed herein (for example, 1362 nucleotides for SEQ ID NO: 1).

By "variants" is intended substantially similar sequences. For nucleotide sequences, conservative variants include those sequences that, because of the degeneracy of the genetic code, encode the amino acid sequence of one of the multifunctional proteins or other enzymes involved in PHA synthesis of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a multifunctional protein or other enzyme of the invention. Generally, variants of a particular nucleotide sequence of the invention will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequence set forth herein. Sequences isolated based on their sequence identity to the entire maize MFP2-like polypeptide nucleotide sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the maize MFP2-like polypeptide nucleotide sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire maize MFP2-like polypeptide nucleotide sequence disclosed herein, or one or more portions thereof, may be used as a probe capable of specifically hybridizing to corresponding MFP2 sequences and messenger RNAs. To achieve specific hybridization under a variety of conditions, such probes include sequences that are unique among MFP2 sequences and are preferably at least about 10 nucleotides in length, and most preferably at least about 20 nucleotides in length. Such probes may be used to amplify corresponding MFP2 sequences from a chosen organism by PCR. This technique may be used to isolate additional coding sequences from a desired organism or as a diagnostic assay to determine the presence of coding sequences in a organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5°C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10°C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10°C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology -Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an MFP2 and which hybridize under stringent conditions to the MFP2 sequence disclosed herein, or to fragments thereof, are encompassed by the present invention. Such sequences will be at least about 50% to 60% homologous, about 60%, to 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 50% to 60%, about 65% or 70%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity". (a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIDOS*8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs that can be employed in the methods of the present invention including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

In the practice of embodiments of the invention, heterologous DNA can be employed. By "heterologous DNA" is intended DNA that is foreign to the genome of an organism. Such foreign DNA encompasses any DNA present in the genome of an organism that originated in the present organism or one of its progenitors by artificial methods such as, for example, transformation. Such foreign DNA also encompasses DNA native to an organism introduced into the genome of the organism via non-natural methods such as, for example, transformation. Related terms include "heterologous protein" and "heterologous enzyme" which are encoded by "heterologous DNA." It is recognized that such a heterologous enzyme or protein can possess an amino acid sequence that is identical to that of a native enzyme or protein of an organism. Further, a "heterologous coding sequence" is coding sequence composed of heterologous DNA.

It is recognized that enzymes similar to those described herein, referred to as "variant enzymes," may be utilized. By "variant enzyme" or "variant protein" is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess at least one desired biological activity of the native protein, that is, for example, 2-enoyl-CoA hydratase or 3-ketoacyl-CoA reductase activity as described herein for MFP2. Such variants may result from, for example, genetic polymorphism or from human manipulation. Biologically active variants of a native enzyme or protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the polypeptide can be prepared by mutations in the nucleotide sequence encoding the native protein of interest which is also referred to as the coding sequence of the native protein. Thus, proteins and their respective coding sequences include the native forms as well as variants thereof.

A variety of methods can be used to produce variant enzymes such as, for example, mutagenesis of the coding sequences of the native enzyme. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the enzyme of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

In some cases it may be necessary to utilize a protein that possesses more than one enzymatic function. If only one or subset of enzymatic activities of such a protein is desired, it will be necessary to "neutralize," that is eliminate or substantially minimize, the undesirable enzymatic activity or activities. Those skilled in the art of modifying proteins and enzymes know that a variety of methods can be used singly or in combination to neutralize an enzymatic activity. Generally such methods involve modifying the coding sequences of the protein such that the desired activity or activities are retained and the undesirable activity or activities are eliminated. Such modifications to the coding sequence include deletions, substitutions, and insertions.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by enzyme activity assays, such as, for example, a PHA synthase assay, an enoyl-CoA hydratase assay, a ketoacyl-CoA reductase assay and an acetyl-CoA: acetyl transferase assay. See, for example, Schubert et al. (1988) *J. Bacteriol.* 170:5837–5847 (PHA synthase), Valentin and Steinbuechel (1994) *Appl Microbiol Biotechnol.* 40:699–709 (PHA synthase), Moskowitz and Merrick (1969) *Biochemistry* 8:2748–2755 (enoyl-CoA hydratase), Lynen and Wieland (1955) *Meth. Enzymol.* 1:566–573 (ketoacyl-CoA reductase), Nishimura et al. (1978) *Arch Microbiol.* 116:21–27 (acetyl-CoA:acetyl transferase) and Iwahashi et al. (1989) *J. Biochem.* 105:588–593 (NAD/NADH kinase); all of which are herein incorporated by reference.

Nucleotide sequence encoding the enzymes of the invention may be derived from a mutagenic and recombinogenic procedure such as DNA shuffling. With such a procedure, one or more different coding sequences of an enzyme of the invention can be manipulated to create a new enzyme possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, nucleotide sequence motifs encoding a domain of interest in an enzyme of the invention may be shuffled to obtain a new gene coding for an enzyme with an improved or modified property of interest, such as an increased $K_m$, or modification that results in changes in substrate or product specificities of the enzyme. Such changes in substrate and product specificities include, but are not limited, to changes related to stereochemistry of the substrate utilized and/or the product formed. For example, an enzyme may only catalyze the formation of a epimer of a particular product. However, after shuffling one or more nucleotide sequences encoding such an enzyme, a variant enzyme is produced that produces only the (–)-epimer of the same product. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458, herein incorporated by reference.

In embodiments of the invention, it is necessary to direct an enzyme for PHA synthesis to the peroxisomes of a plant. Methods for directing an enzyme to the peroxisome are well known in the art. Typically, such methods involve operably linking a nucleotide sequence encoding a peroxisome-targeting signal to the coding sequence of the enzyme or modifying the coding sequence of the enzyme to additionally encode the peroxisome-targeting signal without substantially affecting the intended function of the encoded enzyme. See, for example, Olsen et al. (1993) *Plant Cell* 5:941–952, Mullen et al. (1997) *Plant Physiol* 115:881–889, Gould et al. (1990) *EMBO J.* 9:85–90, Flynn et al. (1998) *Plant J.* 16:709–720; Preisig-Muller and Kindl (1993) *Plant Mol. Biol.* 22:59–66 and Kato et al. (1996) *Plant Cell* 8:1601–1611; herein incorporated by reference.

It is recognized that an enzyme of the invention may be directed to the peroxisome by operably linking a peroxisome-targeting signal to the C-terminus or the N-terminus of the enzyme. It is further recognized that an enzyme which is synthesized with a peroxisome-targeting signal may be processed proteolytically in vivo resulting in the removal of the peroxisome-targeting signal from the amino acid sequence of the mature, peroxisome-localized enzyme.

It is recognized that it may be necessary to reduce or eliminate the activity of one or more enzymes in a plant that interfere with PHA production by the methods of the present invention. The activity of such an interfering enzyme may be reduced or eliminated by reducing or eliminating the synthesis of the interfering enzyme. Methods for reducing or eliminating the synthesis of a particular protein or enzyme in a plant, such as, for example, sense and antisense suppression methods, are known in the art.

Antisense suppression methods involve the use of DNA construct that is portion complementary to at least a portion of a transcript encoding the protein of interest. The antisense DNA construct is designed for the production of antisense transcripts when transcribed in a plant. Such antisense transcripts are capable of hybridizing with the corresponding native or sense transcript of the protein of interest. Modifications of the antisense sequences may be made as long as the sequences hybridize to and interfere with expression of the corresponding sense transcript. In this manner, antisense constructions having 70%, preferably 80%, more preferably 85% sequence identity to the corresponding sense transcript may be used. Furthermore, portions of the antisense nucleotides may be used to disrupt the expression of the target gene. Generally, sequences of at least 50 nucleotides, 100 nucleotides, 200 nucleotides, or greater may be used.

Sense suppression methods, also known as cosuppression methods, involve the use of DNA construct that is designed to produce of a transcript that is in the same orientation, the sense orientation, as the transcript of the protein of interest. Methods for suppressing the production of a protein in a plant using nucleotide sequences in the sense orientation to are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

In the methods of the present invention, expression cassettes can be utilized. The cassette will include 5' and 3' regulatory sequences operably linked to the gene of interest. Generally, the expression cassette is provided with a plurality of restriction sites for insertion of the sequence to be under the transcriptional regulation of the regulatory regions. The expression cassette may additionally contain selectable marker genes.

By "operably linked" is intended the joining of two or more contiguous nucleotide sequences in such a manner that the desired functions or functions are achieved. "Operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of protein coding sequences, "operably linked" includes joining two protein coding sequences in such a manner that both sequences are in the same reading frame for translation. For example, a nucleotide sequence encoding a peroxisome-targeting signal may be joined to the 3' end of a coding sequence of a protein of the invention in such manner that both sequences are in the same reading frame for translation to yield a the protein of the invention with a C-terminal addition of the peroxisome-targeting signal.

The cassette may additionally contain at least one additional gene to be cotransformed into the organism. Alternatively, the additional gene(s) can be provided on multiple expression cassettes.

The expression cassette will include in the 5'-to-3' direction of transcription, a transcriptional and translational initiation region, a nucleotide sequence of interest, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of MFP2 in the plant or plant cell. Thus, the phenotype of the plant or plant cell is altered.

The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

The coding sequences of the enzymes for PHA biosynthesis used in the practice of the invention can be optimized for enhanced expression in plants of interest. That is, the coding sequences can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference. Thus, the nucleotide sequences can be optimized for expression in any plant. It is recognized that all or any part of the nucleotide sequence may be optimized or synthetic. That is, synthetic or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picomavirus leaders, for example, EMCV leader (Encephalomyocarditis 5'-noncoding region) (Elroy-Stein, O., Fuerst, T. R., and Moss, B. (1989) *Proc. Natl. Acad. Sci. USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak, D. G., and P. Sarnow (1991) *Nature* 353:90–94; untranslated leader from the coat protein mRNA of alfalfa mosaic virus (AMV RNA 4), (Jobling, S. A., and Gehrke, L., (1987) *Nature* 325:622–625; tobacco mosaic virus leader (TmV), (Gallie, D. R. et al. (1989) *Molecular Biology of RNA*, pages 237–256; and maize chlorotic mottle virus leader (MCMV) (Lommel, S. A. et al. (1991) *Virology* 81:382–385). See also, Della-Cioppa et al. (1987) *Plant Physiology,* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, re-substitutions, e.g., transitions and transversions, may be involved. Such a fragment of DNA that has been manipulated by any method known to those skill in the art is referred to herein as a "DNA construct." The term "DNA construct " also encompasses expression cassettes, chimeric genes, synthetic genes, genes with modified coding sequences, and the like.

A number of promoters can be used in the practice of the invention. The promoters may be selected based on the desired timing, localization and level of expression genes encoding enzymes in a plant. Constitutive, seed-preferred, germination-preferred, tissue-preferred and chemical-regulatable promoters can be used in the practice of the invention. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The methods of the invention are useful for producing PHA copolymers in seeds. Toward this end, the coding sequences for the enzymes of the invention may be utilized in expression cassettes or DNA constructs with seed-preferred promoters, seed-development promoters (those promoters active during seed development), as well as seed-germination promoters (those promoters active during seed germination). Such seed-preferred promoters include, but are not limited to, Ciml (cytokinin-induced message); cZ19B1 (maize 19 kDa zein); and celA (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glob-1 is a preferred embryo-specific promoter. For dicots, particular promoters include those from the following genes: phaseolin, napin, β-conglycinin, soybean lectin, and the like. For monocots, particular promoters include those from the following genes: maize 15 Kd zein, 22 KD zein, 27 kD zein, waxy, shrunken 1, shrunken 2, and globulin 1.

For tissue-preferred expression, the coding sequences of the invention can be operably linked to tissue-preferred promoters. For example, leaf-preferred promoters may be utilized if expression in leaves is desired. Leaf-preferred promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6): 1129–1138; and Matsuoka et al. (1993) *Proc. Natl. Acad. Sci. USA* 90(20):9586–9590.

Other tissue-preferred promoters include, for example, Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Lam (1994) *Results Probl Cell Differ.* 20:181–196; Orozco et al. (1993) *Plant Mol. Biol.* 23(6):1129–1138; and Guevara-Garcia et al. (1993) *Plant J.* 4(3):495–505.

In the practice of the invention, it may be desirable to use chemical-regulatable promoters to control the expression of gene in a plant. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulatable promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

It is further recognized that the components of the expression cassette may be modified to increase expression. For example, truncated sequences, nucleotide substitutions or other modifications may be employed. See, for example Perlak et al.(1991) *Proc. Natl. Acad. Sci. USA* 88:3324–3328; Murray et al. (1989) *Nucleic Acid Research* 17:477–498; and WO 91/16432.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

In the methods of the present invention, plants genetically manipulated to produce PHA are utilized. By "genetically manipulated" is intended modifying the genome of an organism, preferably a plant, including cells and tissue thereof, by any means known to those skilled in the art. Modifications to a genome include both losses and additions of genetic material as well as any sorts of rearrangements in the organization of the genome. Such modifications can be accomplished by, for example, transforming a plant's genome with a DNA construct containing nucleotide sequences which are native to the recipient plant, non-native or a combination of both, conducting a directed sexual mating or cross pollination within a single species or between related species, fusing or transferring nuclei, inducing mutagenesis and the like.

In the practice of certain specific embodiments of the present invention, a plant is genetically manipulated to produce more than one heterologous enzyme involved in PHA synthesis. Those of ordinary skill in the art realize that this can be accomplished in any one of a number of ways. For example, each of the respective coding sequences for such enzymes can be operably linked to a promoter and then joined together in a single continuous fragment of DNA comprising a multigenic expression cassette. Such a multigenic expression cassette can be used to transform a plant to produce the desired outcome. Alternatively, separate plants can be transformed with expression cassettes containing one or a subset of the desired set of coding sequences. Transformed plants that express the desired activity can be selected by standard methods available in the art such as, for example, assaying enzyme activities, immunoblotting using antibodies which bind to the enzymes of interest, assaying for the products of a reporter or marker gene, and the like. Then, all of the desired coding sequences can be brought together into a single plant through one or more rounds of cross pollination utilizing the previously selected transformed plants as parents.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described supra for selecting transformed plants. If necessary, the selected progeny can be used as either the pollen donor or pollen recipient in a subsequent cross pollination.

The invention can be practiced with any plant species including, but not limited to, monocots and dicots. Examples of plants of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago saliva*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinclorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Preferably, plants of the present invention are crop plants (for example, maize, alfalfa, sunflower, *Brassica* sp., soybean, cotton, safflower, peanut, sorghum, wheat, rice, potatoes, millet, tobacco, etc.), more preferably maize and oilseed plants, yet more preferably maize plants. Such oilseed plants include, but are not limited to, *Brassica* sp., sunflower, safflower, soybean, peanut, cotton, flax, coconut and oil palm.

The following examples are offered by way of illustration and not by way of limitation.

EXPERIMENTAL

Example 1

Engineering Plants to Produce PHA Copolymers

Bacteria can produce PHA copolymers because these substrates are apparently derived from the β-oxidation cycle; as bacterial cells are uncompartmented, both β-oxidation and PHA synthesis take place in the cytosol. In plants, however, β-oxidation is confined primarily to peroxisomes and thus offers a suitable site for copolymer production. Using methods known to those of ordinary skill in the art, signal sequences for targeting proteins to peroxisomes can be added to PHA-producing enzymes, allowing the localization of these enzymes in the peroxisomes. Such signal sequences for targeting proteins to plant peroxisomes are well known (Mullen et al. (1997) *Plant Journal* 12:313–322; Trelease et al. (1996) *Protoplasma* 195:156–167).

An intermediate in β-oxidation is S-(+)-3-hydroxyacyl-CoA. However, its configuration is unsuitable for PHA synthases, which require R-(−)-3-hydroxyacyl-CoA as a substrate (Gemgross et al. (1995) *Proc. Natl. Acad. Sci. USA* 92:6279–6283; Steinbuchel, A. (1991) *Biomaterials: Novel materials from biological materials*, D. Byrom, ed. (New York: Macmillan Publishers Ltd.), pp. 123–213). Moreover, the concentration of R-(−)-3-hydroxyacyl-CoA in the peroxisomes must be very low, as the enzyme catalyzing the proximal and distal reactions of this intermediate is multifunctional in nature (Engeland et al. (1991) *Eur. J. Biochem.* 200:171–178; Guhnemann Schafer et al. (1995) *Biochim. Biophys. Acta.* 1256:181–186). As acyl-CoA oxidase appears to be an independent enzyme (i.e., not a component of a multi-enzyme complex) in β-oxidation, its product, 2-enoyl-CoA, might be readily available for hydration into the R-(−)-epimer, provided that a hydratase capable of catalyzing this reaction is available (FIG. 1).

A multifunctional protein from yeast reportedly has only the activities of enoyl-CoA hydratase and R-(−)-3-hydroxyacyl-CoA dehydrogenase (Hiltunen et al. (1992) *J. Biol. Chem.* 267:6646–6653). Interestingly, this enoyl-CoA hydratase forms R-(−)-3-hydroxyacyl-CoA in contrast to its plant counterpart (Guhnemann et al. (1994) *Eur. J. Biochem.* 226:909–915; Kindl, H. (1993) *Biochimie* 75:22R–230). Engineering the yeast multifunctional protein (encoded by GenBank Accession No. M86456, SEQ ID NO: 3) to carry only the hydratase activity and then targeting it to the plant peroxisomes along with a PHA synthase should lead to PHA copolymer formation.

Leaf et al. ((1996) *Microbiology* 142:1169–1180) were able to produce PHB granules in the cytosol of yeast transformed with only PHB synthase. Although they were unable to pinpoint the compartment in which it was localized, they identified a 3-hydroxybutyryl-CoA dehydrogenase that catalyzed the reversible reaction between acetoacetyl-CoA and R-(−)-3-hydroxybutyryl-CoA. No further information (i.e. gene or protein sequence) is available on this enzyme yet. Once the gene for 3-hydroxyacyl-CoA dehydrogenase enzyme becomes available, it can be used in producing substrate for PHA copolymer formation in peroxisomes. It is recognized that the coding sequence of this enzyme can be manipulated to alter characteristics of the encoded enzyme to favor the synthesis R-(−)-3-hydroxyacyl-CoA over 3-ketoacyl-CoA in plant peroxisomes by techniques well known to those skilled in the art. Such techniques include, for example, e.g., DNA shuffling (Crameri et al. (1998) *Nature* 391:288–291; Stemmer, W. P. C. (1994)

Proc. Natl. Acad. Sci. USA 91:10747–10751; Stemmer, W. P. C. (1994) Nature 370:389–391).

Mammalian mitochondrial enoyl-CoA hydratase is an independent enzyme (Minami-Ishi et al. (1989) Eur. J. Biochem. 185:73–78) which catalyzes the formation of S-(+)-3-hydroxyacyl-CoA (encoded by GenBank Accession No. U37486, SEQ ID NO: 22). The DNA encoding this enzyme can be subjected to shuffling to alter the activity of this enzyme to form the R-(−) instead of the S-(+)-epimer. Then, the shuffled DNA can be modified further to include nucleotide sequences which encodes a signal sequence for targeting to the peroxisomes.

Recently, a 2-enoyl-CoA hydratase from Aeromonas caviae was reported to hydrate 2-enoyl-CoA to R-3-hydroxyacyl-CoA (DDBJ Accession No. E15860, SEQ ID NO: 21) (Fukui et al. (1998) J. Bacteriol. 180:667–673). This enzyme can be modified to include a signal sequence for targeting to plant peroxisomes. Together with a peroxisome-localized PHA synthase, such an enoyl-CoA hydratase can catalyze the biosynthesis of copolymers.

Example 2

Production of Specific Types of PHA in Plants

It is desirable to produce a pure copolymer of a defined monomer composition. A relatively pure copolymer would have predictable properties in comparison to a mixture of copolymers as the composition of the latter can vary according to the environment. The ability of Pseudomonas sp. to make copolymers of PHAs from various substrates is well known to those skilled in the art. However, the PHA synthases from these species have a broad substrate range (Caballero et al. (1995) Int. J. Biol. Macromol. 17:86–92; Huisman et al. (1989) Appl. Environ. Microbiol. 55:1949–1954; Lee et al. (1995)Appl. Environ. Microbiol. 42:901–909; Ramsay et al. (1990) Appl. Environ. Microbiol. 56:2093–2098; Steinbuechel et a? (1992) Appl. Environ. Microbiol. 37:691–697; Timm et al. (1992) Eur. J. Biochem. 209:1R–30). When a genomic fragment containing the PHA synthase gene from Thiocapsa pfennigii (see, WO 96/08566) was introduced into Pseudomonas putida or A. eutrophus strains deficient in PHA synthase, majority of the copolymer made was polyhydroxybutyrate-co-hydroxyhexanoate (HB-co-HHX) (Liebergesell et al. (1993) Appl. Environ. Microbiol. 40:292–300; Valentin et al. (1994) Appl. Environ. Microbiol 40:710–716). These are the first reports of an enzyme overcoming the barrier between short- and medium-chain monomers with respect to substrate specificity for copolymer synthesis.

Recently, a PHA synthase has been identified from A. caviae (DDBJ Accession No. D88825, SEQ ID NO: 11) that also makes primarily poly(hydroxybutyrate-co-hydroxyhexanoate) copolymer when the bacteria are grown in cultures containing octanoate or (Fukui et al. (1997) J. Bacteriol. 1 79:4821–4830). This enzyme, when transformed into an A. eutrophus strain that is deficient in PHB synthase, confers upon it the ability to make poly(hydroxybutyrate-co-hydroxyhexanoate), indicating that this enzyme is specific for these two substrates (Fukui et al. (1997) J. Bacteriol. 179: 4821–4830). Copolymers consisting mainly of poly(hydroxybutyrate-co-hydroxyhexanoate) can be produced if either T. pfennigii or A. caviae synthase is targeted to the plant peroxisomes along with an enoyl-CoA hydratase, 3-ketoacyl-CoA reductase, or 3-hydroxyacyl-CoA dehydrogenase that is capable of producing the R-(−) epimer (FIG. 3).

Figure 3:
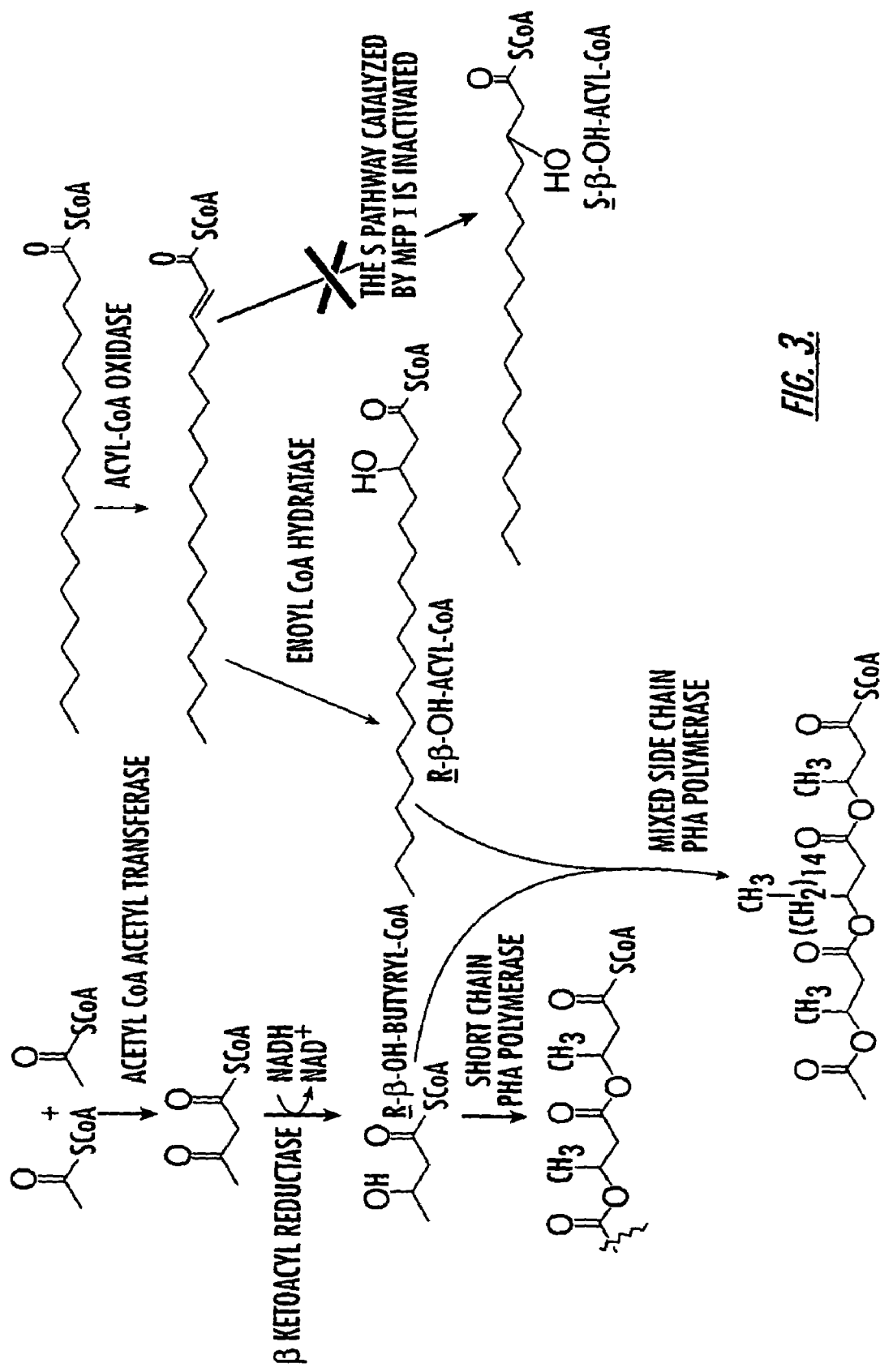
FIG. 3 schematically depicts the biosynthetic pathways for the synthesis PHB and PHA copolymers which are composed of 3-hydroxybutanoic acid monomers and other 3-hydroxyalkanoate monomers.

By introducing the other two enzymes (ketothiolase and reductase) of the PHA biosynthetic pathway into the peroxisomes, a large portion of acetyl-CoA should be partitioned to the synthesis of PHA (FIGS. 1 and 3). As ketothiolase is the most limiting enzyme in β-oxidation and is not associated with other enzymes (Kindl, H. (1987) Lipids: Structure and Function, P. K. Stumpf, ed. (Orlando, Fla.: Academic Press, Inc.), pp. 31–52), 3-ketobutyryl-CoA, the penultimate product of the last cycle of β-oxidation, should be readily available to the introduced reductase for conversion into 3-hydroxybutyryl-CoA. Assuming the dominant fatty acid being degraded through β-oxidation is $C_{18}$, 3-ketobutyryl-CoA would constitute >20% of the carbon flux through β-oxidation. Even if the reductase can use 25% of this intermediate, that would entail a diversion of 5% carbon from fatty acids passing through β-oxidation toward PHA formation. Introducing ketothiolase would further augment the level of 3-ketobutyryl-CoA in peroxisomes.

Expression of PHB biosynthetic machinery in the peroxisomes along with that in the plastids as well as cytosol can lead to more PHB deposition in seeds. Previously, it has been reported that the expression of PHB biosynthetic enzymes in the cytosol of plants resulted in plants being of reduced vigor or "sick" (Poirier et al. (1992) Science 256: 520–523). In this study, only reductase and synthase were expressed, however, allowing the cytosolic ketothiolase to supply acetoacetyl-CoA for PHB synthesis. Acetoacetyl-CoA, however, is a substrate for the synthesis of other cellular components, such as secondary metabolites and phytohormones. Enough acetoacetyl-CoA may have been diverted toward the formation of PHB that the homeostatic limits for normal cell metabolism were diminished. Alternatively, PHB granules might have physically caused disturbance in the leaf cytosol, affecting metabolism in general. The physiology of leaves may limit their usefulness as a site of PHB synthesis. A mature leaf is a source of photosynthate and as such produces and supplies photosynthate to sinks within the plant. On the other hand, a developing seed is a strong sink. Due to the myriad physiological differences between a source leaf and a strong sink like a developing seed, expression of genes encoding enzymes involved in PHB synthesis in the cytosol of a developing seed may not be as toxic as in that of a leaf. Expression of these genes in the peroxisomes of seeds can be driven by seed-preferred, chemical-regulatable or germination-preferred promoters. If these genes need to be expressed during both seed fill and germination or during only a limited portion of the seed fill period, a chemical-regulatable promoter may be desirable.

It is further recognized that in the practice of the invention, it can be advantageous to make use of transgenic or naturally occurring lines of oilseed plants that are known to have higher rates of β-oxidation in their seeds to achieve optimal PHA production in a plant.

Example 3

Engineering a Peroxisomal 2-Enoyl-CoA Hydratase From a Yeast Multifunctional Protein To produce PHA in plant peroxisomes, it is essential to effectively divert 2-enoyl-CoA from β-oxidation and to the synthesis of R-(−)-3-hydroxyacyl-CoA, the substrate of PHA synthase. In contrast to the multifunctional protein in other organisms, yeast multifunctional protein (encoded by GenBank Accession No. M86456, SEQ ID NO: 3) converts trans-2-enoyl-CoA to R-(−)-3-hydroxyacyl-CoA. The hydratase domain of the yeast multifunctional protein utilizes a broader chain-length range of substrates than does the hydratase isolated from *Aeromonas caviae*(Fukui et al. (1998) *J. Bacteriol.* 180:667–673). Such a hydratase with such a broad substrate range finds use in the production of a wide variety of copolymers in plants.

Thus, the R-specific enoyl-CoA hydratase of the yeast multifunctional protein can used to produce R-(−)-3-hydroxyacyl-CoA for PHA synthesis in plant peroxisomes. Since the R-(−)-3-hydroxyacyl-CoA dehydrogenase of the yeast multifunctional protein requires NADH and the NADH-binding sites are located in the N-terminal portion of the polypeptide, the hydratase is likely located in the C-terminal portion of the yeast multifunctional protein. Filppula et al. ((1995) *J. Biol. Chem.* 270:27453–27457) constructed a C-terminally truncated form of the yeast multifunctional protein and showed that the mutant enzyme contained only R-(−)-3-hydroxyacyl-CoA dehydrogenase activity and thus demonstrated that the deleted C-terminal portion of the full-length yeast multifunctional protein is essential for hydratase activity. Qin et al. (1997) *Biochem. J.* 321: 21–28 described an N-truncated rat multifunctional protein with 318 amino acid residue deletion. This mutant enzyme remained full hydratase activity while its dehydrogenase activity was completely lost. These observations are in agreement with the prediction that an N-terminally truncated form of yeast multifunctional protein possess hydratase activity and lack dehydrogenase activity.

To engineer a 2-enoyl-CoA hydratase that catalyzes the synthesis of R-(−)-hydroxyacyl-CoA, the nucleotide sequence encoding the yeast multifunctional protein (GenBank Accession No. M86456, SEQ ID NO: 3) can be modified by site-directed mutagenesis and/or N-terminal truncation to remove the dehydrogenase activity. After analyzing the primary structure of the yeast multifunctional protein, two putative NADH-binding domains (residues 152–180 and residues 456–484) were identified. These two putative NADH-binding domains each possess the conserved Y and K that are a signature NADH-binding-sites. Y165 and K169 lie in the first domain while Y478 and K482 are found in the second domain, although it is unknown whether the first domain, the second one or both of them serves for NAD/NADH-binding. To eliminate dehydrogenase activity, the NADH binding sites can be disrupted to generate mutant yeast multifunctional proteins such as, for example, a first mutant enzyme having the two amino acid substitutions, Y165F and K169A and a second mutant enzyme having the two amino acid substitutions Y478F and K482A and a third mutant enzyme having the four amino acid substitutions, Y165F, K169A, Y478F, and K482A. Alternatively, two N-terminally truncated versions of the yeast multifunctional protein can be constructed by eliminating one and both NADH-binding sites (FIG. 2). Methods for assaying such enzyme activities are known in the art. See, for example, Moskowitz and Merrick (1969) *Biochemistry* 8:2748–2755 (enoyl-CoA hydratase), and Lynen and Wieland (1955) *Meth. Enzymol.* 1:566–573 (ketoacyl-CoA reductase) and Example 6 infra.

An N-terminally truncated version of the yeast multifunctional protein is set forth in SEQ ID NO: 5. A nucleotide sequence for the truncated yeast multifunctional protein is set forth in SEQ ID NO: 4. A similar approach can be used to modify any multifunctional protein known in the art.

The resulting 2-enoyl-CoA hydratase enzyme can then be modified for targeting to the peroxisome by operably linking a peroxisome-targeting signal sequence to the coding sequence for the mutant enzyme.

Example 4

Engineering a Peroxisomal 3-ketoacyl-CoA Reductase from a Yeast Multifunctional Protein R-(−)-3-hydroxybutyryl-coenzyme A dehydrogenase (also known as acetoacetyl-CoA reductase) is encoded by phaB in PHA biosynthesis in a number of microorganisms. Such R-(−)-3-hydroxybutyryl-coenzyme A dehydrogenases all utilize NADPH as the electron donor. In one report an acetoacetyl-CoA reductase was shown to be NADH-dependent, but it produced S-(+)-3-hydroxybutyryl-CoA as its product (Liebergesell and Steinbuchel (1992) *Eur. J. Biochem.* 209:135–150). Another report showed that an NADH-dependent acetoacetyl-CoA reductase was isolated from *Parracoccus denitrificans* (Yabutani (1995) *FEMS Microbiol. Lett.* 133:85–90). Subsequent characterization confirmed that it utilized NADPH, but not NADH as an electron donor (Madison and Huisman (1999) *Microbiol. Mol. Biol. Rev.* 63:21–53).

In plant peroxisomes, it is postulated that NADPH pool is limited while NADH predominates. It is doubtful that the phaB gene product, an NADPH-dependent reductase, will function in peroxisomes. Therefore, a new enzyme that utilizes NADH as the electron donor is desired. The desired enzyme must also be able to convert 3-acetoacetyl-CoA and to R-(−)-3-hydroxybutyryl-CoA. Preferably, the desired enzyme is also capably of converting any 3-ketoacyl-CoA to an R-(−)-3-hydroxyacyl-CoA.

Using protein engineering methods, the coding sequence of the yeast multifunctional protein can be modified to produce the desired enzyme. The dehydrogenase moiety of the yeast multifunctional protein utilizes R-(−)-3-hydroxyacyl-CoA and requires NADH as its electron acceptor. Since the dehydrogenase of the yeast multifunctional protein enzyme utilizes substrates of fatty acyl-CoAs with $C_4$ or longer chain length, the desired enzyme is expected to catalyze the NADH-dependent reduction of acetoacetyl-CoA to R-(−)-3-hydroxybutyryl-CoA. Based on sequence analysis of primary structure of the protein, two NADH-binding sites residing at the N-terminal portion were identified. For example, to produce the desired 3-ketoacyl-CoA reductase, the nucleotide sequence encoding the of yeast multifunctional protein can be truncated to produce a nucleotide sequence that encodes a C-terminally truncated version of the yeast multifunctional protein which lacks the final 271 amino acid of amino acid sequence of the yeast multifunctional protein. The C-terminally truncated version of the yeast multifunctional protein is set forth in SEQ ID NO: 7. A nucleotide sequence encoding the truncated yeast multifunctional protein is set forth in SEQ ID NO: 6.

The desired 3-ketoacyl-CoA reductase can then be modified, if necessary, for targeting to the peroxisome by operably linking a peroxisome-targeting signal sequence to the coding sequence for the desired enzyme.

Example 5

A Novel Maize Protein with Homology to Yeast MFP2

To search for homologous sequences in maize, the nucleotide sequence encoding the yeast MFP2 (GenBank Accession No. M86456, SEQ ID NO: 3) was used to search a Pioneer Hi-Bred maize EST database. An EST clone with substantial homology to the yeast sequence was identified. The 1362 bp maize EST clone was sequenced and found to be full-length (SEQ ID NO: 1) with an open reading frame encoding a polypeptide of 314 amino acids (SEQ ID NO: 2). Interestingly, in comparison, the yeast MFP2 is comprised of an amino acid sequence which is 900 amino acids in length. Further sequence analysis revealed that the maize amino acid sequence corresponds to the C-terminal portion of the yeast MFP2 that is believed to be a 2-enoyl-CoA hydratase domain (FIG. 2) Unlike the yeast MFP2, the smaller maize MFP2-like polypeptide lacks the dehydrogenase domain of the yeast and mammalian MFP2s and does not appear to contain a peroxisome-targeting sequence.

Thus, on the basis of homology to the yeast MFP2, the maize MFP2-like polypeptide is predicted to encode a 2-enoyl-CoA hydratase. Such a hydratase can be targeted to the peroxisome for use in PHA production therein by operably linking a peroxisome-targeting signal sequence to the coding sequence for the maize polypeptide.

The present invention discloses a novel protein from maize with homology to MFP2s. While MFP2s are found in several fungi and in several mammals including, but not limited to, mouse, guinea pig, human and pig, no plant sequence has yet been publically disclosed. It has been generally believed that MFPs are unique to fungi and animals. The discovery of the maize MFP2-like polypeptide, which shares substantial homology with the yeast MFP2, indicates, however that, at least, the hydratase domain of MFP2 is also found in plants.

While the maize MFP2-like polypeptide shares significant homology to MFP2s from fungi and mammals, the maize protein possesses several notable differences. In addition to the lack of a dehydrogenase domain, the maize MFP2-like polypeptide does not contains any known peroxisomal-targeting sequences in its N-terminal or C-terminal portions. This is different from yeast and mammalian MFP2s which are considered to be localized in peroxisomes and play roles in fatty acid β-oxidation. Thus, the maize MFP2-like polypeptide is likely to play a physiological role in plants that is distinct from that of known MFP2s.

Example 6

Assaying the Activities of PHA Synthesis Enzymes

Figure 4:
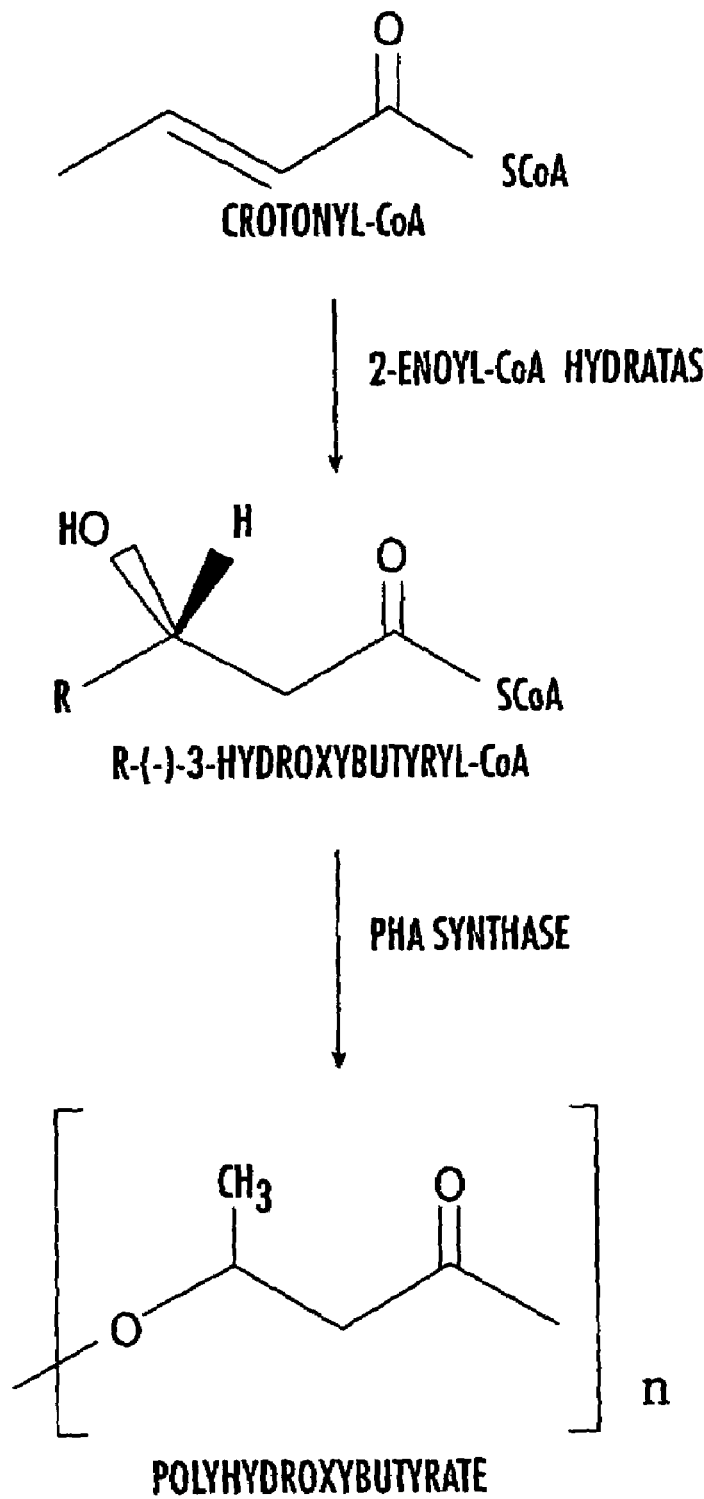
FIG. 4 schematically illustrates a functional assay for a 2-enoyl-CoA hydratase that catalyzes the synthesis of R-(−)-3-hydroxyacyl-CoA. This hydratase converts crotonyl-CoA to R-(−)-3-hydroxyacyl-CoA which is then utilized as the substrate by PHA synthase to form polymers. PHA synthase utiltizes R-(−)-3-hydroxyacyl-CoAs, but not S-3-hydroxyacyl-CoAs. Detection of polymer formation in the presence of crotonyl-CoA demonstrates that R-(−)-3-hydroxyacyl-CoA was produced.

To test the activity of the maize MFP2-like polypeptide and the truncated yeast MFP2 (hydratase domain) prepared as described supra, their respective nucleotide sequences (SEQ ID NOs: 1 and 4) and that of the full-length yeast MFP2 (SEQ ID NO: 3) were cloned into appropriate bacterial expression vectors and used to transform E. coli using standard techniques known in the art for expressing recombinant proteins and transforming bacteria. Total protein extracts were isolated from IPTG-induced E. coli (strain BL21) harboring a plasmid comprising the nucleotide sequence of SEQ ID NO: 3 (pYMFP), the nucleotide sequence of SEQ ID NO: 4 (pYHL) or the nucleotide sequence of SEQ ID NO: 1 (pMHL). The activities of the truncated proteins were tested using the functional assay schematically illustrated in FIG. 4. The reaction mixture consisted of 20 µl of PHA synthase preparation (19 mg/ml), 50 µl of E. coli extract, 50 mM Tris-HCl, pH 7.5 and µM of crotonyl-CoA, acetoacetyl-CoA (AcAcCoA), or 3-hydroxybutryl-CoA (3HB-CoA) in total volume of 300 µl. The reaction was started by the addition of the substrate and incubated at 37° C. for two hours.

Figure 5:
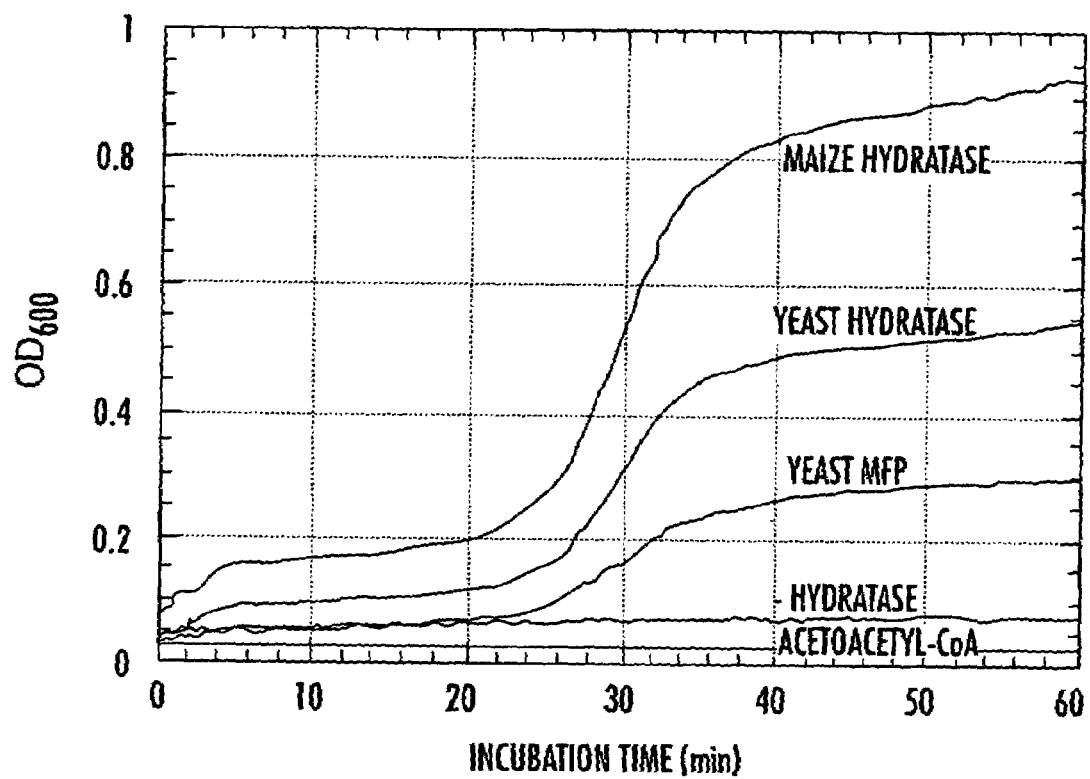
FIG. 5 is a graphical depiction of the results of a functional assay for the activity of a 2-enoyl-CoA hydratase that catalyzes the synthesis R-(−)-3-hydroxyacyl-CoA.

The results are presented in Table 1 and FIG. 5. With crotonyl-CoA as a substrate, polymer formation was detected in cultures of E. coli that were transformed with a nucleotide sequences encoding either the full-length yeast MFP2 (pYMFP), the truncated yeast MFP2 (yYHL), or the maize MFP2-like polypeptide (yMHL). The vector-only control (Table 1, reaction 1) indicated that polymer was not formed in the presence of crotonyl-CoA without one of the three nucleotide sequences (SEQ ID NOs: 1, 3, and 4). Thus, proteins encoded by each of the nucleotide sequences can catalyze the conversion of a crotonyl-CoA, which is a 2-enoyl-CoA, into R-(–)-3-hydroxyacyl-CoA, which can then be used for PHA synthesis as a substatrate for PHA synthase.

Comparison of the relative hydratase activities, as measured by PHA formation, for the proteins encoded by SEQ ID NOs: 1, 3 and 4 is provided in FIG. 5. The highest relative hydratase activity was detected in the cultures expressing the maize MFP2-like polypeptide (maize hydratase), followed by the truncated yeast MFP2 (yeast hydratase) and the full-length yeast MFP2 (yeast MFP). The results indicate that the removal an N-terminal portion of an MFP2 can lead to increased hydratase activity, as determined by increased PHA production, when compared to the hydratase activity of the full-length MFP2.

In general, the results presented in Table 1 and FIG. 5 demonstrate that both the maize MFP2-like polypeptide and the truncated yeast MFP2 possess a hydratase activity that can be used for PHA synthesis in a host cell. Given that 2-enoyl-CoA substrates are found in the peroxisome, the maize MFP2-like polypeptide and the truncated yeast MFP2 of the invention can be targeted to peroxisome, along with other necessary enzymes, for PHA synthesis therein. The results further demonstrate that a truncated MFP2 can provide an improvement in PHA production in an living organism, when compared to the full-length MFP.

TABLE 1

Functional Assay for the Presence of an 2-enoyl-CoA Hydratase Activity

| Reaction | Substrate | Hydratase | Polymer Formed |
| --- | --- | --- | --- |
| 1 | crotonyl-CoA | vector only | No |
| 2 | crotonyl-CoA | pMHL | Yes |
| 3 | crotonyl-CoA | pYHL | Yes |
| 4 | crotonyl-CoA | pYMFP | Yes |
| 5 | 3HB-CoA | 50 µl buffer | Yes |
| 6 | AcAcCoA | 50 µl buffer | No |
| 7 | AcAcCoA | pMHL | No |

Example 7

Transformation and Regeneration of Transgenic Maize Plants by Particle Bombardment Immature maize embryos from greenhouse donor plants are bombarded with a plasmid comprising a nucleotide sequence of the invention encoding an enzyme involved in PHA synthesis operably linked to a seed-preferred promoter and the selectable marker gene PAT (Wohlleben et al. (1988) Gene 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the nucleotide sequence of the invention encoding an enzyme involved in PHA synthesis linked to a seed-preferred promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for PHA content and/or the activity or level of the enzyme of the invention.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117–074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 111117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 8

Production of Transgenic Maize Plants via *Agrobacterium*-Mediated Transformation For *Agrobacterium*-mediated transformation of maize with a nucleotide sequence of the invention encoding an enzyme involved in PHA synthesis, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 9

Production of Transformed Soybean Plants

Soybean embryos are bombarded with a plasmid comprising a nucleotide sequence of the invention encoding an enzyme involved in PHA synthesis operably linked to a seed-preferred as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS 1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the nucleotide sequence of the invention operably linked to the seed-preferred promoter can be isolated as a restriction fragment. This fragment can then be inserted into a unique restriction site of the vector carrying the marker gene.

To 50 μl of a 60 mg/ml μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μof anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Genetic Transformation of Sunflower Plants

Sunflower meristem tissues are transformed with an expression cassette comprising a nucleotide sequence of the invention encoding an enzyme involved in PHA synthesis operably linked to a seed-preferred promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.* 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000®particle acceleration device.

Disarmed *Agrobacterium tumefaciens* strain EHA105 is used in all transformation experiments. A binary plasmid vector comprising the expression cassette that contains the nucleotide sequence of the invention encoding an enzyme involved in PHA synthesis operably linked to the seed-preferred promoter is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD$_{600}$ of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an *Agrobacterium* suspension, mixed, and left undisturbed for 30 minutes.

The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development, Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying, for example, for PHA production as described supra.

NPTII-positive shoots are grafted to Pioneer® hybrid 6440 in vitro-grown sunflower seedling rootstock. Surface sterilized seeds are germinated in 48–0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by analysis in leaf extracts of enzyme activity of the enzyme encoded by the nucleotide sequence of the invention of leaf extracts, while transgenic seeds harvested from NPTII-positive $T_0$ plants are identified by similar enzyme activity analyses of small portions of dry seed cotyledons.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleotide molecule comprising a nucleotide sequence selected from the group consisting of:
   (a) the nucleotide sequence set forth in SEQ ID NO: 1;
   (b) a nucleotide sequence encoding the amino acid sequence set forth in SEQ ID NO: 2;
   (c) a nucleotide sequence encoding a protein comprising 2-enoyl-CoA hydratase activity,
   wherein said nucleotide sequence has at least 90% sequence identity to the nucleotide sequence set forth in SEQ ID NO: 1;
   (d) the antisense nucleotide sequence complementary to the nucleotide sequence of (a), (b) or (c); and
   (e) a nucleotide sequence encoding a protein comprising 2-enoyl-CoA hydratase activity,
   wherein said nucleotide sequence hybridizes under high stringency conditions to the nucleotide sequence of (a); wherein high stringency conditions are hybridization in 50% formamide, 1M NaCl, 1% SDS at 37° C., and a wash in 0.1×SSC at 60 to 65° C.

2. An expression cassette comprising a nucleotide sequence of a nucleotide molecule of claim 1, said nucleotide sequence operably linked to a promoter that drives expression in a host cell.

3. A host cell transformed with the expression cassette of claim 2.

4. The host cell of claim 3, wherein said host cell is selected from the group consisting of a plant cell, a bacterial cell, and a yeast cell.

5. The isolated nucleotide molecule of claim 1, wherein said nucleotide sequence has at least 95% sequence identity to the nucleotide sequence set forth in SEQ ID NO; 1.

6. The isolated nucleotide molecule of claim 1, wherein said nucleotide sequence is the nucleotide sequence set forth in SEQ ID NO: 1.

7. The isolated nucleotide molecule of claim 1, wherein said nucleotide sequence encodes the amino acid sequence set forth in SEQ ID NO: 2.

8. A transgenic plant comprising in its genome at least one stably integrated DNA construct comprising a nucleotide sequence operably linked to a promoter that drives expression in a plant, wherein said nucleotide sequence is selected from the group consisting of:
   (a) the nucleotide sequence set forth in SEQ ID NO: 1;
   (b) a nucleotide sequence encoding the amino acid sequence set forth in SEQ ID NO: 2;
   (c) a nucleotide sequence encoding a protein comprising 2-enoyl-CoA hydratase activity, wherein said nucleotide sequence has at least 90% sequence identity to the nucleotide sequence set forth in SEQ ID NO: 1;
   (d) the antisense nucleotide sequence complementary to the nucleotide sequence of (a), (b) or (c); and
   (e) a nucleotide sequence encoding a protein comprising 2-enoyl-CoA hydratase activity, wherein said nucleotide sequence hybridizes under high stringency conditions to the nucleotide sequence of (a): wherein high stringency conditions are hybridization in 50% formamide, 1M NaCl, 1% SDS at 37° C., and a wash in 0.1×SSC at 60 to 65°C.

9. The plant of claim 8, wherein said promoters are selected from the group consisting of seed-preferred promoters, chemical-regulatable promoters, germination-preferred promoters, and leaf-preferred promoters.

10. The plant of claim 8, wherein said plant is a monocot.

11. The plant of claim 10, wherein said monocot is selected from the group consisting of maize, wheat, rice, sorghum, rye, millet, barley, palm and banana.

12. The plant of claim 8, wherein said plant is a dicot.

13. The plant of claim 12, wherein said dicot is selected from the group consisting of soybean, sunflower, safflower, alfalfa, potato, Brassica spp., cotton, tomato, tobacco and peanut.

14. A seed or the plant of claim 8, wherein said seed comprises said DNA construct.

15. A transformed plant cell comprising in its genome at least one stably integrated DNA construct comprising a nucleotide sequence operably linked to a promoter that drives expression in a plant cell, wherein said nucleotide sequence is selected from the group consisting of:
   (a) the nucleotide sequence set forth in SEQ ID NO: 1;
   (b) a nucleotide sequence encoding the amino acid sequence set forth in SEQ ID NO: 2;
   (c) a nucleotide sequence encoding a protein comprising 2-enoyl-CoA hydratase activity, wherein said nucleotide sequence has at least 90% sequence identity to the nucleotide sequence set forth in SEQ ID NO: 1;
   (d) the antisense nucleotide sequence complementary to the nucleotide sequence of (a), (b) or (c); and
   (e) a nucleotide sequence encoding a protein comprising 2-enoyl-CoA hydratase activity, wherein said nucleotide sequence hybridizes under high stringency conditions to the nucleotide sequence of (a); wherein high stringency conditions are hybridization in 50% formamide 1M NaCl, 1% SDS at 37° C., and a wash in 0.1×SSC at 60 to 65° C.

* * * * *

UNITED STATES PATENT AND TRADEMARK OFFICE
CERTIFICATE OF CORRECTION

| | |
|---|---|
| PATENT NO. | : 7,176,349 B1 |
| APPLICATION NO. | : 10/089281 |
| DATED | : February 13, 2007 |
| INVENTOR(S) | : Dhugga et al. |

It is certified that error appears in the above-identified patent and that said Letters Patent is hereby corrected as shown below:

Column 124:

Line 40: "or" should read --of--

Signed and Sealed this

Tenth Day of February, 2009

JOHN DOLL
*Acting Director of the United States Patent and Trademark Office*